US012534517B2

(12) United States Patent
Diehl et al.

(10) Patent No.: US 12,534,517 B2
(45) Date of Patent: Jan. 27, 2026

(54) HIGHLY SPECIFIC ZIKA NEUTRALIZING HUMAN ANTIBODIES

(71) Applicants: The University of Vermont and State Agricultural College, Burlington, VT (US); The University of North Carolina at Chapel Hill, Chapel Hill, NC (US)

(72) Inventors: Sean Diehl, Shelburne, VT (US); Aravinda de Silva, Chapel Hill, NC (US); Matthew Collins, Chapel Hill, NC (US); Ben McElvany, Burlington, VT (US); Huy Tu, Burlington, VT (US)

(73) Assignees: The University of Vermont and State Agricultural College, Burlington, VT (US); The University of North Carolina at Chapel Hill, Chapel Hill, NC (US)

( * ) Notice: Subject to any disclaimer, the term of this patent is extended or adjusted under 35 U.S.C. 154(b) by 1433 days.

(21) Appl. No.: 16/765,509

(22) PCT Filed: Nov. 21, 2018

(86) PCT No.: PCT/US2018/062233
§ 371 (c)(1),
(2) Date: May 20, 2020

(87) PCT Pub. No.: WO2019/104157
PCT Pub. Date: May 31, 2019

(65) Prior Publication Data

US 2021/0054055 A1 Feb. 25, 2021

Related U.S. Application Data

(60) Provisional application No. 62/589,006, filed on Nov. 21, 2017.

(51) Int. Cl.

| | |
|---|---|
| ***A61K 39/12*** | (2006.01) |
| ***A61K 39/395*** | (2006.01) |
| ***A61K 39/42*** | (2006.01) |
| ***A61P 31/14*** | (2006.01) |
| ***C07K 14/18*** | (2006.01) |
| ***C07K 16/08*** | (2006.01) |
| ***C07K 16/10*** | (2006.01) |
| *A61K 39/00* | (2006.01) |

(52) U.S. Cl.
CPC .......... *C07K 16/1081* (2013.01); *A61K 39/12* (2013.01); *A61K 39/395* (2013.01); *A61K 39/42* (2013.01); *A61P 31/14* (2018.01); *C07K 14/1825* (2013.01); *A61K 2039/505* (2013.01); *C07K 2317/33* (2013.01); *C07K 2317/56* (2013.01); *C07K 2317/565* (2013.01); *C07K 2317/622* (2013.01); *C07K 2317/76* (2013.01); *C07K 2317/92* (2013.01); *C12N 2770/24134* (2013.01)

(58) Field of Classification Search
CPC ............ C07K 16/1081; C07K 2317/33; C07K 2317/56; C07K 2317/565; C07K 2317/622; C07K 2317/76; C07K 2317/92; C07K 2317/21; C07K 14/1816; C07K 14/1825; C07K 14/005; C07K 14/08; C07K 16/08; A61K 39/12; A61K 2039/505; A61K 39/395; A61K 39/42; A61P 31/14; C12N 2770/24134; Y02A 50/30
See application file for complete search history.

(56) References Cited

U.S. PATENT DOCUMENTS

| | | | | |
|---|---|---|---|---|
| 9,334,331 | B2 * | 5/2016 | Igawa | C07K 16/40 |
| 10,421,807 | B2 * | 9/2019 | Gonzales | A61P 11/00 |
| 2015/0328303 | A1 | 11/2015 | De Silva et al. | |
| 2017/0014502 | A1 | 1/2017 | Sumathy et al. | |
| 2017/0233459 | A1 | 8/2017 | Hooper et al. | |
| 2017/0298119 | A1 | 10/2017 | Wollacott et al. | |

FOREIGN PATENT DOCUMENTS

WO WO 2017/132210 A1 8/2017

OTHER PUBLICATIONS

Al Qaraghuli et al. (2020, Nature Scientific Reports 10:13969).*
Edwards et al. (2003, JMB 334:103-118).*
Lloyd et al. (2009, Protein Engineering, Eng. Design & Selection 22(3): 159-168).*
Goel et al. (2004, J. Immunol. 173: 7358-7367).*
Khan et al. (2014, J. Immunol. 192: 5398-5405).*
Poosarla et al. (2017, Biotechn. Bioeng. 114(6): 1331 -1342).*
Rabia, et al. (2018, Biochemical Engineering Journal 137:365-374).*
Chiu, M., et al., "Antibody structure and function: The basis for engineering therapeutics." Antibodies 2019 8(4), 55 (Year: 2019).*
Bhattacharya et al. Impact of genetic variation on three dimensional structure and function of proteins. PLoS One 12(3): e0171355, 2017.*
Bork, P. Powers and pitfalls in sequence analysis: the 70% hurdle. Genome Res 10: 398-400, 2000.*
Bork, P. Go hunting in sequence databases but watch out for the traps. Trends in Genetics 12(10): 425-427, 1996.*
Brenner. S.E. Errors in genome annotation. Trends in Genetics 15:132-133, 1999.*

(Continued)

*Primary Examiner* — Bridget E Bunner
(74) *Attorney, Agent, or Firm* — Wolf, Greenfield & Sacks, P.C.

(57) ABSTRACT

Provided herein, in some embodiments, are compositions of Zika-specific antibodies and antigen-binding fragments thereof and methods of using the antibodies and antigen-binding fragments.

9 Claims, 31 Drawing Sheets

Specification includes a Sequence Listing.

(56) References Cited

OTHER PUBLICATIONS

Brorson et al. Mutational analysis of avidity and fine specificity of anti-levan antibodies. J Immunol 163: 6694-6701, 1999.*
Brummell et al. Probing the combining site of an anti-carbohydrate antibody by saturation-mutagenesis: role of the heavy-chain CDR3 residues. Biochem 32(4): 1180-1187, 1993.*
Burks et al. In vitro scanning saturation mutagenesis of an antibody binding pocket. Proc Natl Acad Sci USA 94: 412-417, 1997.*
Colman Research in Immunol. 145:33-36, 1994.*
Chuh et al. Chemical Methods for Encoding and Decoding of Posttranslational Modifications. Cell Chem Biol 23: 86-107, 2016.*
Doerks et al. Protein annotation: detective work for function prediction. Trends in Genetics 14:248-250, 1998.*
Fenton et al. Rheostat positions: a new classification of protein positions relevant to pharmacogenomics. Medicinal Chem Res 29: 1133-1146, 2020.*
Gentilucci et al. Chemical Modifications Designed to Improve Peptide Stability: Incorporation of Non-Natural Amino Acids, Pseudo-Peptide Bonds, and Cyclization. Curr Pharm Design 16: 3185-3203, 2010.*
Guo et al. Protein tolerance to random amino acid change. Proc Natl Acad Sci USA 101(25): 9205-9210, 2004.*
Ikeuchi et al. Delicate balance among thermal stability, binding affinity, and conformational space explored by single-domain VHH antibodies. Sci Reports 11: 20624, 2021 (9 total pages).*
Jang et al. The structural basis for DNA binding by an anti-DNA autobody. Mol Immunol 35: 1207-1217, 1998.*
Kobayashi et al. Tryptophan H33 plays an important role in pyrimidine (6-4) pyrimidone photoproduct binding by a high-affinity antibody. Protein Engineering 12(10): 879-884, 1999.*
Rudikoff et al. Single amino acid substitution altering antigen-binding specificity. Proc Natl Acad Sci USA 79: 1979-1983, 1982.*
Skolnick et al. From genes to protein structure and function: novel applications of computational approaches in the genomic era. Trends Biotechnol 18(I):34-39 2000.*
Smith et al. The challenges of genome sequence annotation or "the devil is in the details". Nature Biotechnol 15: 1222-1223, 1997.*
Tokuriki et al. Stability effects of mutations and protein evolvability. Curr Opin Structural Biol 19: 596-604, 2009.*
Vasudevan et al. A single amino acid change in the binding pocket alters specificity of an anti-integrin antibody AP7.4 as revealed by its crystal structure. Blood Cells Mol Diseases 32: 176-181, 2004.*
Zhang et al. Comprehensize optimization of a single-chain variable domain antibody fragment as a targeting ligand for a cytotoxic nanoparticle. mAbs 7(1): 42-52, 2015.*
Balmaseda et al., Antibody-based assay discriminates Zika virus infection from other flaviviruses. Proc Natl Acad Sci U S A. Aug. 1, 2017;114(31):8384-8389. doi: 10.1073/pnas.1704984114. Epub Jul. 17, 2017.
Dempsey LA. Zika-neutralizing antibodies. Nat Immunol. May 18, 2017;18(6):603. doi: 10.1038/ni.3762.
Stettler et al., Specificity, cross-reactivity, and function of antibodies elicited by Zika virus infection. Science. Aug. 19, 2016;353(6301):823-826. doi: 10.1126/science.aaf8505. Epub Jul. 14, 2016.
Wang et al., Molecular determinants of human neutralizing antibodies isolated from a patient infected with Zika virus. Sci Transl Med. Dec. 14, 2016;8(369):369ra179.
Wilson et al., A neutralization assay for Zika and Dengue viruses using a real-time PCR-based endpoint assessment. J Clin Microbiol. Aug. 9, 2017. pii: JCM.00673-17. doi:10.1128/JCM.00673-17.
International Search Report and Written Opinion for Application No. PCT/US2018/062233 mailed Feb. 11, 2019.
International Preliminary Report on Patentability for Application No. PCT/US2018/062233 mailed Jun. 4, 2020.
Dai et al., Structures of the Zika Virus Envelope Protein and Its Complex with a Flavivirus Broadly Protective Antibody. Cell Host Microbe. May 11, 2016;19(5):696-704. doi: 10.1016/j.chom.2016.04.013. Epub May 2, 2016.
Robbiani et al., Recurrent Potent Human Neutralizing Antibodies to Zika Virus in Brazil and Mexico. Cell. May 4, 2017;169(4):597-609.e11. doi: 10.1016/j.cell.2017.04.024.
Smith et al., The potent and broadly neutralizing human dengue virus-specific monoclonal antibody 1C19 reveals a unique cross-reactive epitope on the bc loop of domain II of the envelope protein. mBio. Nov. 19, 2013;4(6):e00873-13. doi: 10.1128/mBio.00873-13.
Wu et al., Neutralization of Zika virus by germline-like human monoclonal antibodies targeting cryptic epitopes on envelope domain III. Emerg Microbes Infect. Oct. 11, 2017;6(10):e89. doi: 10.1038/emi.2017.79.
Zhao et al., Structural Basis of Zika Virus-Specific Antibody Protection. Cell. Aug. 11, 2016;166(4):1016-1027. doi: 10.1016/j.cell.2016.07.020. Epub Jul. 27, 2016.

* cited by examiner

FRNT50 (ng/ml)

| | EDE1 C10 | A9E | G9E |
|---|---|---|---|
| H/PF/2013 | 16.2 | 4.7 | 4.7 |
| Dakar | 28.5 | 21.7 | 14.6 |
| PRV | 40.3 | 35.8 | 10.3 |
| MR766 | 0.2 | 5.3 | 2.3 |
| DENV4 | 88.9 | >10,000 | >10,000 |

| | FRNT50 (1/dilution) | | |
|---|---|---|---|
| | undeplt | control | ZIKV E80 |
| DT168 | 2985 | 2191 | 535 |
| DT172 | 992 | 1572 | 964 |
| DT206 | 2884 | 2473 | 413 |
| DT244 | 630 | 538 | 617 |

| | DT168 | DT172 |
|---|---|---|
| ZIKV+ polyclonal wells | 176 | 91 |
| ZIKV-TS polyclonal wells | 142 | 80 |
| ZIKV-CR polyclonal wells | 34 | 11 |
| Total immortalized MBCs screened | 14,400 | 9,600 |
| ZIKV-specific frequency (of immortalized MBC) | 1.2% | 0.9% |

HIGHLY SPECIFIC ZIKA NEUTRALIZING HUMAN ANTIBODIES

RELATED APPLICATION

This application is a national stage filing under 35 U.S.C. § 371 of international application number PCT/US2018/062233, filed Nov. 21, 2018, which was published under PCT Article 21(2) in English and claims the benefit under 35 U.S.C. § 119(e) of U.S. provisional application No. 62/589,006, filed Nov. 21, 2017, each of which is herein incorporated by reference in its entirety.

FEDERALLY SPONSORED RESEARCH

This invention was made with government support under Grant Number AI107731 awarded by the National Institutes of Health. The government has certain rights in the invention.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on May 20, 2020, is named V013970122US01-SEQ-JXV and is 84,221 bytes in size.

BACKGROUND OF THE INVENTION

Zika virus (ZIKV), a member of the Flaviviridae virus family, is a single-stranded positive-sense RNA virus that is spread by *Aedes* mosquitoes. It is related to Dengue, Yellow Fever, Japanese Encephalitis, and West Nile viruses. While it was previously contained to regions of Africa and Asia along a narrow equatorial belt, it has recently spread to areas of the Americas, and more severe clinical symptoms and outcomes have been observed. For example, in 2015, Zika virus (ZIKV) became a global health emergency as it spread throughout Latin America causing thousands of cases of birth defects. In adults, ZIKV infection can lead to Guillain-Barré syndrome, an autoimmune disease resulting in weakness of limbs and polyneuropathy. Fetuses in utero are especially susceptible to ZIKV infections, and consequences include placental insufficiency and congenital malformations, such as cerebral calcifications, microcephaly, and miscarriage. Therefore, ZIKV is now a global disease, which has led to extensive effort toward finding therapeutic solutions.

SUMMARY OF THE INVENTION

Aspects of the disclosure relate to a composition comprising an antibody or an antigen-binding antibody fragment that binds Domain 1 of Zika virus (ZIKV) Envelope protein (ED1) with an $IC_{50}$ of 50.0 ng/mL or less, and a pharmaceutically acceptable carrier. An additional aspect of the disclosure provides a composition comprising an antibody or an antigen-binding antibody fragment that binds Zika virus (ZIKV) strain MR 766 with an $IC_{50}$ of 20 ng/mL or less, and a pharmaceutically acceptable carrier.

In some embodiments, the antibody or an antigen-binding antibody fragment comprises a non-naturally occurring modification. In some embodiments, the antigen-binding antibody fragment is an scFv. In some embodiments, the antibody is a full-length antibody. In some embodiments, the full-length antibody is an IgG molecule.

In some embodiments, the antibody or the antigen-binding antibody fragment does not neutralize Dengue viruses (DENV) 1-4.

In some embodiments, the antibody or the antigen-binding antibody fragment comprises a heavy chain variable region comprising an amino acid sequence that is (i) identical to SEQ ID NO: 1, or (ii) at least 88% identical to SEQ ID NO: 1.

In some embodiments, the antibody or the antigen-binding antibody fragment comprises a light chain variable region comprising an amino acid sequence that is (i) identical to SEQ ID NO: 2, or (ii) at least 86% identical to SEQ ID NO: 2.

In some embodiments, the antibody or the antigen-binding antibody fragment comprises a heavy chain variable region comprising an amino acid sequence that is (i) identical to SEQ ID NO: 3, or (ii) at least 91% identical to SEQ ID NO: 3.

In some embodiments, the antibody or the antigen-binding antibody fragment comprises a light chain variable region comprising an amino acid sequence that is (i) identical to SEQ ID NO: 4, or (ii) at least 90% identical to SEQ ID NO: 4.

In some embodiments, the antibody or the antigen-binding antibody fragment comprises six complementarity-determining regions (CDRs), and wherein one of the CDRs comprises SEQ ID NO: 5. In some embodiments, the antibody or the antigen-binding antibody fragment comprises six CDRs, wherein one of the CDRs comprises SEQ ID NO: 6. In some embodiments, the antibody or the antigen-binding antibody fragment comprises six CDRs, wherein one of the CDRs comprises SEQ ID NO: 7. In some embodiments, the antibody or the antigen-binding antibody fragment comprises six CDRs, wherein one of the CDRs comprises SEQ ID NO: 8.

Aspects of the disclosure also include a nucleic acid encoding the antibody or the antigen-binding antibody fragment described herein.

A further aspect of the disclosure provides a method comprising: obtaining a biological sample from a subject; contacting the biological sample with one or more of the following: (1) an antibody or an antigen-binding antibody fragment that binds Domain 1 of Zika virus (ZIKV) Envelope protein domain (ED1) with an $IC_{50}$ of 50.0 ng/mL or less, (2) an antibody or an antigen-binding antibody fragment that binds Zika virus (ZIKV) strain MR 766 with an $IC_{50}$ of 20 ng/mL or less, (3) a polypeptide comprised of an A9E epitope, and/or (4) a polypeptide comprised of an ED1 epitope and determining whether Zika virus is present in the subject if either of (1) or (2) bind to a Zika virus antigen and/or (3) or (4) bind to a Zika antibody present in the biological sample.

In some embodiments, the antibody or the antigen-binding antibody fragment does not neutralize DENV1-4.

In some embodiments, the antibody or the antigen-binding antibody fragment comprises a heavy chain variable region comprising an amino acid sequence that is (i) identical to SEQ ID NO: 1, or (ii) at least 88% identical to SEQ ID NO: 1.

In some embodiments, the antibody or the antigen-binding antibody fragment comprises a light chain variable region comprising an amino acid sequence that is (i) identical to SEQ ID NO: 2, or (ii) at least 86% identical to SEQ ID NO: 2.

In some embodiments, the antibody or the antigen-binding antibody fragment comprises a heavy chain variable region comprising an amino acid sequence that is (i) identical to SEQ ID NO: 3, or (ii) at least 91% identical to SEQ ID NO: 3.

In some embodiments, the antibody or the antigen-binding antibody fragment comprises a light chain variable region comprising an amino acid sequence that is (i) identical to SEQ ID NO: 4, or (ii) at least 90% identical to SEQ ID NO: 4.

In some embodiments, the antibody or the antigen-binding antibody fragment comprises six complementarity-determining regions (CDRs), and wherein one of the CDRs comprises SEQ ID NO: 5. In some embodiments, the antibody or the antigen-binding antibody fragment comprises six CDRs, and wherein one of the CDRs comprises SEQ ID NO: 6. In some embodiments, the antibody or the antigen-binding antibody fragment comprises six CDRs, and wherein one of the CDRs comprises SEQ ID NO: 7. In some embodiments, the antibody or the antigen-binding antibody fragment comprises six CDRs, and wherein one of the CDRs comprises SEQ ID NO: 8.

The disclosure, in another aspect, provides a method of treating a subject with Zika virus, comprising administering an effective amount of an antibody or an antigen-binding antibody fragment that binds Zika virus (ZIKV) strain MR 766 with an $IC_{50}$ of 20 ng/mL or less to the subject.

In some embodiments, the antibody or the antigen-binding antibody fragment does not neutralize DENV1-4.

In some embodiments, the antibody or the antigen-binding antibody fragment comprises a heavy chain variable region comprising an amino acid sequence that is (i) identical to SEQ ID NO: 1, or (ii) at least 88% identical to SEQ ID NO: 1.

In some embodiments, the antibody or the antigen-binding antibody fragment comprises a light chain variable region comprising an amino acid sequence that is (i) identical to SEQ ID NO: 2, or (ii) at least 86% identical to SEQ ID NO: 2.

In some embodiments, the antibody or the antigen-binding antibody fragment comprises a heavy chain variable region comprising an amino acid sequence that is (i) identical to SEQ ID NO: 3, or (ii) at least 91% identical to SEQ ID NO: 3.

In some embodiments, the antibody or the antigen-binding antibody fragment comprises a light chain variable region comprising an amino acid sequence that is (i) identical to SEQ ID NO: 4, or (ii) at least 90% identical to SEQ ID NO: 4.

In some embodiments, the antibody or the antigen-binding antibody fragment comprises six complementarity-determining regions (CDRs), and wherein one of the CDRs comprises SEQ ID NO: 5. In some embodiments, the antibody or the antigen-binding antibody fragment comprises six CDRs, and wherein one of the CDRs comprises SEQ ID NO: 6. In some embodiments, the antibody or the antigen-binding antibody fragment comprises six CDRs, and wherein one of the CDRs comprises SEQ ID NO: 7. In some embodiments, the antibody or the antigen-binding antibody fragment comprises six CDRs, and wherein one of the CDRs comprises SEQ ID NO: 8.

The disclosure, in another aspect, provides a composition comprising an epitope and an adjuvant in a pharmaceutically acceptable carrier, wherein the epitope comprises an amino acid sequence of at least 20 amino acids from Zika virus (ZIKV) Envelope protein III (EDIII) comprising E162. In some embodiments, the epitope comprises an amino acid sequence of at least 5 amino acids, at least 10 amino acids, at least 15 amino acids, at least 25 amino acids, at least 30 amino acids, at least 35 amino acids, at least 40 amino acids, at least 45 amino acids, or at least 50 amino acids from ZIKV EDIII. In some embodiments, the epitope comprises an amino acid sequence of less than 40 amino acids, less than 35 amino acids, less than 30 amino acids, less than 25 amino acids, less than 24 amino acids, less than 23 amino acids, less than 22 amino acids, or less than 21 amino acids from ZIKV EDIII.

In some embodiments, the epitope comprises one or more amino acids from the lateral ridge of EDIII. In some embodiments, the epitope comprises 2, 3, 4, 5, 6, 7, 8, 9, 10, 11, 12, 13, 14, 15, 16, 17, 18, 19, 20 or more amino acids from the lateral ridge of EDIII. In some embodiments, the epitope comprises less than 20, 19, 18, 17, 16, 15, 14, 13, 12, 11, 10, 9, 8, 7, 6, 5, 4, 3, or 2 amino acids from the lateral ridge of EDIII.

In some embodiments, the epitope further comprises G182. In some embodiments, the epitope further comprises V364.

In some embodiments, the epitope comprises one or more amino acids from an EDI/EDIII linker region. In some embodiments, the epitope comprises 2, 3, 4, 5, 6, 7, 8, 9, 10, 11, 12, 13, 14, 15, 16, 17, 18, 19, 20 or more amino acids from an EDI/EDIII linker region. In some embodiments, the epitope comprises less than 20, 19, 18, 17, 16, 15, 14, 13, 12, 11, 10, 9, 8, 7, 6, 5, 4, 3, or 2 amino acids from an EDI/EDIII linker region.

In some embodiments, the epitope further comprises an amino acid variant relative to ZIKV EDIII and wherein the variant amino acid is not in E162, G182 or V364. In some embodiments, the epitope does not comprise any amino acids from EII.

Another aspect of the disclosure provides an epitope and an adjuvant in a pharmaceutically acceptable carrier, wherein the epitope comprises an amino acid sequence of at least 10 amino acids from Zika virus (ZIKV) Envelope protein III (EDIII) comprising E162. In some embodiments, the epitope comprises an amino acid sequence of at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 amino acids from EDIII. In some embodiments, the epitope comprises less than 20, 19, 18, 17, 16, 15, 14, 13, 12, 11, 10, 9, 8, 7, 6, 5, 4, 3, or 2 amino acids from EDIII.

An additional aspect of the disclosure provides a composition comprising an epitope and an adjuvant in a pharmaceutically acceptable carrier, wherein the epitope comprises an amino acid sequence of at least 10 amino acids from Zika virus (ZIKV) Envelope protein II (EDII) comprising R252. In some embodiments, the epitope comprises an amino acid sequence of at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 amino acids from EDII. In some embodiments, the epitope comprises less than 20, 19, 18, 17, 16, 15, 14, 13, 12, 11, 10, 9, 8, 7, 6, 5, 4, 3, or 2 amino acids from EDII.

In some embodiments, the epitope further comprises an amino acid variant relative to ZIKV EDIII and wherein the variant amino acid is not in R252. In some embodiments, the epitope does not comprise any amino acids from EIII.

Yet another aspect of the disclosure provides a composition comprising an antibody or an antigen-binding antibody fragment that specifically binds an epitope of a Zika virus (ZIKV) Envelope protein III (EDIII), and a pharmaceutically acceptable carrier. In some embodiments, the epitope is an epitope of any of the compositions described herein.

In another aspect, the disclosure provides a composition comprising an antibody or an antigen-binding antibody fragment that specifically binds an epitope of a Zika virus (ZIKV) Envelope protein III (EDIII), and a pharmaceutically acceptable carrier. In some embodiments, the epitope is an epitope of any of the compositions described herein.

In some embodiments, the antibody or an antigen-binding antibody fragment comprises a non-naturally occurring modification. In some embodiments, the antigen-binding antibody fragment is an scFv. In some embodiments, the antibody is a full-length antibody. In some embodiments, the full-length antibody is an IgG molecule.

In an additional aspect, the disclosure provides a method for vaccinating a subject against ZIKV comprising administering a composition of ZIKV antibodies, wherein the antibodies are quaternary epitope antibodies. In some embodiments, the composition is a composition described herein.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. The details of one or more embodiments of the invention are set forth in the accompanying Detailed Description, Examples, Claims, and Figures. Other features, objects, and advantages of the invention will be apparent from the description and from the claims.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 5A shows the fraction of total hits specific for Dengue virus (DENV) or ZIKV or cross reactive (left) and a table summarizing the FRNT50 values against 4 ZIKV strains and DENV4 (right). FIG. 5B shows binding of the indicated monoclonal antibodies to whole virus or recombinant proteins derived from ZIKV envelope (E) protein, which were determined by capture ELISA for whole virions or direct coating ELISA for recombinant proteins. FIG. 5C shows the results of microFRNT assays using Vero cells against the indicated viruses.

FIG. 19A shows plasma from four primary ZIKV cases (Dt168, 172, 206, and 244) tested for IgG binding to ZIKV (top) and DENV (bottom) over the dilution series indicated in the legend. The dotted horizontal line corresponds to the assay background average (average OD value for the negative control on each plate). FIG. 19B shows primary ZIKV plasma and primary ($1^o$) and secondary ($2^o$) control plasma tested for IgG binding to ZIKV recombinant E (ZIKV E80), DENV recombinant E (DENV E80), ZVEDI and ZVEDIII. FIG. 19C shows the results of neutralization assays performed for each primary ZIKV plasma as well as a secondary DENV control. NHS=normal human plasma, a negative binding control for ELISA.

FIG. 20A confirms the depletion of ZIKV E80-binding IgG in primary ZIKV plasma by direct antigen coating ELISA comparing ZIKV E80-binding IgG in depleted (gray bars) to MBP-control depleted (white bars) or undepleted (black bars) plasma. FIG. 20B shows IgG binding to ZIKV in depleted plasma tested by antigen capture ELISA. FIG. 20C shows FRNT assays performed for ZIKV E80-depleted plasma and controls against ZIKV H/PF/2013. FIG. 20D is a tabular summary of FRNT50 values for neutralization testing shown in FIG. 20C. FIG. 20E shows DT168 depleted of simple and quaternary E epitope-binding IgG with virus-like particle (VLP) antigen and then tested by FRNT assay as a positive control for the depletion methods described herein.

FIG. 22A shows an antigen capture ELISA for IgG binding performed for two candidate ZIKV mAbs and two control mAbs (C10, ZIKV and DENV neutralizing; 2D22, DENV2 neutralizing) against DENV (left) and ZIKV (right). FIG. 22B shows binding assessed to ZIKV E monomers and EDI and EDIII for each mAb. FIG. 22C presents competition assays (BOB) with a panel of mAbs having known binding specifies. The assays were performed to localize the epitopes of A9E and G9E.

FIGS. 23A-23C show escape mutants for A9E generated from PRVABC59. FIG. 23A shows the binding of the indicated mAb (left) and plasma (right) against A9E escape mutants from two independent experiments. FIG. 23B shows the neutralization of four A9E escape mutants from two independent experiments by the indicated mAb (top) and plasma (bottom). FIG. 23C shows a ZIKV E homodimer with escape mutations indicated. FIG. 23D shows the amino acid residues critical for A9E mAb and G9E Fab binding determined by alanine scanning shotgun mutagenesis. Plots show the binding of A9E and G9E vs. control mAbs. The data point in black corresponds to the alanine mutant that significantly reduces probe mAb binding compared to loading control mAbs. FIG. 23E shows the critical residues (gray spheres) discovered in the alanine mutagenesis mapping on a 3-dimensional model from ZIKV cryo-EM structure (PDB ID: 5IRE). The fusion loop of E domain II is labeled.

FIG. 24A shows a blockade of binding against A9E and G9E tested among plasma at a 1:20 dilution from ZIKV and DENV cases from the UNC Traveler's study, Nicaragua, and Sri Lanka as was performed for the mAbs in FIG. 22C. FIG. 24B shows the analysis when the ZIKV cases were sub-divided into primary (1°) and secondary (2°) ZIKV (ZIKV infection in a DENV-immune host). FIG. 24C shows paired plasma specimens from symptomatic ZIKV cases in Nicaragua analyzed by BOB at early (day 21 post symptom onset) versus late (6 months post symptom onset) convalescence. An unpaired Student's t-test was performed in FIGS. 24A and 24B; *, $p<0.001$; **, $P<0.0001$.

DETAILED DESCRIPTION OF THE INVENTION

Figure 1A:
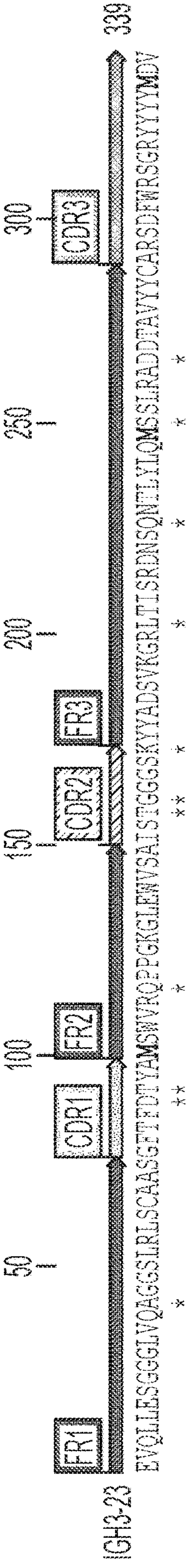
FIGS. 1A-1D show the isolation of the ultra-potent ZIKV-neutralizing antibody, A9E, using 6XL genetic reprogramming of memory B cells (MBCs). The antibody comprises IGHV3-23 and IGLV2-14 (lambda). The IgH (FIG. 1A; SEQ ID NO: 23) and IgL (FIG. 1B; SEQ ID NO: 24) $V_H$ sequences (* represents a somatic hypermutation) from a monoclonal MBC culture antibody, A9E, were cloned into an IgG1 expression vector and purified (FIG. 1C), and used in Vero-based neutralization assay against ZIKA/2015/Paraiba (FIG. 1D). The $EC_{50}$ was approximately 5-10 ng/mL.
Figure 1B:
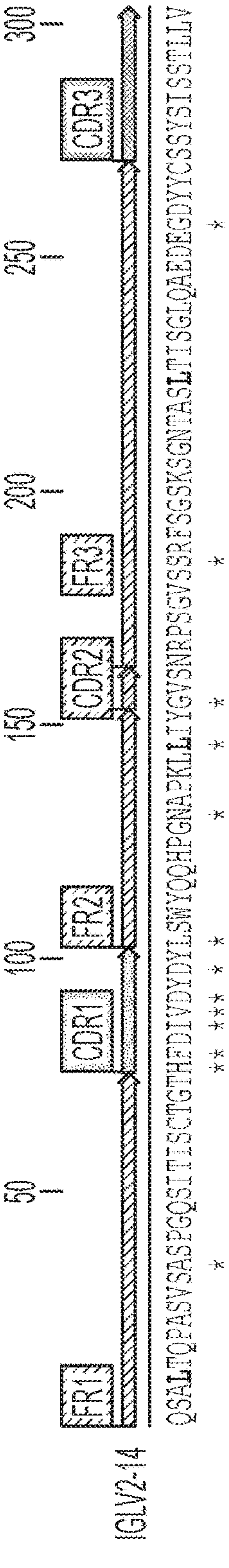
Figure 1C:
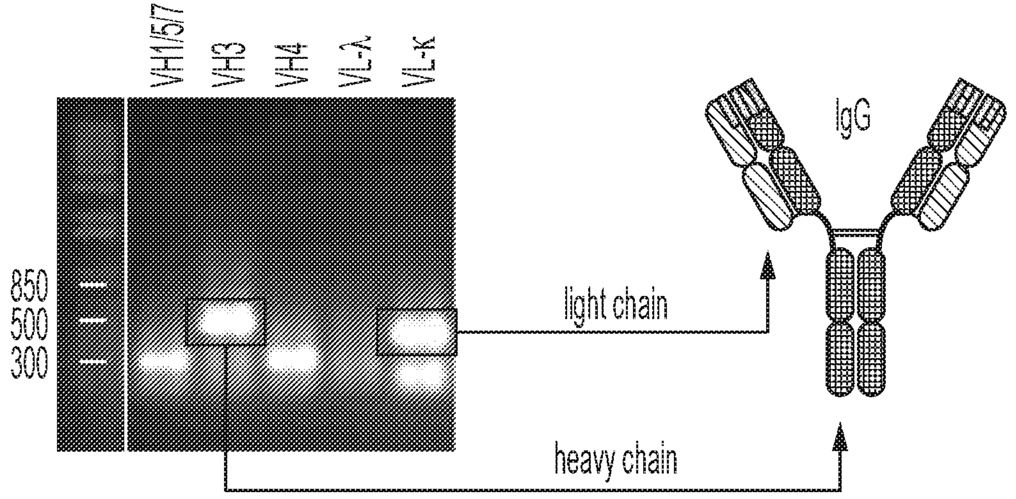
Figure 1D:
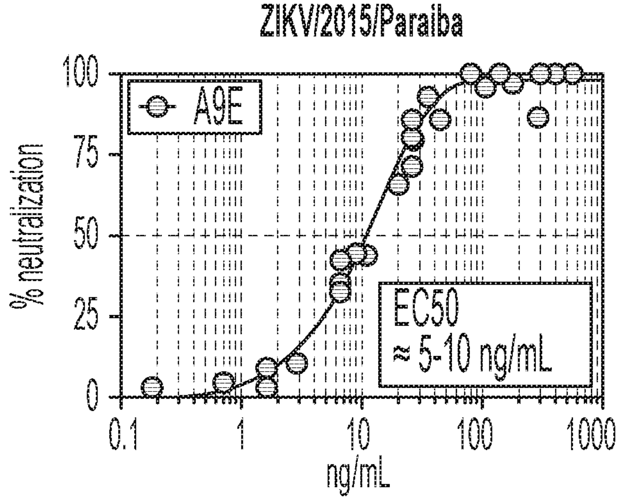

The recent Zika virus (ZIKV) epidemic in the Americas has revealed rare but serious manifestations of infection. ZIKV has emerged in regions endemic for dengue virus (DENV), a closely related mosquito-borne flavivirus. Cross-reactive antibodies confound studies of ZIKV epidemiology and pathogenesis. The immune responses to ZIKV may be different in people depending on their DENV immune status. As described herein, the human B cell and antibody response to ZIKV as a primary flavivirus infection can be used to define the properties of neutralizing and protective antibodies generated in the absence of pre-existing immunity to DENV. The plasma antibody and memory B cell response is highly ZIKV type-specific, and ZIKV neutralizing antibodies mainly target quaternary structure epitopes on the viral envelope. To map viral epitopes targeted by protective antibodies, two type-specific monoclonal antibodies (mAbs) from a ZIKV patient were isolated. As described herein, the tested mAbs were found to be strongly neutralizing in vitro and protective in vivo. The mAbs recognized distinct epitopes centered on domains I and II of the envelope protein.

Thus, provided herein are antibodies and antigen-binding fragments capable of binding to Zika virus (ZIKV), for example, binding to epitopes in the envelope (E) protein, such as envelope domain 1 (ED1). Such antibodies and antigen-binding fragments are capable of reducing or eliminating the biological activity of ZIKV. Accordingly, the antibodies and antigen-binding fragments described herein may be used to diagnose and/or treat subjects who have ZIKV.

The Zika positive-sense RNA genome comprises a single open reading frame encoding a polyprotein. The polyprotein is cleaved into three structural proteins (capsid, C, premembrane, prM, and envelope, E) which form the virus particle, and seven nonstructural (NS) proteins: NS1, NS2A, NS2B, NS3, NS4A, NS4B, and NS5. The nonstructural proteins are responsive for essential functions in genome replication, polyprotein cleavage, and the modulation of cellular processes. The E protein is a major target for neutralizing antibodies, as the protein is responsible for virus entry (Dai et al., Cell Host and Microbe, 19(5): 696-704 (2016)). In particular, the flavivirus E protein is a class II viral fusion protein that mediates attachment to cellular receptors and low-pH triggered fusion within endosomes required for viral entry into cells. The E protein monomer contains three distinct domains designated EDI, EDII, and EDIII (15). The surface of the flavivirus virion is covered by 90 E protein homodimers, which are tightly packed to form a viral envelope with icosahedral symmetry (16, 17). For DENV and West Nile virus, flaviviruses closely related to ZIKV, human neutralizing antibodies often target complex or quaternary epitopes, with antibody binding footprints that include residues on multiple adjacent E monomers on the intact virion (18-21).

Particularly for the four DENV serotypes, studies have demonstrated that humans exposed to primary flavivirus infections develop type-specific neutralizing antibodies and memory B cells (MBCs) that are strongly correlated with long-term protection from re-infection by the same virus (12, 22, 23). However, most ZIKV transmission occurs in areas where DENV (and potentially other flaviviruses) are endemic, with DENV seroprevalence as high as 90% by early adulthood (24, 25). Therefore, antibody cross-reactivity at the level of binding and neutralization occurs frequently among flaviviruses in general and between DENV and ZIKV in particular, which can confound serologic assays (26-29). Extensive cross-reactivity is expected given considerable conservation in amino acid sequence of DENV and ZIKV E (approximately 50%) (17, 33). Furthermore, B cell and antibody responses to a second DENV infection are skewed by preferential activation of pre-existing cross-reactive memory B cells. In fact, a similar phenomenon may occur when ZIKV infects a DENV-immune person (34-37). However, it has been observed that ZIKV type-specific antibody responses develop in humans even in the presence of immunity to prior DENV infection (35, 36, 38).

Thus, anti-ZIKV antibodies, especially those targeting the E protein domain and having low or no cross-reactivity to DENV, may be promising therapeutic agents for treating ZIKV. Accordingly, described herein are anti-ZIKV antibodies and therapeutic uses.

The present disclosure provides antibodies that bind Zika virus (ZIKV). In some instances, the antibodies described herein binds to an epitope in an envelope protein domain (ED) of ZIKV, e.g., ED1. The E protein, which is a dimer, comprises three distinct domains: a central β-barrel domain (ED1), an elongated finger-like structure (ED2), and a C-terminal immunoglobulin-like module (ED3). The ED1, which is folded into an eight-stranded β-barrel with an additional N-terminal $A_0$ strand, is further divided into three segments, while the ED2, which is responsible for the dimerization of the protein, comprises two distinct segments. The sequences of the envelope protein and its epitopes are provided below:

```
>YP_009430300.1 envelope protein E [Zika virus]
                                        (SEQ ID NO: 16)
IRCIGVSNRD FVEGMSGGTW VDVVLEHGGC VTVMAQDKPT

VDIELVTTTV SNMAEVRSYC YEASISDMAS DSRCPTQGEA
```

-continued

```
YLDKQSDTQY VCKRTLVDRG WGNGCGLFGK GSLVTCAKFA

CSKKMTGKSI QPENLEYRIM LSVHGSQHSG MIVNDTGHET

DENRAKVEIT PNSPRAEATL GGFGSLGLDC EPRTGLDFSD

LYYLTMNNKH WLVHKEWFHD IPLPWHAGAD TGTPHWNNKE

ALVEFKDAHA KRQTVVVLGS QEGAVHTALA GALEAEMDGA

KGRLSSGHLK CRLKMDKLRL KGVSYSLCTA AFTFTKIPAE

TLHGTVTVEV QYAGTDGPCK VPAQMAVDMQ TLTPVGRLIT

ANPVITESTE NSKMMLELDP PFGDSYIVIG VGEKKITHHW

HRSGSTIGKA FEATVRGAKR MAVLGDTAWD FGSVGGALNS

LGKGIHQIFG AAFKSLFGGM SWFSQILIGT LLMWLGLNTK

NGSISLMCLA LGGVLIFLST AVSA

ZIKA ED1:
Segment 1:
                                        (SEQ ID NO: 17)
IRCIGVSNRDFVEGMSGGTWVDVVLEHGGCVTVMAQDKPTVDIELVTTT

VS

Segment 2:
                                        (SEQ ID NO: 18)
PENLEYRIMLSVHGSQHSGMIVNDTGHETDENRAKVEITPNSPRAEATL

GGFGSLGLDCEP

Segment 3:
                                        (SEQ ID NO: 19)
AKGRLSSGHLKCRLKM

ZIKA ED2: 52-131, 193-279
Segment 1:
                                        (SEQ ID NO: 20)
NMAEVRSYCYEASISDMASDSRCPTQGEAYLDKQSDTQYVCKRTLVDRG

WGNGCGLFGKGSLVTCAKFACSKKMTGKSIQ

Segment 2:
                                        (SEQ ID NO: 21)
RTGLDFSDLYYLTMNNKHWLVHKEWFHDIPLPWHAGADTGTPHWNNKEA

LVEFKDAHAKRQTVVVLGSQEGAVHTALAGALEAEMDG

ZIKA ED3:
                                        (SEQ ID NO: 22)
DKLRLKGVSYSLCTAAFTFTKIPAETLHGTVTVEVQYAGTDGPCKVPAQ

MAVDMQTLTPVGRLITANPVITESTENSKMMLELDPPFGDSYIVIGVGE

KKITHHWHRS
```

There are a number of ZIKV strains that have been isolated. For example, NCBI GenBank Accession No. AHZ13508.1, given below, provides a full-length ZIKV isolated from a French Polynesia outbreak in 2013. ZIKV polypeptides from other sources are known in the art and can be obtained from publicly available gene databases, for example, GenBank.

```
AHZ13508.1 polyprotein [Zika virus]
                                        (SEQ ID NO: 13)
MKNPKKKSGGFRIVNMLKRGVARVSPFGGLKRLPAGLLLGHGPIRMVLAILAFLRFTAIKPSLGLINRWG

SVGKKEAMEIIKKFKKDLAAMLRIINARKEKKRRGADTSVGIVGLLLTTAMAAEVTRRGSAYYMYLDRND

AGEAISFPTTLGMNKCYIQIMDLGHMCDATMSYECPMLDEGVEPDDVDCWCNTTSTWVVYGTCHHKKGEA
```

-continued

RRSRRAVTLPSHSTRKLQTRSQTWLESREYTKHLIRVENWIFRNPGFALAAAAIAWLLGSSTSQKVIYLV

MILLIAPAYSIRCIGVSNRDFVEGMSGGTWVDVVLEHGGCVTVMAQDKPTVDIELVTTTVSNMAEVRSYC

YEASISDMASDSRCPTQGFAYLDKQSDTQYVCKRTLVDRGWGNGCGLEGKGSLVTCAKFACSKKMTGKSI

QPENLEYRIMLSVHGSQHSGMIVNDTGHETDENRAKVEITPNSPRAEATLGGFGSLGLDCEPRTGLDFSD

LYYLTMNNKHWLVHKEWFHDIPLPWHAGADTGTPHWNNKEALVEFKDAHAKRQTVVVLGSQEGAVHTALA

GALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKA

FEATVRGAKRMAVLGDTAWDFGSVGGALNSLGKGIHQIFGAAFKSLFGGMSWFSQILIGTLLMWLGLNTK

NGSISLMCLALGGVLIFLSTAVSADVGCSVDFSKKETRCGTGVFVYNDVEAWRDRYKYHPDSPRRLAAAV

KQAWEDGICGISSVSRMENIMWRSVEGELNAILEENGVQLTVVVGSVKNPMWRGPQRLPVPVNELPHGWK

AWGKSYFVRAAKTNNSFVVDGDTLKECPLKHRAWNSFLVEDHGFGVFHTSVWLKVREDYSLECDPAVIGT

AVKGKEAVHSDLGYWIESEKNDTWRLKRAHLIEMKTCEWPKSHTLWTDGIEESDLIIPKSLAGPLSHHNT

REGYRTQMKGPWHSEELEIRFEECPGTKVHVEETCGTRGPSLRSTTASGRVIEEWCCRECTMPPLSFRAK

DGCWYGMEIRPRKEPESNLVRSMVTAGSTDHMDHFSLGVLVILLMVQEGLKKRMTTKIIISTSMAVLVAM

ILGGFSMSDLAKLAILMGATFAEMNTGGDVAHLALIAAFKVRPALLVSFIFRANWTPRESMLLALASCLL

QTAISALEGDLMVLINGFALAWLAIRAMVVPRTDNITLAILAALTPLARGTLLVAWRAGLATCGGFMLLS

LKGKGSVKKNLPFVMALGLTAVRLVDPINVVGLLLLTRSGKRSWPPSEVLTAVGLICALAGGFAKADIEM

AGPMAAVGLLIVSYVVSGKSVDMYIERAGDITWEKDAEVTGNSPRLDVALDESGDFSLVEDDGPPMREII

LKVVLMTICGMNPIAIPFAAGAWYVYVKTGKRSGALWDVPAPKEVKKGETTDGVYRVMTRRLLGSTQVGV

GVMQEGVEHTMWHVTKGSALRSGEGRLDPYWGDVKQDLVSYCGPWKLDAAWDGHSEVQLLAVPPGERARN

IQTLPGIFKTKDGDIGAVALDYPAGTSGSPILDKCGRVIGLYGNGVVIKNGSYVSAITQGRREEETPVEC

FEPSMLKKKQLTVLDLHPGAGKTRRVLPEIVREAIKTRLRTVILAPTRVVAAEMEEALRGLPVRYMTTAV

NVTHSGTEIVDLMCHATFTSRLLQPIRVPNYNLYIMDEAHFTDPSSIAARGYISTRVEMGEAAAIFMTAT

PPGTRDAFPDSNSPIMDTEVEVPERAWSSGFDWVTDHSGKTVWFVPSVRNGNEIAACLTKAGKRVIQLSR

KTFETEFQKTKHQEWDFVVTTDISEMGANFKADRVIDSRRCLKPVILDGERVILAGPMPVTHASAAQRRG

RIGRNPNKPGDEYLYGGGCAETDEDHAHWLEARMLLDNIYLQDGLIASLYRPEADKVAAIEGEFKLRTEQ

RKTFVELMKRGDLPVWLAYQVASAGITYTDRRWCFDGTTNNTIMEDSVPAEVWTRHGEKRVLKPRWMDAR

VCSDHAALKSFKEFAAGKRGAAFGVMEALGTLPGHMTERFQEAIDNLAVLMRAETGSRPYKAAAAQLPET

LETIMLLGLLGTVSLGIFFVLMRNKGIGKMGFGMVTLGASAWLMWLSEIEPARIACVLIVVFLLLVVLIP

EPEKQRSPQDNQMAIIIMVAVGLLGLITANELGWLERTKSDLSHLMGRREEGATIGFSMDIDLRPASAWA

IYAALTTFITPAVQHAVTTSYNNYSLMAMATQAGVLFGMGKGMPFYAWDEGVPLLMIGCYSQLTPLTLIV

AIILLVAHYMYLIPGLQAAAARAAQKRTAAGIMKNPVVDGIVVTDIDTMTIDPQVEKKMGQVLLIAVAVS

SAILSRTAWGWGEAGALITAATSTLWEGSPNKYWNSSTATSLCNIFRGSYLAGASLIYTVTRNAGLVKRR

GGGTGETLGEKWKARLNQMSALEFYSYKKSGITEVCREEARRALKDGVATGGHAVSRGSAKLRWLVERGY

LQPYGKVIDLGCGRGGWSYYAATIRKVQEVKGYTKGGPGHEEPMLVQSYGWNIVRLKSGVDVFHMAAEPC

DTLLCDIGESSSSPEVEEARTLRVLSMVGDWLEKRPGAFCIKVLCPYTSTMMETLERLQRRYGGGLVRVP

LSRNSTHEMYWVSGAKSNTIKSVSTTSQLLLGRMDGPRRPVKYEEDVNLGSGTRAVVSCAEAPNMKIIGN

RIERIRSEHAETWFFDENHPYRTWAYHGSYEAPTQGSASSLINGVVRLLSKPWDVVTGVTGIAMTDTTPY

GQQRVFKEKVDTRVPDPQEGTRQVMSMVSSWLWKELGKHKRPRVCTKEEFINKVRSNAALGAIFEEEKEW

KTAVEAVNDPRFWALVDKEREHHLRGECQSCVYNMMGKREKKQGEFGKAKGSRAIWYMWLGARFLEFEAL

-continued

GFLNEDHWMGRENSGGGVEGLGLQRLGYVLEEMSRIPGGRMYADDTAGWDTRISRFDLENEALITNQMEK

GHRALALAIIKYTYQNKVVKVLRPAEKGKTVMDIISRQDQRGSGQVVTYALNTFTNLVVQLIRNMEAEEV

LEMQDLWLLRRSEKVTNWLQSNGWDRLKRMAVSGDDCVVKPIDDRFAHALRFLNDMGKVRKDTQEWKPST

GWDNWEEVPFCSHHFNKLHLKDGRSIVVPCRHQDELIGRARVSPGAGWSIRETACLAKSYAQMWQLLYFH

RRDLRLMANAICSSVPVDWVPTGRTTWSIHGKGEWMTTEDMLVVWNRVWIEENDHMEDKTPVTKWTDIPY

LGKREDLWCGSLIGHRPRTTWAENIKNTVNMVRRIIGDEEKYMDYLSTQVRYLGEEGSTPGVL

AAV34151.1 polyprotein [Zika virus]-MR 766 Strain (SEQ ID NO: 15)

MKNPKEEIRRIRIVNMLKRGVARVNPLGGLKRLPAGLLLGHGPIRMVLAILAFLRFTAIKPSLGLINRWG

SVGKKEAMEIIKKFKKDLAAMLRIINARKERKRRGADTSIGIIGLLLTTAMAAEITRRGSAYYMYLDRSD

AGKAISFATTLGVNKCHVQIMDLGHMCDATMSYECPMLDEGVEPDDVDCWCNTTSTWVVYGTCHHKKGEA

RRSRRAVTLPSHSTRKLQTRSQTWLESREYTKHLIKVENWIFRNPGFALVAVAIAWLLGSSTSQKVIYLV

MILLIAPAYSIRCIGVSNRDFVEGMSGGTWVDVVLEHGGCVTVMAQDKPTVDIELVTTTVSNMAEVRSYC

YEASTSDMASDSRCPTQGEAYLDKQSDTQYVCKRTLVDRGWGNGCGLFGKGSLVTCAKFTCSKKMTGKSI

QPENLEYRIMLSVHGSQHSGMIGYETDEDRAKVEVTPNSPRAEATLGGFGSLGLDCEPRTGLDFSDLYYL

TMNNKHWLVHKEWFHDIPLPWHAGADTGTPHWNNKEALVEFKDAHAKRQTVVVLGSQEGAVHTALAGALE

AEMDGAKGRLFSGHLKCRLKMDKLRLKGVSYSLCTAAFTFTKVPAETLHGTVTVEVQYAGTDGPCKIPVQ

MAVDMQTLTPVGRLITANPVITESTENSKMMLELDPPFGDSYIVIGVGDKKITHHWHRSGSTIGKAFEAT

VRGAKRMAVLGDTAWDEGSVGGVENSLGKGIHQIFGAAFKSLEGGMSWESQILIGTLLVWLGLNTKNGSI

SLTCLALGGVMIFLSTAVSADVGCSVDFSKKETRCGTGVFIYNDVEAWRDRYKYHPDSPRRLAAAVKQAW

EEGICGISSVSRMENIMWKSVEGELNAILEENGVQLTVVVGSVKNPMWRGPQRLPVPVNELPHGWKAWGK

SYFVRAAKTNNSFVVDGDTLKECPLEHRAWNSFLVEDHGEGVEHTSVWLKVREDYSLECDPAVIGTAVKG

REAAHSDLGYWIESEKNDTWRLKRAHLIEMKTCEWPKSHTLWTDGVEESDLIIPKSLAGPLSHHNTREGY

RTQVKGPWHSEELEIRFEECPGTKVYVEETCGTRGPSLRSTTASGRVIEEWCCRECTMPPLSFRAKDGCW

YGMEIRPRKEPESNLVRSMVTAGSTDHMDHFSLGVLVILLMVQEGLKKRMTTKIIMSTSMAVLVVMILGG

FSMSDLAKLVILMGATFAEMNTGGDVAHLALVAAFKVRPALLVSFIFRANWTPRESMLLALASCLLQTAI

SALEGDLMVLINGFALAWLAIRAMAVPRTDNIALPILAALTPLARGTLLVAWRAGLATCGGIMLLSLKGK

GSVKKNLPFVMALGLTAVRVVDPINVVGLLLLTRSGKRSWPPSEVLTAVGLICALAGGFAKADIEMAGPM

AAVGLLIVSYVVSGKSVDMYIERAGDITWEKDAEVTGNSPRLDVALDESGDFSLVEEDGPPMREIILKVV

LMAICGMNPIAIPFAAGAWYVYVKTGKRSGALWDVPAPKEVKKGETTDGVYRVMTRRLLGSTQVGVGVMQ

EGVFHTMWHVTKGAALRSGEGRLDPYWGDVKQDLVSYCGPWKLDAAWDGLSEVQLLAVPPGERARNIQTL

PGIFKTKDGDIGAVALDYPAGTSGSPILDKCGRVIGLYGNGVVIKNGSYVSAITQGKREEETPVECFEPS

MLKKKQLTVLDLHPGAGKTRRVLPEIVREAIKKRLRTVILAPTRVVAAEMEEALRGLPVRYMTTAVNVTH

SGTEIVDLMCHATFTSRLLQPIRVPNYNLNIMDEAHFTDPSSIAARGYISTRVEMGEAAAIFMTATPPGT

RDAFPDSNSPIMDTEVEVPERAWSSGFDWVTDHSGKTVWFVPSVRNGNEIAACLTKAGKRVIQLSRKTFE

TEFQKTKNQEWDFVITTDISEMGANFKADRVIDSRRCLKPVILDGERVILAGPMPVTHASAAQRRGRIGR

NPNKPGDEYMYGGGCAETDEGHAHWLEARMLLDNIYLQDGLIASLYRPEADKVAAIEGEFKLRTEQRKTF

VELMKRGDLPVWLAYQVASAGITYTDRRWCFDGTTNNTIMEDSVPAEVWTKYGEKRVLKPRWMDARVCSD

HAALKSFKEFAAGKRGAALGVMEALGTLPGHMTERFQEAIDNLAVLMRAETGSRPYKAAAAQLPETLETI

MLLGLLGTVSLGIFFVLMRNKGIGKMGFGMVTLGASAWLMWLSEIEPARIACVLIVVFLLLVVLIPEPEK

QRSPQDNQMAIIIMVAVGLLGLITANELGWLERTKNDIAHLMGRREEGATMGFSMDIDLRPASAWAIYAA

LTTLITPAVQHAVTTSYNNYSLMAMATQAGVLFGMGKGMPFMHGDLGVPLLMMGCYSQLTPLTLIVAIIL

-continued

```
LVAHYMYLIPGLQAAAARAAQKRTAAGIMKNPVVDGIVVTDIDTMTIDPQVEKKMGQVLLIAVAISSAVL

LRTAWGWGEAGALITAATSTLWEGSPNKYWNSSTATSLCNIFRGSYLAGASLIYTVTRNAGLVKRRGGGT

GETLGEKWKARLNQMSALEFYSYKKSGITEVCREEARRALKDGVATGGHAVSRGSAKIRWLEERGYLQPY

GKVVDLGCGRGGWSYYAATIRKVQEVRGYTKGGPGHEEPMLVQSYGWNIVRLKSGVDVFHMAAEPCDTLL

CDIGESSSSPEVEETRTLRVLSMVGDWLEKRPGAFCIKVLCPYTSTMMETMERLQRRHGGGLVRVPLCRN

STHEMYWVSGAKSNIIKSVSTTSQLLLGRMDGPRRPVKYEEDVNLGSGTRAVASCAEAPNMKIIGRRIER

IRNEHAETWELDENHPYRTWAYHGSYEAPTQGSASSLVNGVVRLLSKPWDVVTGVTGIAMTDTTPYGQQR

VFKEKVDTRVPDPQEGTRQVMNIVSSWLWKELGKRKRPRVCTKEEFINKVRSNAALGAIFEEEKEWKTAV

EAVNDPRFWALVDREREHHLRGECHSCVYNMMGKREKKQGEFGKAKGSRAIWYMWLGARFLEFEALGFLN

EDHWMGRENSGGGVEGLGLQRLGYILEEMNRAPGGKMYADDTAGWDTRISKFDLENEALITNQMEEGHRT

LALAVIKYTYQNKVVKVLRPAEGGKTVMDIISRQDQRGSGQVVTYALNTFTNLVVQLIRNMEAEEVLEMQ

DLWLLRKPEKVTRWLQSNGWDRLKRMAVSGDDCVVKPIDDRFAHALRFLNDMGKVRKDTQEWKPSTGWSN

WEEVPFCSHHFNKLYLKDGRSIVVPCRHQDELIGRARVSPGAGWSIRETACLAKSYAQMWQLLYFHRRDL

RLMANAICSAVPVDWVPTGRTTWSIHGKGEWMTTEDMLMVWNRVWIEENDHMEDKTPVTKWTDIPYLGKR

EDLWCGSLIGHRPRTTWAENIKDTVNMVRRIIGDEEKYMDYLSTQVRYLGEEGSTPGVL
```

The antibodies described herein bind ZIKV or a fragment thereof (e.g., a segment of ED1). As used herein, the term "anti-ZIKV antibody" refers to any antibody capable of binding to a ZIKV polypeptide. In some instances, the anti-ZIKV antibody can suppress the 15 bioactivity of ZIKV. In another instance, the anti-ZIKV antibody does not neutralize Dengue viruses (DENV) 1-4. As used herein, "neutralize" means to reduce or eliminate the biological activity of an infectious agent (e.g., a virus). Neutralization may be measured, for example, with a Vero cell neutralization test, which determines the percent neutralization of an infectious agent (e.g., a virus) over a range of antibody or antigen-binding antibody fragment concentrations. Antibody or antigen-binding antibody fragments may, for example, block 50-100% of an infectious agent's biological activity. In contrast, antibodies or antigen-binding antibody fragments that do not neutralize the biological activity of an infectious agent may block 0-20% of the infectious agent's biological activity.

In another instance, the anti-ZIKV antibody may be used in research or in diagnostic/prognostic methods, e.g., for the detection of ZIKV, for example, to determine treatment eligibility and efficacy. Alternatively, or in addition, the anti-ZIKV antibodies provided herein may be used to treat ZIKV infections in a subject in need thereof.

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', F(ab')2, Fv), single chain (scFv), mutants thereof, fusion proteins comprising an antibody portion, humanized antibodies, chimeric antibodies, diabodies, nanobodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

A typical antibody molecule comprises a heavy chain variable region ($V_H$) and a light chain variable region ($V_L$), which are usually involved in antigen binding. The $V_H$ and $V_L$ regions can be further subdivided into regions of hypervariability, also known as "complementarity determining regions" ("CDR"), interspersed with regions that are more conserved, which are known as "framework regions" ("FR"). Each $V_H$ and $V_L$ is typically composed of three CDRs and four FRs, arranged from amino-terminus to carboxy-terminus in the following order: FR1, CDR1, FR2, CDR2, FR3, CDR3, FR4. The extent of the framework region and CDRs can be precisely identified using methodology known in the art, for example, by the Kabat definition, the Chothia definition, the IMGT definition the AbM definition, and/or the contact definition, all of which are well known in the art. See, e.g., Kabat, E. A., et al. (1991) *Sequences of Proteins of Immunological Interest, Fifth Edition*, U.S. Department of Health and Human Services, NIH Publication No. 91-3242, Chothia et al., (1989) Nature 342:877; Chothia, C. et al. (1987) J. Mol. Biol. 196:901-917, Al-lazikani et al (1997) J. Molec. Biol. 273:927-948; Ye et al., Nucleic Acids Res., 2013, 41:W34-40, and Almagro, J. Mol. Recognit. 17:132-143 (2004). See also hgmp.mrc.ac.uk and bioinf.org.uk/abs).

The anti-ZIKV antibody described herein may be a full-length antibody, which contains two heavy chains and two light chains, each including a variable domain and a constant domain. Alternatively, the anti-ZIKV antibody can be an antigen-binding fragment of a full-length antibody. Examples of binding fragments encompassed within the term "antigen-binding fragment" of a full length antibody include (i) a Fab fragment, a monovalent fragment consisting of the $V_L$, $V_H$, $C_L$ and $C_H1$ domains; (ii) a $F(ab')_2$ fragment, a bivalent fragment including two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR) that retains functionality. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules known as single chain Fv (scFv). See e.g., Bird et al. (1988) *Science* 242:423-426; and Huston et al. (1988) *Proc. Natl. Acad. Sci. USA* 85:5879-5883.

In some embodiments, the anti-ZIKV antibody as described herein can bind and inhibit the biological activity of ZIKV by at least 50% (e.g., 60%, 70%, 80%, 90%, 95% or greater). The apparent inhibition constant ($Ki^{app}$ or $K_{i,app}$), which provides a measure of inhibitor potency, is related to the concentration of inhibitor required to reduce enzyme activity and is not dependent on enzyme concentrations. The inhibitory activity of an anti-ZIKV antibody described herein can be determined by routine methods known in the art.

The $K_i^{app}$ value of an antibody may be determined by measuring the inhibitory effect of different concentrations of the antibody on the extent of the reaction (e.g., enzyme activity); fitting the change in pseudo-first order rate constant (v) as a function of inhibitor concentration to the modified Morrison equation (Equation 1) yields an estimate of the apparent Ki value. For a competitive inhibitor, the $Ki^{app}$ can be obtained from the y-intercept extracted from a linear regression analysis of a plot of $K_i^{app}$ versus substrate concentration.

$$v = A \cdot \frac{([E] - [I] - K_i^{app}) + \sqrt{([E] - [I] - K_i^{app})^2 + 4[E] \cdot K_i^{app}}}{2} \quad \text{(Equation 1)}$$

Where A is equivalent to $v_o/E$, the initial velocity ($v_o$) of the enzymatic reaction in the absence of inhibitor (I) divided by the total enzyme concentration (E).

In some embodiments, the anti-ZIKV antibody described herein may have a $Ki^{app}$ value of 1000, 900, 800, 700, 600, 500, 400, 300, 200, 100, 50, 40, 30, 20, 19, 18, 17, 16, 15, 14, 13, 12, 11, 10, 9, 8, 7, 6, 5 pM or less for the target antigen or antigen epitope. In some embodiments, the anti-ZIKV antibody may have a lower $Ki^{app}$ for a first target (e.g., the ED1 of ZIKV) relative to a second target (e.g., the ED2 of ZIKV). Differences in $Ki^{app}$(e.g., for specificity or other comparisons) can be at least 1.5, 2, 3, 4, 5, 10, 15, 20, 37.5, 50, 70, 80, 91, 100, 500, 1000, 10,000 or $10^5$ fold. In some examples, the anti-ZIKV antibody inhibits a first antigen (e.g., a first protein in a first conformation or mimic thereof) better relative to a second antigen (e.g., the same first protein in a second conformation or mimic thereof; or a second protein). In some embodiments, any of the anti-ZIKV antibodies may be further affinity matured to reduce the $Ki^{app}$ of the antibody to the target antigen or antigenic epitope thereof.

The antibodies described herein can be murine, rat, human, or any other origin (including chimeric or humanized antibodies). Such antibodies are non-naturally occurring, i.e., would not be produced in an animal without human act (e.g., immunizing such an animal with a desired antigen or fragment thereof or isolated from antibody libraries).

Any of the antibodies described herein can be either monoclonal or polyclonal. A "monoclonal antibody" refers to a homogenous antibody population and a "polyclonal antibody" refers to a heterogeneous antibody population. These two terms do not limit the source of an antibody or the manner in which it is made.

In one example, the antibody used in the methods described herein is a humanized antibody. Humanized antibodies refer to forms of non-human (e.g., murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a CDR of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, or six) which are altered with respect to the original antibody, which are also termed one or more CDRs "derived from" one or more CDRs from the original antibody. Humanized antibodies may also involve affinity maturation.

Methods for constructing humanized antibodies are also well known in the art. See, e.g., Queen et al., Proc. Natl. Acad. Sci. USA, 86:10029-10033 (1989). In one example, variable regions of $V_H$ and $V_L$ of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human $V_H$ and $V_L$ chains having amino acid sequences that are homologous to those of the parent non-human antibody are identified from any antibody gene database using the parent $V_H$ and $V_L$ sequences as search queries. Human $V_H$ and $V_L$ acceptor genes are then selected.

The CDR regions within the selected human acceptor genes can be replaced with the CDR regions from the parent non-human antibody or functional variants thereof. When necessary, residues within the framework regions of the parent chain that are predicted to be important in interacting with the CDR regions can be used to substitute for the corresponding residues in the human acceptor genes.

In another example, the antibody described herein is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region. Modifications can include naturally occurring amino acids and non-naturally occurring amino acids. Examples of non-naturally occurring amino acids are modifications that are not isotypic and can be found in U.S. Pat. No. 6,586,207; WO 98/48032; WO 03/073238; US2004-0214988A1; WO 05/35727A2; WO 05/74524A2; J. W. Chin et al., (2002), Journal of the American Chemical Society 124:9026-9027; J. W. Chin, & P. G. Schultz, (2002), ChemBioChem 11:1135-1137; J. W. Chin, et al., (2002), PICAS United States of America 99:11020-11024; and, L. Wang, & P. G. Schultz, (2002), Chem. 1-10, each of which is incorporated by reference herein in its entirety.

In some embodiments, the anti-ZIKV antibodies described herein specifically bind to the corresponding target antigen or an epitope thereof. An antibody that "specifically binds" to an antigen or an epitope is a term well understood in the art. A molecule is said to exhibit "specific binding" if it reacts more frequently, more rapidly, with greater duration and/or with greater affinity with a particular target antigen than it does with alternative targets. An antibody "specifically binds" to a target antigen or epitope if it binds with greater affinity, avidity, more readily, and/or with greater duration than it binds to other substances. For example, an antibody that specifically (or preferentially) binds to an antigen (ZIKV) or an antigenic epitope (e.g., ED1) therein is an antibody that binds this target antigen with greater affinity, avidity, more readily, and/or with greater duration than it binds to other antigens or other epitopes in the same antigen. It is also understood with this definition that, for example, an antibody that specifically binds to a first target antigen may or may not specifically or preferentially bind to a second target antigen. As such, "specific binding" or "preferential binding" does not necessarily require (although it can include) exclusive binding. In some examples, an antibody that "specifically binds" to a target antigen or an epitope thereof may not bind to other antigens or other epitopes in the same antigen (i.e., only baseline binding activity can be detected in a conventional method). In some embodiments, the antibodies described herein specifically bind to the ED1 of ZIKV. Alternatively, or in addition, the anti-ZIKV antibody described herein may specifically bind ZIKV or a fragment thereof as relative to Dengue viruses (DENV) 1-4 (e.g., having a binding affinity at least 10-fold higher to one antigen than the other as determined in the same assay under the same assay conditions).

In some embodiments, an anti-ZIKV antibody as described herein has a suitable binding affinity for the target antigen (e.g., ZIKV) or antigenic epitopes thereof. As used herein, "binding affinity" refers to the apparent association constant or $K_A$. The $K_A$ is the reciprocal of the dissociation constant ($K_D$). The anti-ZIKV antibodies described herein may have a binding affinity ($K_D$) of at least $10^{-5}$, $10^{-6}$, $10^{-7}$, $10^{-8}$, $10^{-9}$, $10^{-10}$ M, or lower for the target antigen or antigenic epitope. An increased binding affinity corresponds to a decreased $K_D$. Higher affinity binding of an antibody for a first antigen relative to a second antigen can be indicated by a higher $K_A$ (or a smaller numerical value $K_D$) for binding the first antigen than the $K_A$ (or numerical value $K_D$) for binding the second antigen. In such cases, the antibody has specificity for the first antigen (e.g., a first protein in a first conformation or mimic thereof) relative to the second antigen (e.g., the same first protein in a second conformation or mimic thereof; or a second protein). In some embodiments, the anti-ZIKV antibodies described herein have a higher binding affinity (a higher $K_A$ or smaller $K_D$) to the ED1 of ZIKV as compared to the binding affinity to the ED2 of ZIKV. Differences in binding affinity (e.g., for specificity or other comparisons) can be at least 1.5, 2, 3, 4, 5, 10, 15, 20, 37.5, 50, 70, 80, 91, 100, 500, 1000, 10,000 or $10^5$ fold. In some embodiments, any of the anti-ZIKV antibodies may be further affinity matured to increase the binding affinity of the antibody to the target antigen or antigenic epitope thereof.

Binding affinity (or binding specificity) can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in HBS-P buffer (10 mM HEPES pH7.4, 150 mM NaCl, 0.005% (v/v) Surfactant P20). These techniques can be used to measure the concentration of bound binding protein as a function of target protein concentration. The concentration of bound binding protein ([Bound]) is generally related to the concentration of free target protein ([Free]) by the following equation:

$$[\text{Bound}]=[\text{Free}]/(Kd+[\text{Free}])$$

It is not always necessary to make an exact determination of $K_A$, though, since sometimes it is sufficient to obtain a quantitative measurement of affinity, e.g., determined using a method such as ELISA or FACS analysis, is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

Two exemplary anti-ZIKV antibodies are provided below (CDR residues based on IGMT numbering are indicated by bolding):

Anti-ZIKV clone DT168(A)-D1_A-9E (A9E):

$V_H$:

(SEQ ID NO: 1)

EVQLLESGGGLVQAGGSLRLSCAASGFTFDTYAMSWVRQPPGKGLEW

VSAISTGGGSKYYADSVKGRLTISRDNSQNTLYLQMSSLRADDTAVY

YCARSDFWRSGRYYYYMDVWGRGTTVTVSS

CDR3:

(SEQ ID NO: 5)

ARSDFWRSGRYYYYMDV

-continued $V_L$:

(SEQ ID NO: 2)

QSALTQPASVSASPGQSITISCTGTHFDIVDYDYLSWYQQHPGNAPK

LLIYGVSNRPSGVSSRFSGSKSGNTASLTISGLQAEDEGDYYCSSYS

ISSTLLVFGGGTKLSV

CDR3:

(SEQ ID NO: 6)

SSYSISSTLLV

Nucleotide Sequences:

$V_H$:

(SEQ ID NO: 9)

GAGGTGCAGCTGTTGGAGTCTGGGGGAGGCTTGGTTCAGGCGGGGGG

GTCCCTGAGACTCTCCTGTGCAGCCTCTGGATTCACCTTTGACACCT

ATGCCATGAGTTGGGTCCGCCAGCCTCCAGGGAAGGGGCTGGAGTGG

GTCTCCGCTATTAGCACTGGTGGTGGCAGCAAATACTACGCAGACTC

CGTAAAGGGCCGGCTCACCATCTCCAGAGACAATTCCCAGAACACGC

TGTATCTGCAGATGAGCAGCCTGAGAGCCGACGACACGGCCGTATAT

TACTGTGCGAGGTCCGATTTTTGGAGGAGTGGTCGTTATTACTACTA

CATGGACGTCTGGGGCAGAGGGACCACGGTCACCGTCTCCTCA $V_L$:

(SEQ ID NO: 10)

CAGTCTGCCCTGACTCAGCCTGCCTCCGTGTCTGCGTCCCCTGGACA

ATCGATCACCATCTCCTGCACTGGAACCCACTTTGACATTGTTGATT

ATGACTATCTCTCCTGGTACCAACAACACCCAGGCAACGCCCCCAAA

CTCCTGATTTATGGTGTCAGTAATCGGCCCTCAGGGGTCTCAAGTCG

CTTCTCTGGTTCCAAGTCTGGCAACACGGCCTCCCTGACCATCTCTG

GGCTCCAGGCTGAGGACGAGGGTGATTATTATTGCAGCTCCTATTCA

ATCTCCAGCACTCTCCTAGTTTTCGGCGGAGGGACGAAGCTGTCCGT

C

Anti-ZIKV clone DT168(A)-D1_G-9E (G9E):

$V_H$:

(SEQ ID NO: 3)

EVQLVESGGGVVQPGRSLRLSCVASGFAFSNYHMHWVRQAPGKGLEW

VAIIWDDGSDQYYADSVKGRFTISRDNSKNTLFLQMNRLRAEDTALY

YCVGGSSAYNGDNGWREAASLDDWGQGTLVTVSS

CDR3:

(SEQ ID NO: 7)

VGGSSAYNGDNGWREAASLDD $V_L$:

(SEQ ID NO: 4)

QSALTQPASVSGSPGQSITIFCSGSSNDVGGYNYVSWYQQYPGKVPK

LLIYDVNSRPSGVSNRFSGSKSGNTASLTISGLQAEDEADYYCSSYT

SRRTWVFGGGTIVTVL

CDR3:

(SEQ ID NO: 8)

SSYTSRRTWV

Nucleotide Sequences:

$V_H$:

(SEQ ID NO: 11)

GAGGTGCAGCTGGTGGAGTCTGGGGGAGGCGTGGTCCAGCCTGGGAG

GTCCCTTAGACTCTCCTGTGTAGCATCTGGATTCGCCTTCAGTAACT

ATCACATGCACTGGGTCCGCCAGGCTCCAGGCAAGGGGCTGGAGTGG

GTGGCAATTATCTGGGATGATGGAAGTGATCAATATTATGCAGACTC

CGTGAAGGGCCGATTCACCATCTCCAGAGACAATTCCAAGAACACAT

TGTTTCTGCAAATGAACAGACTGAGAGCCGAGGACACGGCTCTCTAT

TACTGTGTGGGAGGATCCTCTGCCTATAACGGTGACAACGGTTGGCG

GGAAGCTGCGAGCCTGGACGACTGGGGCCAGGGAACCCTGGTCACCG

TCTCCTCA $V_L$:

(SEQ ID NO: 12)

CAGTCTGCCCTGACTCAGCCTGCCTCCGTGTCTGGGTCTCCTGGACA

ATCGATCACCATTTTCTGCAGTGGAAGCAGCAATGACGTTGGAGGTT

ATAATTATGTCTCCTGGTACCAGCAATACCCAGGCAAAGTCCCCAAA

CTCCTGATTTATGATGTCAATAGTCGGCCCTCAGGGGTTTCTAATCG

CTTCTCTGGCTCCAAGTCTGGCAACACGGCCTCCCTGACCATCTCTG

GGCTCCAGGCTGAGGACGAGGCTGATTATTATTGCAGCTCATATACA

AGTAGAAGAACTTGGGTGTTCGGCGGAGGGACCATAGTGACCGTCCT

A

In some embodiments, the anti-ZIKV antibodies described herein bind to the same epitope as any of the exemplary antibodies described herein or competes against the exemplary antibody from binding to the ZIKV antigen. An "epitope" refers to the site on a target antigen that is recognized and bound by an antibody. The site can be entirely composed of amino acid components, entirely composed of chemical modifications of amino acids of the protein (e.g., glycosyl moieties), or composed of combinations thereof. Overlapping epitopes include at least one common amino acid residue. An epitope can be linear, which is typically 6-15 amino acids in length. Alternatively, the epitope can be conformational. The epitope to which an antibody binds can be determined by routine technology, for example, the epitope mapping method (see, e.g., descriptions below). An antibody that binds the same epitope as an exemplary antibody described herein may bind to exactly the same epitope or a substantially overlapping epitope (e.g., containing less than 3 non-overlapping amino acid residue, less than 2 non-overlapping amino acid residues, or only 1 non-overlapping amino acid residue) as the exemplary antibody. Whether two antibodies compete against each other from binding to the cognate antigen can be determined by a competition assay, which is well known in the art.

In some examples, the anti-ZIKV antibody comprises the same $V_H$ and/or $V_L$ CDRs as an exemplary antibody described herein. Two antibodies having the same $V_H$ and/or $V_L$ CDRs means that their CDRs are identical when determined by the same approach (e.g., the Kabat approach or the Chothia approach or the IMGT approach as known in the art). Such anti-ZIKV antibodies may have the same $V_H$, the same $V_L$, or both as compared to an exemplary antibody described herein.

Also within the scope of the present disclosure are functional variants of any of the exemplary anti-ZIKV antibodies as disclosed herein. Such functional variants are substantially similar to the exemplary antibody, both structurally and functionally. A functional variant comprises substantially the same $V_H$ and $V_L$ CDRs as the exemplary antibody.

For example, it may comprise only up to 5 (e.g., 4, 3, 2, or 1) amino acid residue variations in the total CDR regions of the antibody and binds the same epitope of ZIKV with substantially similar affinity (e.g., having a $K_D$ value in the same order). Alternatively or in addition, the amino acid residue variations are conservative amino acid residue substitutions. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In some embodiments, the anti-ZIKV antibody may comprise heavy chain CDRs that share at least 80% (e.g., 85%, 90%, 95%, or 98%) sequence identity, individually or collectively, with the $V_H$ CDRs of an exemplary antibody described herein. Alternatively or in addition, the anti-ZIKV antibody may comprise light chain CDRs that share at least 80% (e.g., 85%, 90%, 95%, or 98%) sequence identity, individually or collectively, with the $V_L$ CDRs as an exemplary antibody described herein.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, wordlength=3 to obtain amino acid sequences homologous to the protein molecules of interest. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

In some embodiments, the heavy chain of any of the anti-ZIKV antibodies as described herein may further comprise a heavy chain constant region (CH) or a portion thereof (e.g., CH1, CH2, CH3, or a combination thereof). The heavy chain constant region can of any suitable origin, e.g., human, mouse, rat, or rabbit. In one specific example, the heavy chain constant region is from a human IgG (a gamma heavy chain) of any IgG subfamily as described herein. In one example, the constant region is from human IgG4, an exemplary amino acid sequence of which is provided below (SEQ ID NO: 14):

```
ASTKGPSVFP LAPCSRSTSE STAALGCLVK DYFPEPVTVS

WNSGALTSGV HTFPAVLQSS GLYSLSSVVT VPSSSLGTKT

YTCNVDHKPS NTKVDKRVES KYGPPCPSCP APEFLGGPSV

FLFPPKPKDT LMISRTPEVT CVVVDVSQED PEVQFNWYVD
```

-continued

```
GVEVHNAKTK PREEQFNSTY RVVSVLTVLH QDWLNGKEYK

CKVSNKGLPS SIEKTISKAK GQPREPQVYT LPPSQEEMTK

NQVSLTCLVK GFYPSDIAVE WESNGQPENN YKTTPPVLDS

DGSFFLYSRL TVDKSRWQEG NVFSCSVMHE ALHNHYTQKS

LSLSLGK
```

In some embodiments, the anti-ZIKV antibody comprises the heavy chain constant region of SEQ ID NO: 14, or a variant thereof, which may contain an S/P substitution at the position as indicated (boldfaced and underlined). Alternatively, the heavy chain constant region of the antibodies described herein may comprise a single domain (e.g., CH1, CH2, or CH3) or a combination of any of the single domains, of a constant region (e.g., SEQ ID NO: 14).

When needed, the anti-ZIKV antibody as described herein may comprise a modified constant region. For example, it may comprise a modified constant region that is immunologically inert, e.g., does not trigger complement mediated lysis, or does not stimulate antibody-dependent cell mediated cytotoxicity (ADCC). ADCC activity can be assessed using methods disclosed in U.S. Pat. No. 5,500,362. In other embodiments, the constant region is modified as described in Eur. J. Immunol. (1999) 29:2613-2624; PCT Application No. PCT/GB99/01441; and/or UK Patent Application No. 9809951.8.

Any of the anti-ZIKV antibodies described herein may comprise a light chain that further comprises a light chain constant region, which can be any CL known in the art. In some examples, the CL is a kappa light chain. In other examples, the CL is a lambda light chain.

Antibody heavy and light chain constant regions are well known in the art, e.g., those provided in the IMGT database (imgt.org) or at vbase2.org/vbstat.php., both of which are incorporated by reference herein.

Antibodies capable of binding ZIKV as described herein can be made by any method known in the art. See, for example, Harlow and Lane, (1998) Antibodies: A Laboratory Manual, Cold Spring Harbor Laboratory, New York.

In some embodiments, antibodies specific to a target antigen (e.g., ZIKV or a CRD thereof) can be made by the conventional hybridoma technology. The full-length target antigen or a fragment thereof, optionally coupled to a carrier protein such as KLH, can be used to immunize a host animal for generating antibodies binding to that antigen. The route and schedule of immunization of the host animal are generally in keeping with established and conventional techniques for antibody stimulation and production, as further described herein. General techniques for production of mouse, humanized, and human antibodies are known in the art and are described herein. It is contemplated that any mammalian subject including humans or antibody producing cells therefrom can be manipulated to serve as the basis for production of mammalian, including human hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) *Nature* 256:495-497 or as modified by Buck, D. W., et al., *In Vitro,* 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the anti-ZIKV monoclonal antibodies described herein. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies capable of interfering with the ZIKV bioactivity. Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a target antigen or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, SOCl, or R1N=C=NR, where R and R1 are different alkyl groups, can yield a population of antibodies (e.g., monoclonal antibodies).

If desired, an antibody (monoclonal or polyclonal) of interest (e.g., produced by a hybridoma) may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity (affinity maturation), or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the target antigen and greater efficacy in inhibiting the bioactivity of ZIKV. It will be apparent to one of skill in the art that one or more polynucleotide changes can be made to the antibody and still maintain its binding specificity to the target antigen.

In other embodiments, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse® from Amgen, Inc. (Fremont, Calif.) and HuMAb-Mouse® and TC Mouse™ from Medarex, Inc. (Princeton, N.J.). In another alternative, antibodies may be made recombinantly by phage display or yeast technology. See, for example, U.S. Pat. Nos. 5,565,332; 5,580,717; 5,733,743; and 6,265,150; and Winter et al., (1994) *Annu. Rev. Immunol.* 12:433-455. Alternatively, the phage display technology (McCafferty et al., (1990) *Nature* 348:552-553) can be used to produce human antibodies and antibody fragments in vitro, from immunoglobulin variable (V) domain gene repertoires from unimmunized donors.

Alternatively, antibodies capable of binding to the target antigens as described herein may be isolated from a suitable antibody library via routine practice. Antibody libraries, which contain a plurality of antibody components, can be used to identify antibodies that bind to a specific target antigen (e.g., the ED1 of ZIKV) following routine selection processes as known in the art. In the selection process, an antibody library can be probed with the target antigen or a fragment thereof and members of the library that are capable of binding to the target antigen can be isolated, typically by retention on a support. Such screening process may be performed by multiple rounds (e.g., including both positive and negative selections) to enrich the pool of antibodies capable of binding to the target antigen. Individual clones of the enriched pool can then be isolated and further characterized to identify those having desired binding activity and biological activity. Sequences of the heavy chain and light chain variable domains can also be determined via conventional methodology.

There are a number of routine methods known in the art to identify and isolate antibodies capable of binding to the target antigens described herein, including phage display, yeast display, ribosomal display, or mammalian display technology.

As an example, phage displays typically use a covalent linkage to bind the protein (e.g., antibody) component to a bacteriophage coat protein. The linkage results from translation of a nucleic acid encoding the antibody component fused to the coat protein. The linkage can include a flexible peptide linker, a protease site, or an amino acid incorporated as a result of suppression of a stop codon. Phage display is described, for example, in U.S. Pat. No. 5,223,409; Smith (1985) Science 228:1315-1317; WO 92/18619; WO 91/17271; WO 92/20791; WO 92/15679; WO 93/01288; WO 92/01047; WO 92/09690; WO 90/02809; de Haard et al. (1999) J. Biol. Chem 274:18218-30; Hoogenboom et al. (1998) *Immunotechnology* 4:1-20; Hoogenboom et al. (2000) *Immunol Today* 2:371-8 and Hoet et al. (2005) *Nat Biotechnol.* 23(3)344-8. Bacteriophage displaying the protein component can be grown and harvested using standard phage preparatory methods, e.g. PEG precipitation from growth media. After selection of individual display phages, the nucleic acid encoding the selected protein components can be isolated from cells infected with the selected phages or from the phage themselves, after amplification. Individual colonies or plaques can be selected, and then the nucleic acid may be isolated and sequenced.

Other display formats include cell-based display (see, e.g., WO 03/029456), protein-nucleic acid fusions (see, e.g., U.S. Pat. No. 6,207,446), ribosome display (See, e.g., Mattheakis et al. (1994) *Proc. Natl. Acad. Sci. USA* 91:9022 and Hanes et al. (2000) *Nat Biotechnol.* 18:1287-92; Hanes et al. (2000) *Methods Enzymol.* 328:404-30; and Schaffitzel et al. (1999) *J Immunol Methods.* 231(1-2):119-35), and *E. coli* periplasmic display (*J Immunol Methods.* 2005 Nov. 22; PMID: 16337958).

After display library members are isolated for binding to the target antigen, each isolated library member can be also tested for its ability to bind to a non-target molecule to evaluate its binding specificity. Examples of non-target molecules include streptavidin on magnetic beads, blocking agents such as bovine serum albumin, non-fat bovine milk, soy protein, any capturing or target immobilizing monoclonal antibody, or non-transfected cells which do not express the target. A high-throughput ELISA screen can be used to obtain the data, for example. The ELISA screen can also be used to obtain quantitative data for binding of each library member to the target as well as for cross species reactivity to related targets or subunits of the target antigen and also under different condition such as pH 6 or pH 7.5. The non-target and target binding data are compared (e.g., using a computer and software) to identify library members that specifically bind to the target.

After selecting candidate library members that bind to a target, each candidate library member can be further analyzed, e.g., to further characterize its binding properties for the target, e.g., ZIKV. Each candidate library member can be subjected to one or more secondary screening assays. The assay can be for a binding property, a catalytic property, an inhibitory property, a physiological property (e.g., cytotoxicity, renal clearance, immunogenicity), a structural property (e.g., stability, conformation, oligomerization state) or another functional property. The same assay can be used repeatedly, but with varying conditions, e.g., to determine pH, ionic, or thermal sensitivities.

As appropriate, the assays can use a display library member directly, a recombinant polypeptide produced from the nucleic acid encoding the selected polypeptide, or a synthetic peptide synthesized based on the sequence of the selected polypeptide. In the case of selected Fabs, the Fabs can be evaluated or can be modified and produced as intact IgG proteins. Exemplary assays for binding properties are described below.

Binding proteins can also be evaluated using an ELISA assay. For example, each protein is contacted to a microtitre plate whose bottom surface has been coated with the target, e.g., a limiting amount of the target. The plate is washed with buffer to remove non-specifically bound polypeptides. Then the amount of the binding protein bound to the target on the plate is determined by probing the plate with an antibody that can recognize the binding protein, e.g., a tag or constant portion of the binding protein. The antibody is linked to a detection system (e.g., an enzyme such as alkaline phosphatase or horse radish peroxidase (HRP) which produces a colorimetric product when appropriate substrates are provided).

Alternatively, the ability of a binding protein described herein to bind a target antigen can be analyzed using a homogenous assay, i.e., after all components of the assay are added, additional fluid manipulations are not required. For example, fluorescence resonance energy transfer (FRET) can be used as a homogenous assay (see, for example, Lakowicz et al., U.S. Pat. No. 5,631,169; Stavrianopoulos, et al., U.S. Pat. No. 4,868,103). A fluorophore label on the first molecule (e.g., the molecule identified in the fraction) is selected such that its emitted fluorescent energy can be absorbed by a fluorescent label on a second molecule (e.g., the target) if the second molecule is in proximity to the first molecule. The fluorescent label on the second molecule fluoresces when it absorbs to the transferred energy. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. A binding event that is configured for monitoring by FRET can be conveniently measured through standard fluorometric detection means, e.g., using a fluorimeter. By titrating the amount of the first or second binding molecule, a binding curve can be generated to estimate the equilibrium binding constant.

Surface plasmon resonance (SPR) can be used to analyze the interaction of a binding protein and a target antigen. SPR or Biomolecular Interaction Analysis (BIA) detects biospecific interactions in real time, without labeling any of the interactants. Changes in the mass at the binding surface (indicative of a binding event) of the BIA chip result in alterations of the refractive index of light near the surface (the optical phenomenon of SPR). The changes in the refractivity generate a detectable signal, which are measured as an indication of real-time reactions between biological molecules. Methods for using SPR are described, for example, in U.S. Pat. No. 5,641,640; Raether, 1988, Surface Plasmons Springer Verlag; Sjolander and Urbaniczky, 1991, *Anal. Chem.* 63:2338-2345; Szabo et al., 1995, *Curr. Opin. Struct. Biol.* 5:699-705 and on-line resources provide by BIAcore International AB (Uppsala, Sweden).

Information from SPR can be used to provide an accurate and quantitative measure of the equilibrium dissociation constant ($K_D$), and kinetic parameters, including $K_{on}$ and $K_{off}$, for the binding of a binding protein to a target. Such data can be used to compare different biomolecules. For example, selected proteins from an expression library can be compared to identify proteins that have high affinity for the target or that have a slow $K_{off}$. This information can also be used to develop structure-activity relationships (SAR). For example, the kinetic and equilibrium binding parameters of matured versions of a parent protein can be compared to the parameters of the parent protein. Variant amino acids at given positions can be identified that correlate with particular binding parameters, e.g., high affinity and slow $K_{off}$. This information can be combined with structural modeling (e.g., using homology modeling, energy minimization, or structure determination by x-ray crystallography or NMR). As a result, an understanding of the physical interaction between the protein and its target can be formulated and used to guide other design processes.

As a further example, cellular assays may be used. Binding proteins can be screened for ability to bind to cells which transiently or stably express and display the target of interest on the cell surface. For example, ZIKV binding proteins can be fluorescently labeled and binding to ZIKV in the presence or absence of antagonistic antibody can be detected by a change in fluorescence intensity using flow cytometry e.g., a FACS machine.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments.

Genetically engineered antibodies, such as humanized antibodies, chimeric antibodies, single-chain antibodies, and bi-specific antibodies, can be produced via, e.g., conventional recombinant technology. In one example, DNA encoding a monoclonal antibodies specific to a target antigen can be readily isolated and sequenced using conventional procedures (e.g., by using oligonucleotide probes that are capable of binding specifically to genes encoding the heavy and light chains of the monoclonal antibodies). Once isolated, the DNA may be placed into one or more expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA can then be modified, for example, by substituting the coding sequence for human heavy and light chain constant domains in place of the homologous murine sequences, Morrison et al., (1984) *Proc. Nat. Acad. Sci.* 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

Techniques developed for the production of "chimeric antibodies" are well known in the art. See, e.g., Morrison et al. (1984) *Proc. Natl. Acad. Sci. USA* 81, 6851; Neuberger et al. (1984) *Nature* 312, 604; and Takeda et al. (1984) *Nature* 314:452.

Methods for constructing humanized antibodies are also well known in the art. See, e.g., Queen et al., *Proc. Natl. Acad. Sci. USA,* 86:10029-10033 (1989). In one example, variable regions of $V_H$ and $V_L$ of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human $V_H$ and $V_L$ chains having amino acid sequences that are homologous to those of the parent non-human antibody are identified from any antibody gene database using the parent $V_H$ and $V_L$ sequences as search queries. Human $V_H$ and $V_L$ acceptor genes are then selected.

The CDR regions within the selected human acceptor genes can be replaced with the CDR regions from the parent non-human antibody or functional variants thereof. When necessary, residues within the framework regions of the parent chain that are predicted to be important in interacting with the CDR regions (see above description) can be used to substitute for the corresponding residues in the human acceptor genes.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions. Alternatively, techniques described for the production of single chain antibodies (U.S. Pat. Nos. 4,946,778 and 4,704,692) can be adapted to produce a phage or yeast scFv library and scFv clones specific to ZIKV can be identified from the library following routine procedures. Positive clones can be subjected to further screening to identify those that inhibit ZIKV bioactivity.

Antibodies obtained following a method known in the art and described herein can be characterized using methods well known in the art. For example, one method is to identify the epitope to which the antigen binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence, to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screening by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various fragments of the ZIKV polypeptide have been replaced (swapped) with sequences from a closely related, but antigenically distinct protein (such as another member of the 0-galactoside-binding soluble lectin family). By assessing binding of the antibody to the mutant ZIKV, the importance of the particular antigen fragment to antibody binding can be assessed.

Alternatively, competition assays can be performed using other antibodies known to bind to the same antigen to determine whether an antibody binds to the same epitope as the other antibodies. Competition assays are well known to those of skill in the art.

In some examples, an anti-ZIKV antibody is prepared by recombinant technology as exemplified below.

Nucleic acids encoding the heavy and light chain of an anti-ZIKV antibody as described herein can be cloned into one expression vector, each nucleotide sequence being in operable linkage to a suitable promoter. In one example, each of the nucleotide sequences encoding the heavy chain and light chain is in operable linkage to a distinct prompter. Alternatively, the nucleotide sequences encoding the heavy chain and the light chain can be in operable linkage with a single promoter, such that both heavy and light chains are expressed from the same promoter. When necessary, an internal ribosomal entry site (IRES) can be inserted between the heavy chain and light chain encoding sequences.

In some examples, the nucleotide sequences encoding the two chains of the antibody are cloned into two vectors, which can be introduced into the same or different cells. When the two chains are expressed in different cells, each of them can be isolated from the host cells expressing such and the isolated heavy chains and light chains can be mixed and incubated under suitable conditions allowing for the formation of the antibody.

Generally, a nucleic acid sequence encoding one or all chains of an antibody can be cloned into a suitable expression vector in operable linkage with a suitable promoter using methods known in the art. For example, the nucleotide sequence and vector can be contacted, under suitable conditions, with a restriction enzyme to create complementary ends on each molecule that can pair with each other and be joined together with a ligase. Alternatively, synthetic nucleic acid linkers can be ligated to the termini of a gene. These synthetic linkers contain nucleic acid sequences that correspond to a particular restriction site in the vector. The selection of expression vectors/promoter would depend on the type of host cells for use in producing the antibodies.

A variety of promoters can be used for expression of the antibodies described herein, including, but not limited to, cytomegalovirus (CMV) intermediate early promoter, a viral LTR such as the *Rous sarcoma* virus LTR, HIV-LTR, HTLV-1 LTR, the simian virus 40 (SV40) early promoter, *E. coli* lac UV5 promoter, and the herpes simplex tk virus promoter.

Regulatable promoters can also be used. Such regulatable promoters include those using the lac repressor from *E. coli* as a transcription modulator to regulate transcription from lac operator-bearing mammalian cell promoters [Brown, M. et al., *Cell,* 49:603-612 (1987)], those using the tetracycline repressor (tetR) [Gossen, M., and Bujard, H., *Proc. Natl. Acad. Sci. USA* 89:5547-5551 (1992); Yao, F. et al., *Human Gene Therapy,* 9:1939-1950 (1998); Shockelt, P., et al., *Proc. Natl. Acad. Sci. USA,* 92:6522-6526 (1995)]. Other systems include FK506 dimer, VP16 or p65 using astradiol, RU486, diphenol murislerone, or rapamycin. Inducible systems are available from Invitrogen, Clontech and Ariad.

Regulatable promoters that include a repressor with the operon can be used. In one embodiment, the lac repressor from *E. coli* can function as a transcriptional modulator to regulate transcription from lac operator-bearing mammalian cell promoters [M. Brown et al., *Cell,* 49:603-612 (1987)]; Gossen and Bujard (1992); [M. Gossen et al., *Natl. Acad. Sci. USA,* 89:5547-5551 (1992)] combined the tetracycline repressor (tetR) with the transcription activator (VP 16) to create a tetR-mammalian cell transcription activator fusion protein, tTa (tetR-VP 16), with the tetO-bearing minimal promoter derived from the human cytomegalovirus (hCMV) major immediate-early promoter to create a tetR-tet operator system to control gene expression in mammalian cells. In one embodiment, a tetracycline inducible switch is used. The tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter (Yao et al., *Human Gene Therapy,* 10(16):1392-1399 (2003)). One particular advantage of this tetracycline inducible switch is that it does not require the use of a tetracycline repressor-mammalian cells transactivator or repressor fusion protein, which in some instances can be toxic to cells (Gossen et al., *Natl. Acad. Sci. USA,* 89:5547-5551 (1992); Shockett et al., *Proc. Natl. Acad. Sci. USA,* 92:6522-6526 (1995)), to achieve its regulatable effects.

Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes), versatile multiple cloning sites; and T7 and SP6 RNA promoters for in vitro transcription of sense and antisense RNA. Suitable vectors and methods for producing vectors containing transgenes are well known and available in the art.

Examples of polyadenylation signals useful to practice the methods described herein include, but are not limited to, human collagen I polyadenylation signal, human collagen II polyadenylation signal, and SV40 polyadenylation signal.

One or more vectors (e.g., expression vectors) comprising nucleic acids encoding any of the antibodies may be introduced into suitable host cells for producing the antibodies. The host cells can be cultured under suitable conditions for expression of the antibody or any polypeptide chain thereof. Such antibodies or polypeptide chains thereof can be recovered by the cultured cells (e.g., from the cells or the culture supernatant) via a conventional method, e.g., affinity purification. If necessary, polypeptide chains of the antibody can be incubated under suitable conditions for a suitable period of time allowing for production of the antibody.

In some embodiments, methods for preparing an antibody described herein involve a recombinant expression vector that encodes both the heavy chain and the light chain of an anti-ZIKV antibody, as also described herein. The recombinant expression vector can be introduced into a suitable host cell (e.g., a dhfr-CHO cell) by a conventional method, e.g., calcium phosphate-mediated transfection. Positive transformant host cells can be selected and cultured under suitable conditions allowing for the expression of the two polypeptide chains that form the antibody, which can be recovered from the cells or from the culture medium. When necessary, the two chains recovered from the host cells can be incubated under suitable conditions allowing for the formation of the antibody.

In one example, two recombinant expression vectors are provided, one encoding the heavy chain of the anti-ZIKV antibody and the other encoding the light chain of the anti-ZIKV antibody. Both of the two recombinant expression vectors can be introduced into a suitable host cell (e.g., dhfr-CHO cell) by a conventional method, e.g., calcium phosphate-mediated transfection. Alternatively, each of the expression vectors can be introduced into a suitable host cells. Positive transformants can be selected and cultured under suitable conditions allowing for the expression of the polypeptide chains of the antibody. When the two expression vectors are introduced into the same host cells, the antibody produced therein can be recovered from the host cells or from the culture medium. If necessary, the polypeptide chains can be recovered from the host cells or from the culture medium and then incubated under suitable conditions allowing for formation of the antibody. When the two expression vectors are introduced into different host cells, each of them can be recovered from the corresponding host cells or from the corresponding culture media. The two polypeptide chains can then be incubated under suitable conditions for formation of the antibody.

Standard molecular biology techniques are used to prepare the recombinant expression vector, transfect the host cells, select for transformants, culture the host cells and recovery of the antibodies from the culture medium. For example, some antibodies can be isolated by affinity chromatography with a Protein A or Protein G coupled matrix.

Any of the nucleic acids encoding the heavy chain, the light chain, or both of an anti-ZIKV antibody as described herein, vectors (e.g., expression vectors) containing such; and host cells comprising the vectors are within the scope of the present disclosure.

Anti-ZIKV antibodies thus prepared can be can be characterized using methods known in the art, whereby reduction, amelioration, or neutralization of ZIKV biological activity is detected and/or measured. For example, an ELISA-type assay may be suitable for qualitative or quantitative measurement of ZIKV bioactivity neutralization.

The present disclosure provides pharmaceutical compositions comprising the anti-ZIKV antibody described herein and uses of such for neutralizing ZIKV bioactivity.

The antibodies and antigen-binding antibody fragments thereof described herein may be used to identify a ZIKV infection in a subject. As the antibodies bind ZIKV with high specificity, the detection of ZIKV antigens in a biological sample from a subject suspected of having, or at risk of having, a ZIKV infection, can be accomplished using any method known in the art. For example, an ELISA may be used to determine whether or not the biological sample contains ZIKV antigens. Other examples include, but are not limited to, precipitation reactions, agglutination reactions, complement fixation, immunofluorescent assays, and radioimmunoassays.

The antibodies and antigen-binding antibody fragments thereof described herein may be used to treat a ZIKV infection in a subject. As the antibodies bind ZIKV with high specificity, they may be used to treat a subject having, or suspected of having a ZIKV infection.

As used herein, the term "treating" refers to the application or administration of a composition including one or more active agents to a subject, who has a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder.

Alleviating a target disease/disorder includes delaying the development or progression of the disease, or reducing disease severity or prolonging survival. Alleviating the disease or prolonging survival does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

In some embodiments, the antibodies described herein are administered to a subject in need of the treatment at an amount sufficient to inhibit the bioactivity of ZIKV by at least 20% (e.g., 30%, 40%, 50%, 60%, 70%, 80%, 90% or greater) in vivo. In other embodiments, the antibodies are administered in an amount effective in reducing the bioactivity level of ZIKV by at least 20% (e.g., 30%, 40%, 50%, 60%, 70%, 80%, 90% or greater).

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods. In some examples, the pharmaceutical composition is administered intraocularly or intravitreally.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipient is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In one embodiment, an antibody is administered via site-specific or targeted local delivery techniques. Examples of site-specific or targeted local delivery techniques include various implantable depot sources of the antibody or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Targeted delivery of therapeutic compositions containing an antisense polynucleotide, expression vector, or subgenomic polynucleotides can also be used. Receptor-mediated DNA delivery techniques are described in, for example, Findeis et al., *Trends Biotechnol.* (1993) 11:202; Chiou et al., Gene Therapeutics: Methods And Applications Of Direct Gene Transfer (J. A. Wolff, ed.) (1994); Wu et al., *J. Biol. Chem.* (1988) 263:621; Wu et al., *J. Biol. Chem.* (1994) 269:542; Zenke et al., *Proc. Natl. Acad. Sci. USA* (1990) 87:3655; Wu et al., *J. Biol. Chem.* (1991) 266:338.

Therapeutic compositions containing a polynucleotide (e.g., those encoding the antibodies described herein) are administered in a range of about 100 ng to about 200 mg of DNA for local administration in a gene therapy protocol. In some embodiments, concentration ranges of about 500 ng to about 50 mg, about 1 μg to about 2 mg, about 5 μg to about 500 μg, and about 20 μg to about 100 μg of DNA or more can also be used during a gene therapy protocol.

The therapeutic polynucleotides and polypeptides described herein can be delivered using gene delivery vehicles. The gene delivery vehicle can be of viral or non-viral origin (see generally, Jolly, *Cancer Gene Therapy* (1994) 1:51; Kimura, *Human Gene Therapy* (1994) 5:845; Connelly, *Human Gene Therapy* (1995) 1:185; and Kaplitt, *Nature Genetics* (1994) 6:148). Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, *Hum. Gene Ther.* (1992) 3:147 can also be employed.

Non-viral delivery vehicles and methods can also be employed, including, but not limited to, polycationic condensed DNA linked or unlinked to killed adenovirus alone (see, e.g., Curiel, *Hum. Gene Ther.* (1992) 3:147); ligand-linked DNA (see, e.g., Wu, *J. Biol. Chem.* (1989) 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, *Mol. Cell. Biol.* (1994) 14:2411, and in Woffendin, *Proc. Natl. Acad. Sci.* (1994) 91:1581.

The particular dosage regimen, i.e., dose, timing and repetition, used in the method described herein will depend on the particular subject and that subject's medical history.

In some embodiments, more than one antibody, or a combination of an antibody and another suitable therapeutic agent, may be administered to a subject in need of the treatment. The antibody can also be used in conjunction with other agents that serve to enhance and/or complement the effectiveness of the agents.

Treatment efficacy for a target disease/disorder can be assessed by methods well-known in the art.

Any of the anti-ZIKV antibodies described herein may be utilized in conjunction with other types of therapy for ZIKV or other infectious diseases, such as surgery, gene therapy, or in conjunction with other types of therapy for downstream effects of Zika such as autoimmune diseases, e.g. rest, fluids, pain medication, and so forth. Such therapies can be administered simultaneously or sequentially (in any order) with the immunotherapy according to the present disclosure.

When co-administered with an additional therapeutic agent, suitable therapeutically effective dosages for each agent may be lowered due to the additive action or synergy.

The antibodies, as well as the encoding nucleic acids or nucleic acid sets, vectors comprising such, or host cells comprising the vectors, as described herein can be mixed with a pharmaceutically acceptable carrier (excipient) to form a pharmaceutical composition for use in treating a target disease. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The pharmaceutical compositions to be used in the present methods can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

In some examples, the pharmaceutical composition described herein comprises liposomes containing the antibodies (or the encoding nucleic acids) which can be prepared by methods known in the art, such as described in Epstein, et al., *Proc. Natl. Acad. Sci. USA* 82:3688 (1985); Hwang, et al., *Proc. Natl. Acad. Sci. USA* 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The antibodies, or the encoding nucleic acid(s), may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0.im, particularly 0.1 and 0.5.im, and have a pH in the range of 5.5 to 8.0.

The emulsion compositions can be those prepared by mixing an antibody with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulized by use of gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

To practice the method disclosed herein, an effective amount of the pharmaceutical composition described herein can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, the antibodies as described herein can be aerosolized using a fluorocarbon formulation and a metered dose inhaler, or inhaled as a lyophilized and milled powder.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having a target disease/disorder, such as ZIKV.

A subject suspected of having any of such target disease/disorder might show one or more symptoms of the disease/disorder. A subject at risk for the disease/disorder can be a subject having one or more of the risk factors for that disease/disorder.

As used herein, "an effective amount" refers to the amount of each active agent required to confer therapeutic effect on the subject, either alone or in combination with one or more other active agents. In some embodiments, the therapeutic effect is reduced ZIKV bioactivity. Determination of whether an amount of the antibody achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of a target disease/disorder. Alternatively, sustained continuous release formulations of an antibody may be appropriate. Various formulations and devices for achieving sustained release are known in the art.

In one example, dosages for an antibody as described herein may be determined empirically in individuals who have been given one or more administration(s) of the antibody. Individuals are given incremental dosages of the antagonist. To assess efficacy of the antagonist, an indicator of the disease/disorder can be followed.

Generally, for administration of any of the antibodies described herein, an initial candidate dosage can be about 2 mg/kg. For the purpose of the present disclosure, a typical daily dosage might range from about any of 0.1 μg/kg to 3 μg/kg to 30 μg/kg to 300 μg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate a target disease or disorder, or a symptom thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 μg/mg to about 2 mg/kg (such as about 3 μg/mg, about 10 μg/mg, about 30 μg/mg, about 100 μg/mg, about 300 μg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

In some embodiments, for an adult patient of normal weight, doses ranging from about 0.3 to 5.00 mg/kg may be administered. In some examples, the dosage of the anti-ZIKV antibody described herein can be 10 mg/kg. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of an antibody as described herein will depend on the specific antibody, antibodies, and/or non-antibody peptide (or compositions thereof) employed, the type and severity of the disease/disorder, whether the antibody is administered for preventive or therapeutic purposes, previous therapy, the patient's clinical history and response to the antagonist, and the discretion of the attending physician. Typically the clinician will administer an antibody, until a dosage is reached that achieves the desired result. In some embodiments, the desired result is an increase in anti-tumor immune response in the tumor microenvironment. Methods of determining whether a dosage resulted in the desired result would be evident to one of skill in the art. Administration of one or more antibodies can be continuous or intermittent, depending, for example, upon the recipient's physiological condition, whether the purpose of the administration is therapeutic or prophylactic, and other factors known to skilled practitioners. The administration of an antibody may be essentially continuous over a preselected period of time or may be in a series of spaced dose, e.g., either before, during, or after developing a target disease or disorder.

The present disclosure also provides kits for use in treating or alleviating Zika virus (ZIKV). Such kits can include one or more containers comprising an anti-ZIKV antibody, e.g., any of those described herein.

In some embodiments, the kit can comprise instructions for use in accordance with any of the methods described herein. The included instructions can comprise a description of administration of the anti-ZIKV antibody, and optionally the second therapeutic agent, to treat, delay the onset, or alleviate a target disease as those described herein. The kit may further comprise a description of selecting an individual suitable for treatment based on identifying whether that individual has the target disease, e.g., applying the diagnostic method as described herein. In still other embodiments, the instructions comprise a description of administering an antibody to an individual at risk of the target disease.

The instructions relating to the use of an anti-ZIKV antibody generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating ZIKV. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierce-able by a hypodermic injection needle). At least one active agent in the composition is an anti-ZIKV antibody as those described herein.

Kits may optionally provide additional components such as buffers and interpretive information. Normally, the kit comprises a container and a label or package insert(s) on or associated with the container. In some embodiments, the invention provides articles of manufacture comprising contents of the kits described above.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

In order that the invention described herein may be more fully understood, the following examples are set forth. The examples described in this application are offered to illustrate the compounds, pharmaceutical compositions, and methods provided herein and are not to be construed in any way as limiting their scope.

Example 1. Isolation and Characterization of Candidate Antibodies

To understand the antibody response in individuals experiencing ZIKV as a primary flavivirus infection, four individuals who had acquired ZIKV infections during foreign travel were identified (Table 1). All subjects were infected in Latin America between 2015-2016 and experienced uncomplicated, self-limited, symptomatic infections that resolved within 1 week. Only late convalescent blood samples collected 6 months or more after infection were analyzed for the current study. Subjects DT206 and DT244 reported positive ZIKV PCR testing during clinical evaluation following travel, and anti-ZIKV IgM was detected in plasma samples obtained from those two subjects within 12 weeks of infection but not in the late convalescent samples used in these studies. All four subjects had strong type-specific neutralizing antibody responses to ZIKV (FRNT50 titer range 1845-5267) (FIG. 19C).

TABLE 1

Demographic and Serologic Characteristics of Subjects

| | Place infected | Time post infection | YFV vaccine | Symptoms | FRNT50 DENV1 | FRNT50 DENV2 | FRNT50 DENV3 | FRNT50 DENV4 | FRNT50 ZIKV |
|---|---|---|---|---|---|---|---|---|---|
| DT168 | Brazil | 6 months | unknown | F, R, C, HA, AR, GI | <20 | <20 | 28 | <20 | 3931 |
| DT172 | Colombia | 6 months | no | F, R, C, AR | <20 | <20 | <20 | <20 | 5267 |
| DT206 | Honduras | 6 months | no | F, R, HA, AR | <20 | <20 | <20 | <20 | 5048 |
| DT244 | Puerto Rico | 6 months | no | R | <20 | <20 | <20 | <20 | 1845 |

Figure 19A:
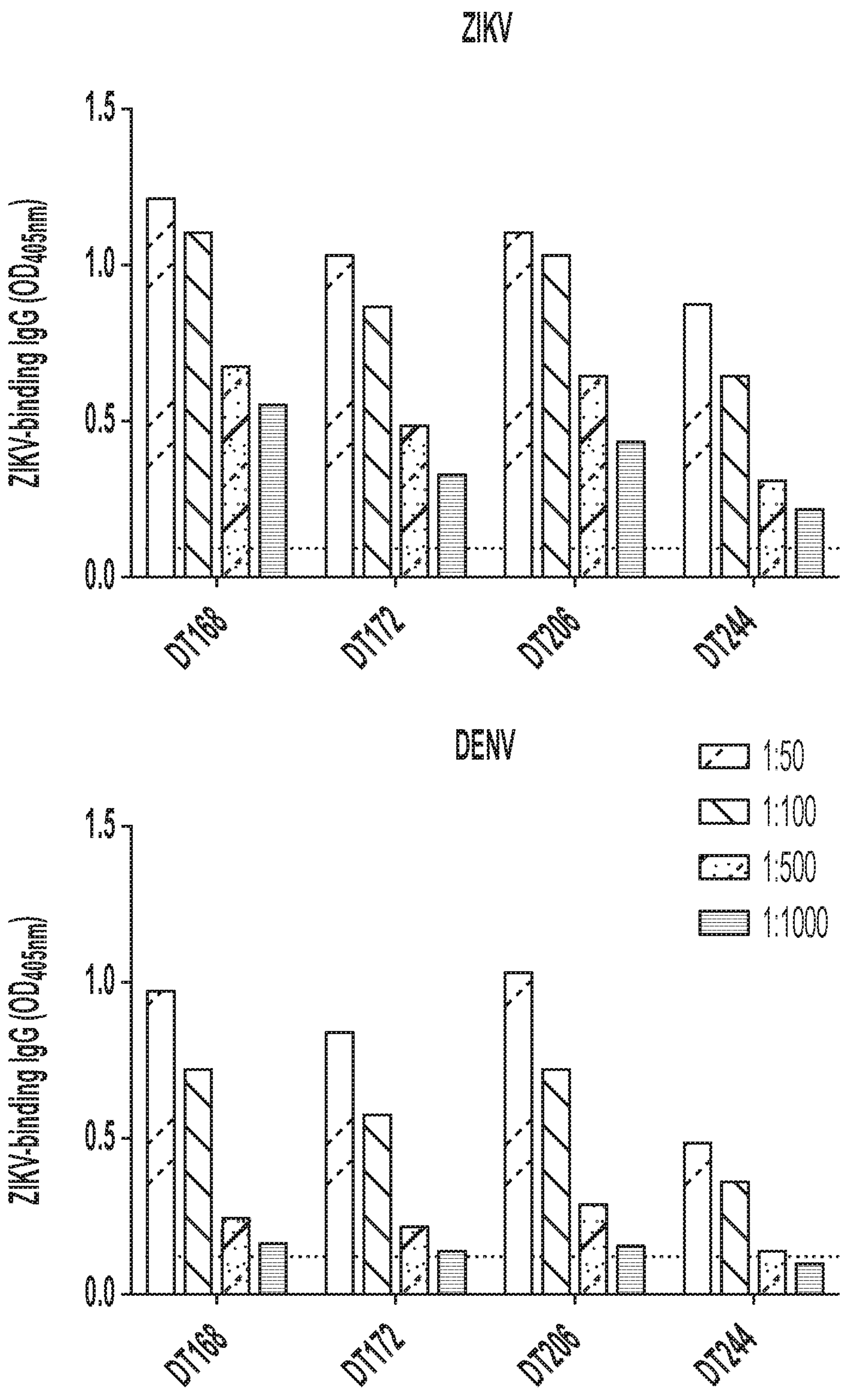
FIGS. 19A-19C show primary serologic response to ZIKV.
Figure 19B:
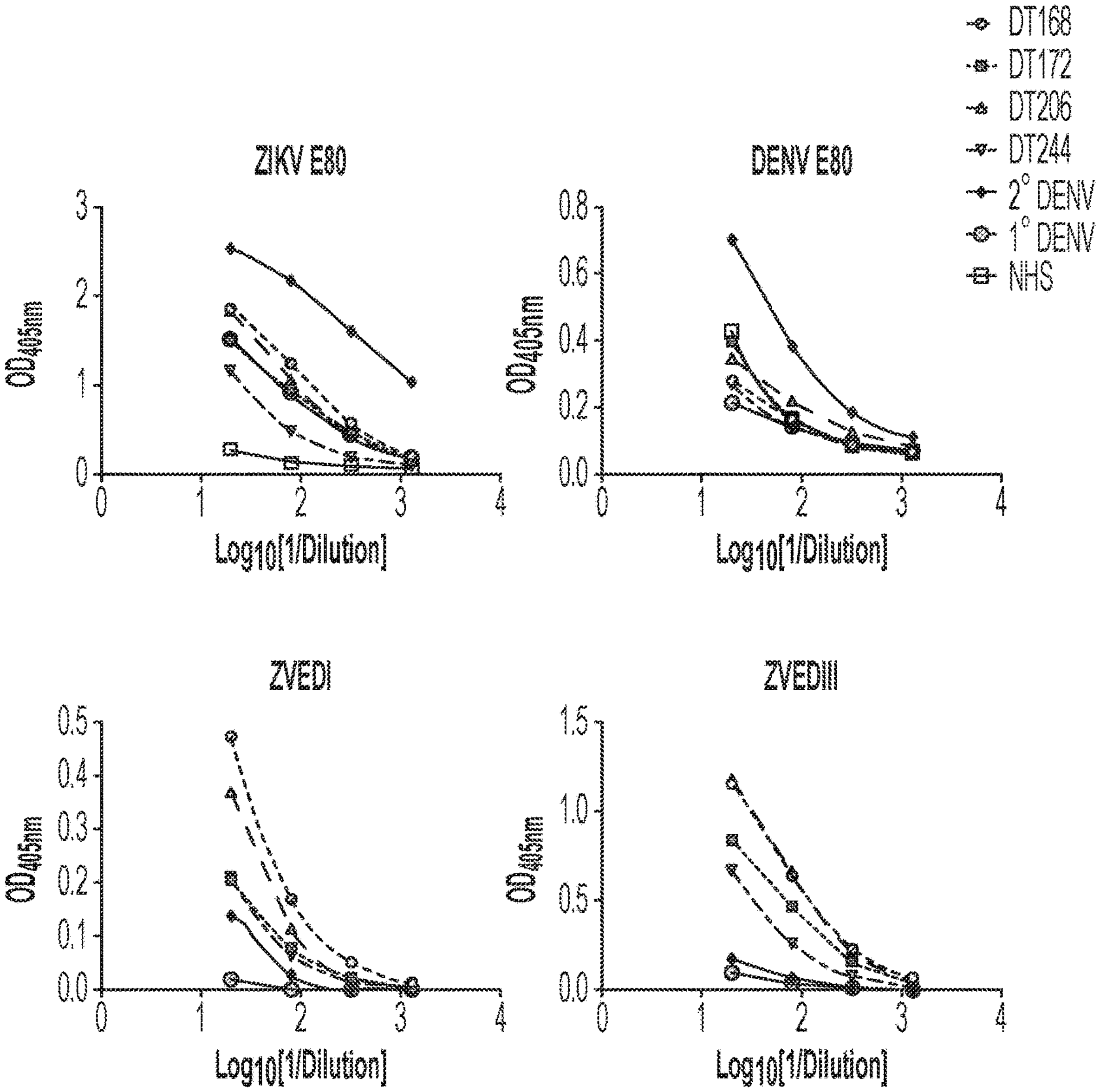
Figure 19C:
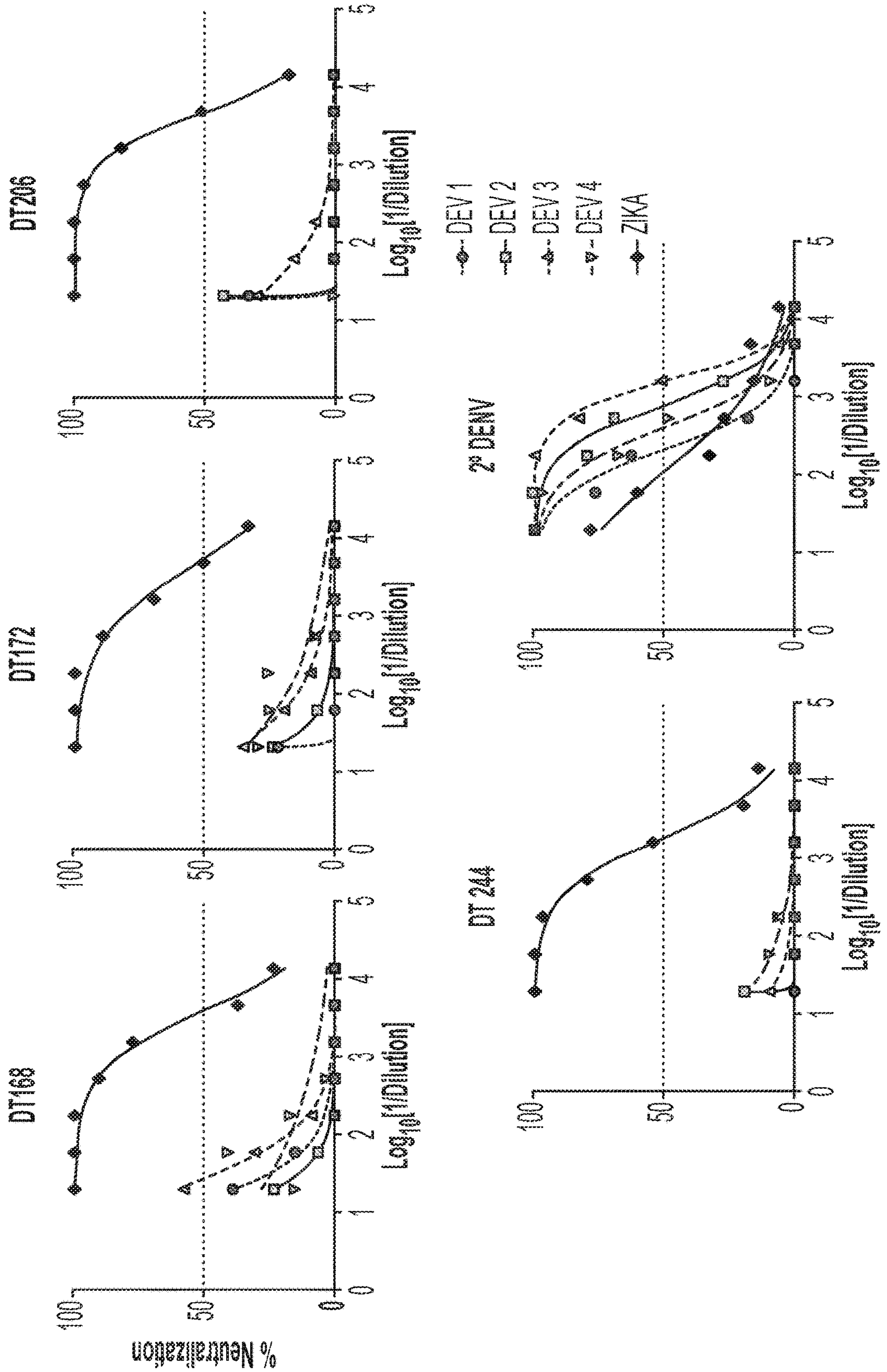

F = fever, R = rash, C = conjunctivitis, HA = headache, AR = arthritis/arthralgia, GI = nausea, vomiting or diarrhea Plasma from all four ZIKV cases exhibited positive IgG binding in antigen capture ELISA using ZIKV or a mix of DENV1-4 virus as antigens, over a range of plasma dilutions (FIG. 19A). The binding signal for DENV decayed more rapidly than for ZIKV, reaching assay limit of detection between the 1:500-1:1000 dilution. IgG binding to ZIKV was readily detectable over background for all four primary ZIKV plasma at the highest dilution (1:1000), indicating higher IgG titers to ZIKV. All four plasma samples contained IgG antibodies that also bound ZIKV recombinant E (ZIKV E80) and E domain I and III (ZVEDI and ZVEDIII) (FIG. 19B). Consistent with the serologic diagnostic criteria used to confirm ZIKV cases, the plasma from the four subjects strongly neutralized ZIKV by focus reduction neutralization tests (FRNT) and exhibited minimal to no cross-neutralization of DENV serotypes 1-4 (FIG. 19C, Table 1).

Figure 20A:
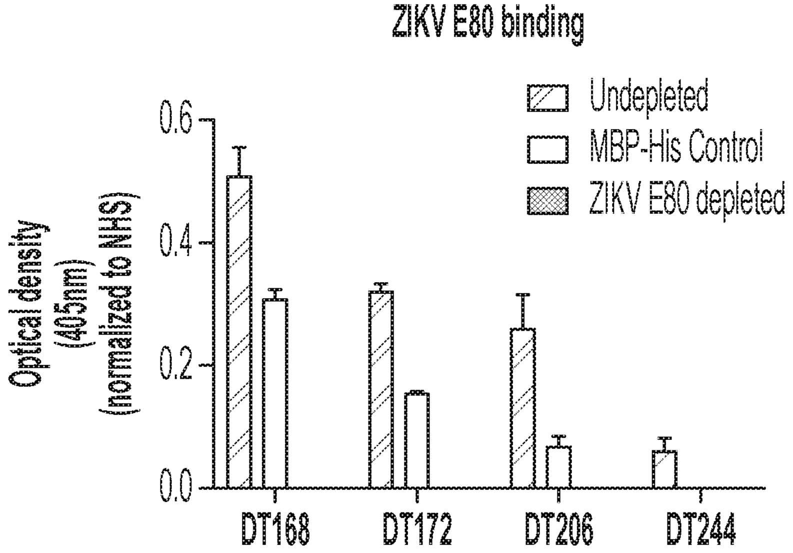
FIGS. 20A-20E show that antibodies against quaternary epitopes are the predominant mediators of ZIKV neutralization.
Figure 20B:
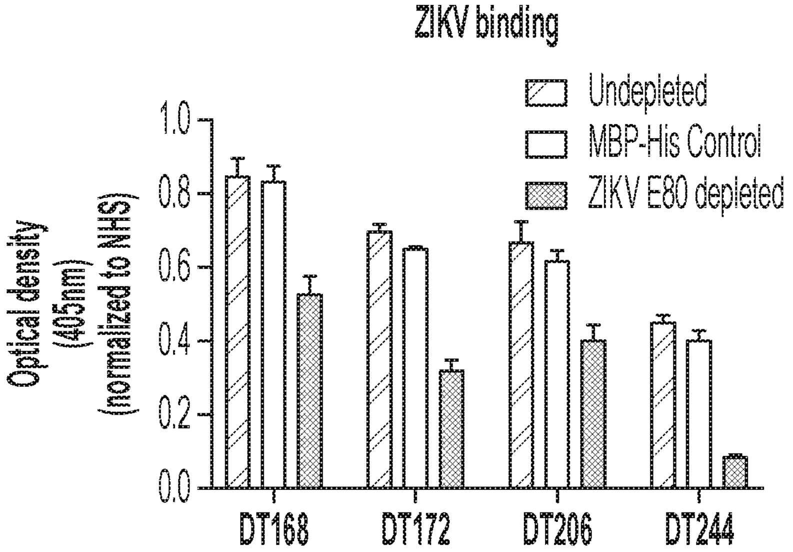
Figures 20C, 20D:
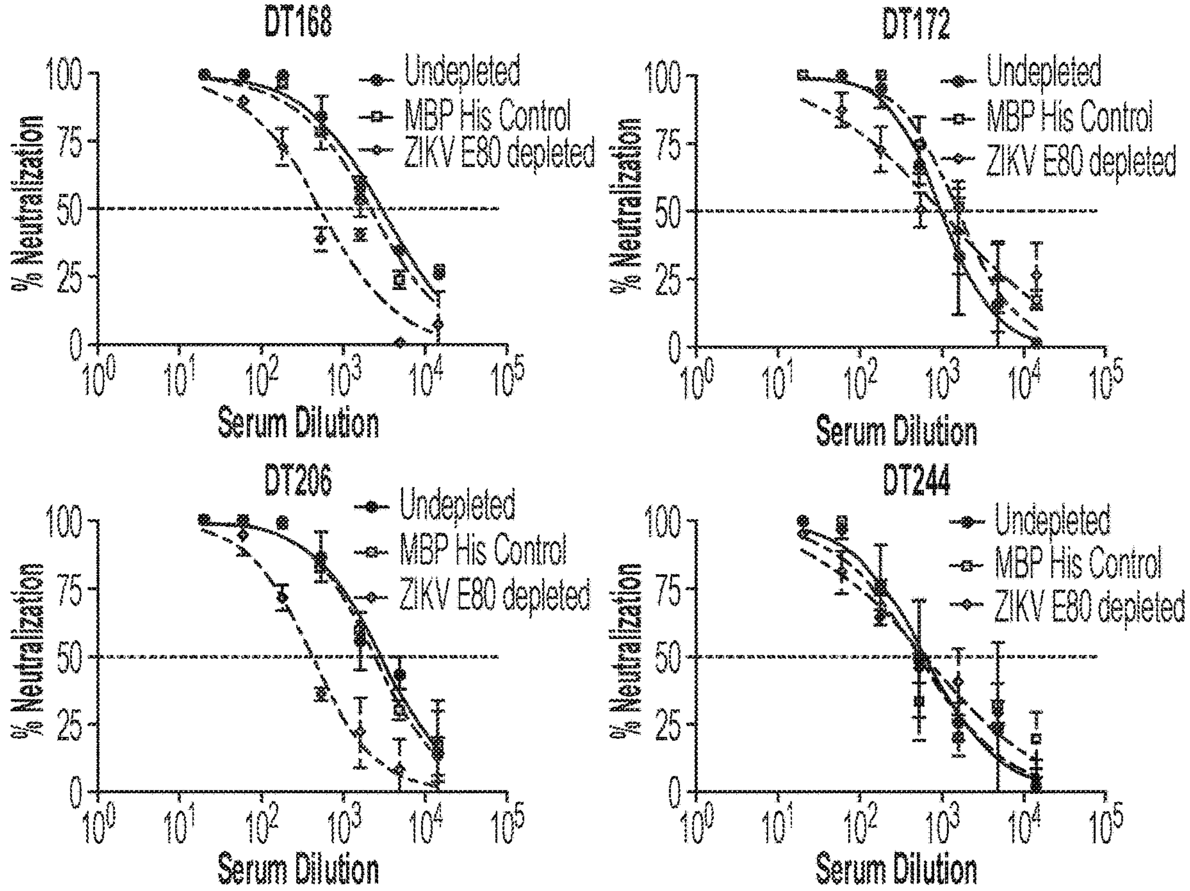
Figure 20E:
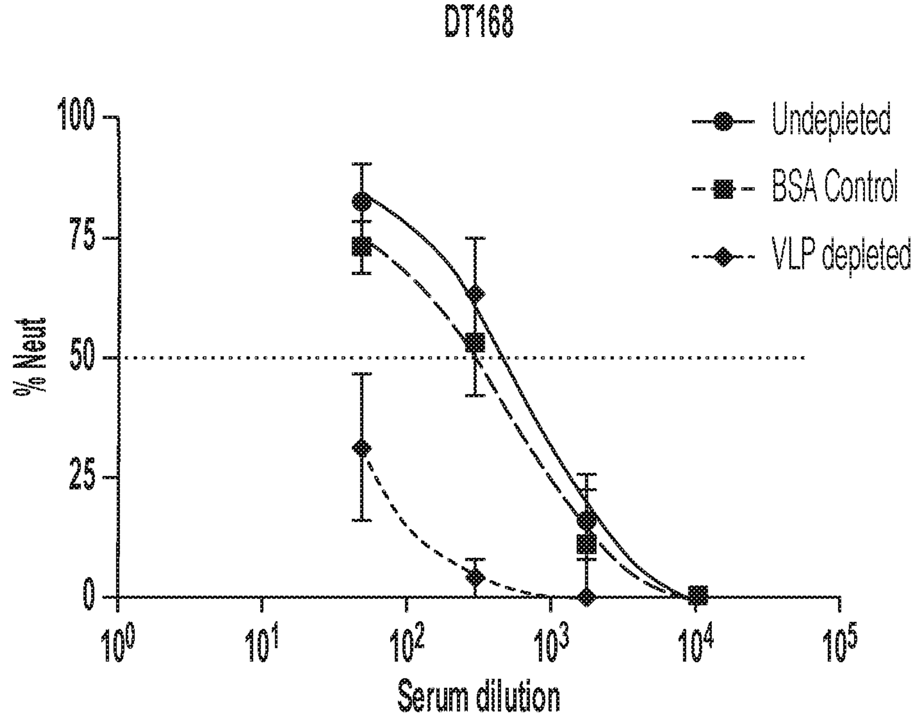

Strongly-neutralizing antibody responses to DENV often target E protein quaternary epitopes displayed on the virion but not on recombinantly-expressed monomeric E protein (18-20). Whether plasma neutralizing antibody in people infected with ZIKV recognized simple or quaternary epitopes on E protein was examined. A recombinantly expressed monomeric ectodomain of ZIKV E protein (ZIKV E80) was purified, immobilized onto beads and used to deplete all ZIKV E80-binding antibody from plasma from the primary ZIKV subjects. Confirmation ELISA demonstrated a loss of ZIKV E80 binding activity (FIG. 20A), but retained IgG binding to intact virions (FIG. 20B), albeit at variably reduced levels compared to the un-depleted specimens. Compared to control depleted plasma, neutralization activity of ZIKV E80-depleted plasma was unaffected for DT172 and DT244, but exhibited a partial reduction in FRNT50 for DT168 and DT206 (FIGS. 20C-20D). As a positive control, plasma from each of the four primary ZIKV cases were depleted with ZIKV virus-like particles, which present all conformational epitopes of the intact virion. Complete loss of neutralization activity was observed (FIG. 20E). Taken together, these results indicate that primary ZIKV infection elicits a complex antibody response that includes populations of antibodies that are cross-reactive but non-neutralizing to DENV, as well as ZIKV type-specific neutralizing antibodies. Furthermore, ZIKV neutralizing antibodies target quaternary epitopes, though a minor fraction of neutralizing activity is attributable to antibodies that target epitopes largely contained on the E monomer in some individuals.

Figure 16:
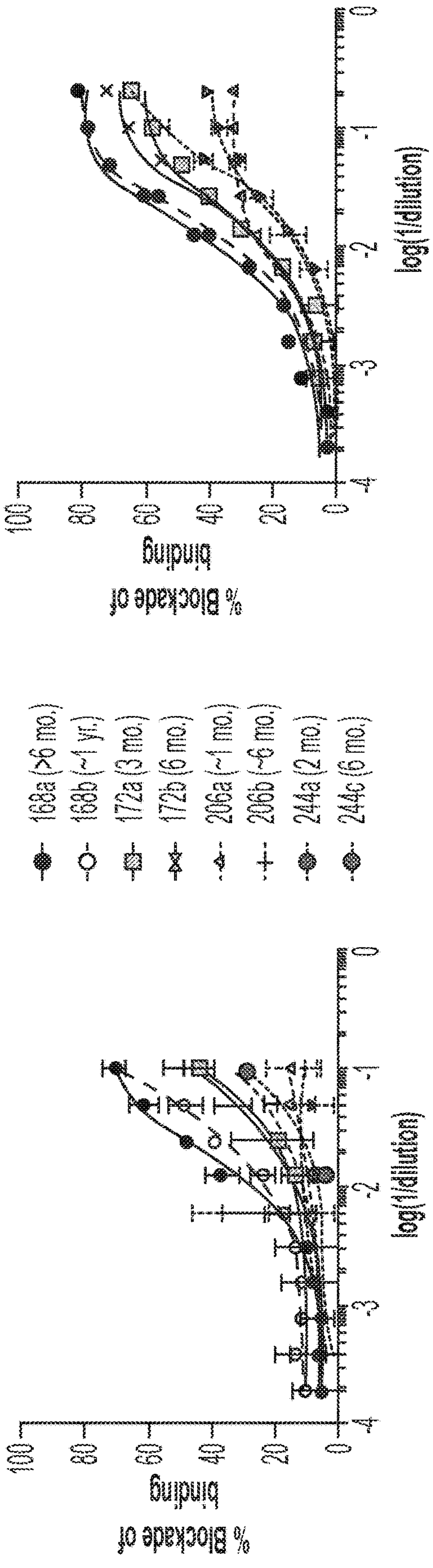
FIG. 16 shows the results of BOB assays using primary ZIKV infection human immune sera.
Figure 17:
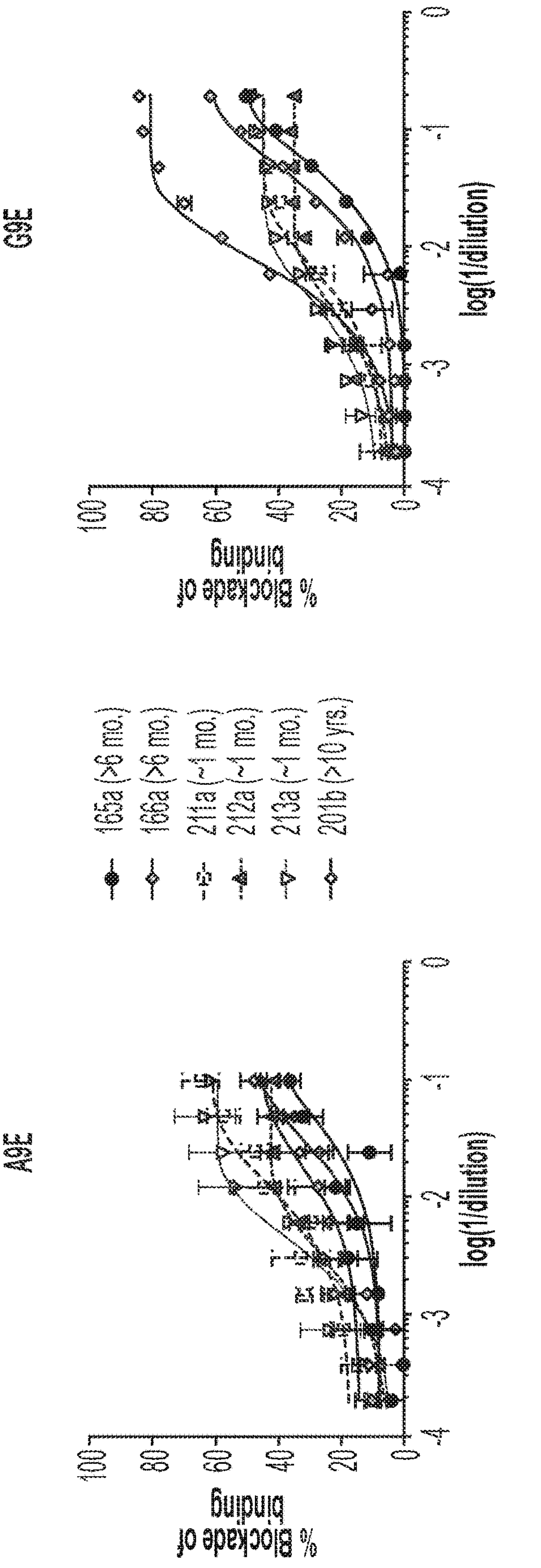
FIG. 17 shows the results of BOB assays using secondary ZIKV infection human immune sera.
Figure 18:
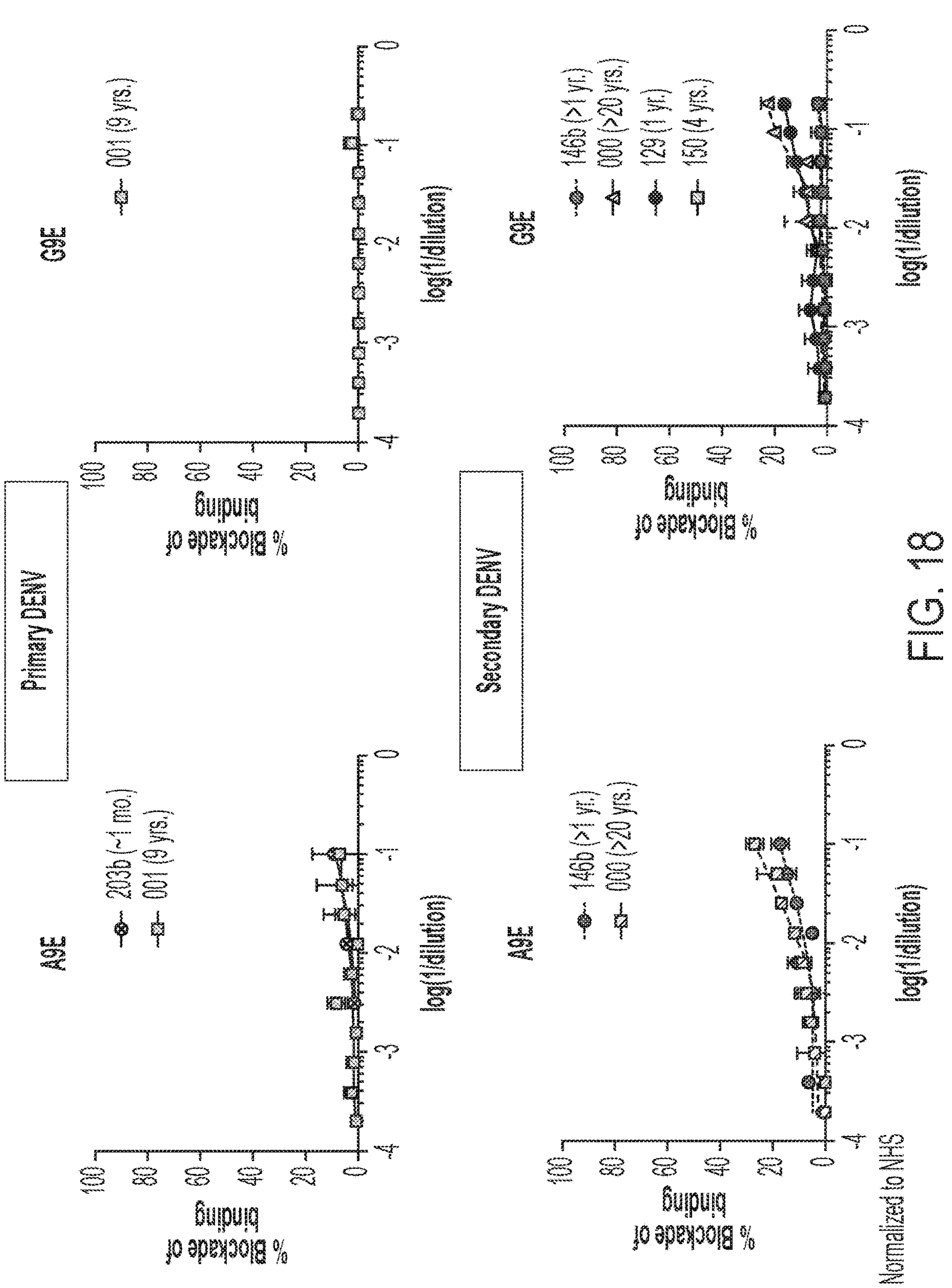
FIG. 18 shows the results of BOB assays using primary (top) and secondary (bottom) DENV infection human immune sera.
Figure 21:
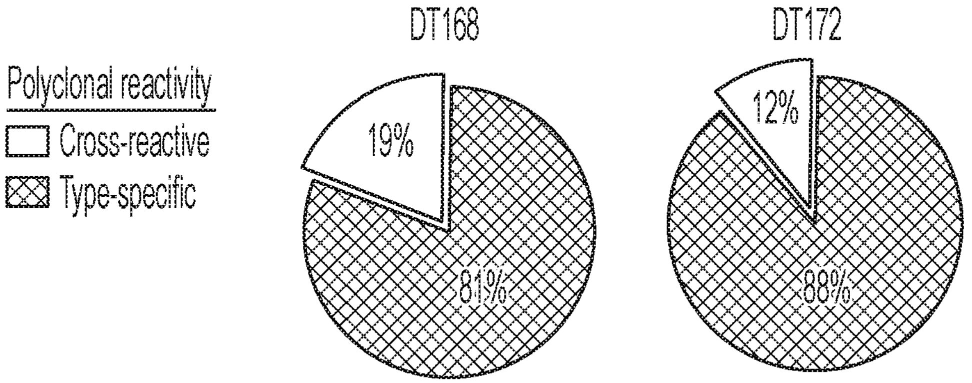
FIG. 21 shows the frequency of ZIKV-specific and cross-reactive MBCs. MBCs were transduced using the 6XL method and culture supernatants assessed for ZIKV- and DENV-binding IgG. The pie charts show the proportion of ZIKV-specific and cross-reactive wells for 2 donors with prior primary ZIKV infection (DT168, DT172). The table below delineates the raw numbers used to calculate the proportions shown in pie charts and the total frequency of ZIKV-reactive MBCs for each donor. ZIKV-TS wells, ZIKV type-specific, were designated when the IgG ELISA result for that well was positive for ZIKV and negative for DENV antigen. ZIKV-CR, ZIKV cross-reactive, wells were IgG-positive for both ZIKV and DENV antigen.

Long term humoral immunity that is attributable to memory B cells (BMCs) was assessed. To assess the MBC repertoire in individuals following primary ZIKV infection, memory B cells from the first two recruited subject, DT168 and DT172 were immortalized, as previously described (39). Immortalized MBCs were sorted into polyclonal cultures on 96-well plates at 50 cells/well. Supernatants of the polyclonal cultures were then screened for IgG binding to ZIKV and DENV1-4. The frequencies of antigen-specific memory B cells were estimated using the number of ELISA-positive cultures divided by the total number of immortalized MBC cultured. This calculation was based on the assumption of stochastic sampling during sorting and the average presence of one unique clone in the originating 50-cell polyclonal culture capable of producing IgG that yielded a positive ELISA signal. Across 480 polyclonal cultures (24,000 MBC clones), 267 cultures were ZIKV-reactive. The vast majority of these culture supernatants showed exclusive specificity to ZIKV (n=222, 83%), and a minority were cross-reactive to ZIKV and DENV (n=45, 17%) (FIG. 21). Screening of polyclonal culture supernatants revealed ZIKV-reactive BMC frequencies with a range of 0.2-1.0% (Table 2). BMCs from primary ZIKV cases produced antibodies that were almost entirely type-specific (FIGS. 16-18). ZIKV type-specific clones were also found to be readily detected on a Dengue-immune background, indicating that ZIKV immunity in secondary flavivirus infection is not dominated by cross-reactive BMC clones (Table 3). In particular, for DT168, the frequency of ZIKV-specific MBC was 1.2% of total MBCs, with 1% ZIKV type-specific and 0.2% ZIKV/DENV cross-reactive. DT172 was similar with 0.9% ZIKV-reactive MBCs, comprising 0.8% ZIKV type-specific and 0.1% ZIKV/DENV cross-reactive.

The monoclonal antibodies derived from a primary ZIKV cases are described below. The data indicates that ZIKV-specific neutralizing antibodies recognize complex structural epitopes present on the intact virion, but not recombinant E protein monomers.

TABLE 2

Screening Polyclonal MBCs for ZIKV-binding MBCs

| Donor | Serum Category | Time after symptom | Frequency ZIKV + in MBCs | DENV titer |
|---|---|---|---|---|
| DT165 | Secondary ZIKV | 8 mos. | 0.19% | Intermediate |
| DT166 | Secondary ZIKV | 8 mos. | 0.27% | High |
| DT168 | Primary ZIKV | 10 mos. | 1.03% | Low |
| DT172 | Primary ZIKV | 3 mos. | 0.92% | Low |

TABLE 3

Correlation between Prior Flavivirus Exposure and Lower Antigen-specific MBCs

| Donor | # hits | Time after symptom | # of MBCs screened | Freq. of MBC |
|---|---|---|---|---|
| DT165 | 28 | 8 mos. | 14,400 | 0.19% |
| DT166 | 25 | 8 mos. | 9,000 | 0.27% |
| DT168 | 148 | 10 mos. | 14,400 | 1.03% |
| DT172 | 88 | 3 mos. | 9,600 | 0.92% |

To better understand the molecular determinants of ZIKV neutralization, neutralizing monoclonal Abs (mAbs) were isolated and used for more detailed studies of virion-antibody interactions. Using single-cell sorting, monoclonal MBC cultures from ten polyclonal cultures with positive ZIKV ELISA binding signals for subject DT168 were established (Table 4). Approximately 40% of the single cell cultures were recovered as proliferating, IgG-producing cultures. Supernatants from monoclonal cultures were then screened for ZIKV-specific IgG. Half of the polyclonal cultures yielded ZIKV-reactive monoclonal cultures. Among monoclonal cultures from a given polyclonal progenitor culture, multiple positive wells were identified. For some monoclonal cultures (e.g. E3, H10, G11), all of the positive wells exhibited an extremely narrow range of values for ZIKV-binding (as assessed by optical density (OD) in ELISA) suggesting clonality, which was confirmed for E3 by sequencing all six ZIKV-specific subclones. This is consistent with the assumption that one clone in the original polyclonal culture was responsible for the initial positive signal. For E4- and D1-derived clones, positive monoclonal wells fell into two categories of OD values differing by >20%, each with very narrow (<10%) intra-group OD value range, suggesting two clones may have been present in the polyclonal culture. This was confirmed for D1 by sequencing one of the two potential clones and found two identical subclones of the "G9E" monoclonal culture. Taken together, these results support the finding that, on average, one clone in the 50-cell polyclonal culture produces a positive signal, thus validating the calculation for estimating ZIKV-specific memory B cell frequencies as above. Occasionally, multiple reactive clones may exist in the polyclonal culture. This is more likely to happen when the frequency of antigen-specific MBC is higher, and it would lead to potential underestimation of the antigen-specific MBC frequency. ZIKV IgG-positive reactive supernatants were then screened for neutralization activity. As before, subclones with tight OD values exhibited near-identical neutralization values.

TABLE 4

Derivation of Polyclonal and Monoclonal Memory B Cells from DT168
Subject DT168

| Polyclonal Cultures | | | Monoclonal Cultures | | | | | | | | |
|---|---|---|---|---|---|---|---|---|---|---|---|
| Well ID | O.D. (ZIKV)[A] | → | No. cells sorted | No. Viable cultures | Recovery | No. ZIKV+ wells | OD (ZIKV) of positives[A] (range) | Unique clones[B] | Frequency unique positive clones in polyclonal | No. ZIKV neutralizers (activity)[C] | Notes IGH/IGL sequencing |
| E3 | 0.60 | → | 120 | 12 | 10% | 6 | 0.32 ± 0.01 (0.3-0.35) | 1 | 2% (1/50) | 1 (84%) | ("A9E"): 6 identical subclones |
| E4 | 0.54 | → | 180 | 89 | 49% | 68 | 0.23 ± 0.03 (0.20-0.30) | 2 | 4% (2/50) | 1 (51%) | N.D. |
| F11 | 0.51 | → | 120 | 20 | 17% | 0 | — | — | — | — | N.D. |
| H10 | 0.49 | → | 120 | 53 | 44% | 5 | 0.25 ± 0.01 (0.25-0.27) | 1 | 2% (1/50) | 1 (58%) | N.D. |
| D1 | 0.49 | → | 120 | 77 | 64% | 13 | 0.34 ± 0.04 (0.30-0.40) | 2 | 4% (2/50) | 2 (83, 53%) | 1 of 2 clones sequenced (G9E)[D] |
| B3 | 0.46 | → | 120 | 18 | 15% | 0 | — | — | — | — | N.D. |
| D10 | 0.44 | → | 120 | 60 | 50% | 0 | — | — | — | — | N.D. |
| C3 | 0.42 | → | 120 | 52 | 43% | 0 | — | — | — | — | N.D. |
| G11 | 0.42 | → | 120 | 53 | 44% | 9 | 0.19 ± 0.02 (0.14-0.22) | 1 | 2% (1/50) | 1 (58%) | N.D. |
| F9 | 0.42 | → | 120 | 26 | 22% | 0 | — | — | — | — | N.D. |
| Mean ± s.d. or Totals | 0.48 ± 0.06 | | 1260 | 460 | 37% | 101 | 0.27 ± 0.06 | 7 | 2.8% (1.4/50) | 6 | |

[A]mean ± standard deviation of O.D. for ZIKV-binding ELISA (background = 0.1 - 0.15)
[B]= 1 if SD ≤ 10% of mean, = 2 if SD > 10% of mean, confirmed by sequencing of D1 and E3 clones
[C]Number positive is defined as ≥50% neutralization of ZIKV, % neutralization is presented in parentheses
[D]clone G9E with 83% neutralization was sequenced RNA was then isolated from monoclonal cultures producing the two most potent ZIKV-neutralizing mAbs (A9E and G9E) and assessed IgG isotype, light chain pairing, V gene usage, CDR3 length, and somatic hypermutations (SHM) by sequencing of Ig heavy and light chain gene products as described (Tables 4 and 5) (40). Two distinct mAbs were recovered. Both were IgG1 and both used Ig-k light chains and exhibited high levels of replacement SHM in their CDR regions compared to framework regions across IgH and IgL. The two mAbs were distinct in heavy chain V(D)J gene usage and CDR3 sequence. These unique mAb VH and VL sequences were inserted into IgG1/Ig-λ expression vectors, respectively, and IgG1 mAbs were produced in HEK-293F cells as described (40, 41).

TABLE 5

Sequence Characteristics of ZIKV-neutralizing mAb (Heavy Chain)

| | | Heavy chain | | | | | | | |
|---|---|---|---|---|---|---|---|---|---|
| | | Gene usage | | | HCDR 1-2-3 lengths | Non-silent | Non-silent: Silent SHM rates | | HCDR3 |
| Clone | Isotype | V | D | J | (AA) | SHM[A] | FR | CDR | AA sequence |
| A9E | IgG1,λ | V3-23*01 | D3-3*01 | J6*03 | 8-8-17 | 23 | 3.25 | 10 | ARSDFWRSGRYYYYMDV (SEQ ID NO: 5) |
| G9E | IgG1,λ | V3-23*01 | D1-14*01 | J4*02 | 8-8-21 | 13 | 0.83 | 8 | VGGSSAYNGDNGWREAASLDD (SEQ ID NO: 7) |

[A]SHM in nucleotide sequences assessed using IgBLAST from germline across FR1-CDR1-FR2-CDR2-FR3-CDR3

TABLE 6

Sequence Characteristics of ZIKV-neutralizing mAb (Light Chain)

| | | Light chain | | | | | | |
|---|---|---|---|---|---|---|---|---|
| | | Gene usage | | LCDR 1-2-3 lengths | Non-silent | Non-silent: Silent SHM rates | | LCDR3 |
| Clone | Isotype | V | J | (AA) | SHM[A] | FR | CDR | AA sequence |
| A9E | IgG1,λ | V2-14*01 | J2*01 | 9-3-11 | 18 | .86 | 4 | SSYSISSTLLV (SEQ ID NO: 6) |
| G9E | IgG1,λ | V3-14*01 | J3*02 | 9-3-10 | 11 | 1.2 | 1.7 | SSYTSRRTWV (SEQ ID NO: 8) |

[A]SHM in nucleotide sequences assessed using IgBLAST from germline across FR1-CDR1-FR2-CDR2-FR3-CDR3

Example 2. Antibody Binding Dynamics and Epitope Mapping

Figure 3:
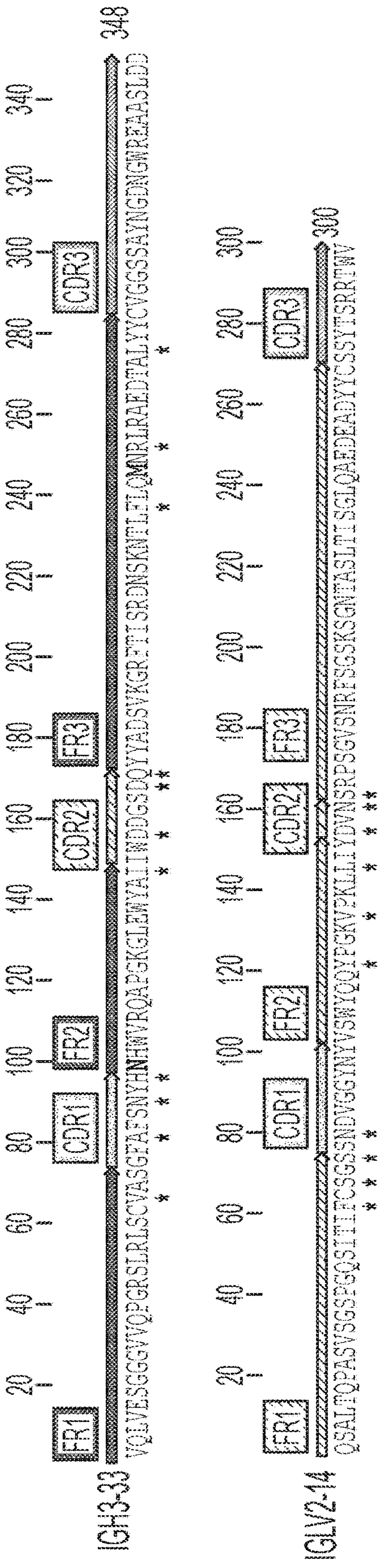
FIG. 3 is a schematic depicting the regions and sequences of G9E, a monoclonal antibody that neutralizes ZIKV. Asterisks denote somatic mutations. The sequences, from top to bottom are SEQ ID NO: 25 and SEQ ID NO: 26.
Figure 22A:
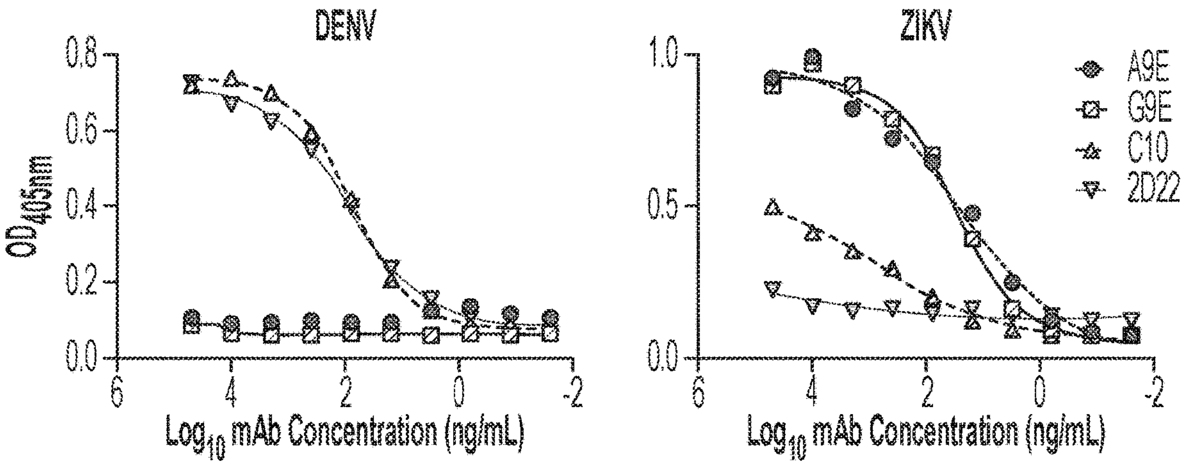
FIGS. 22A-22C show that the mAbs from primary ZIKV cases exhibit potent ZIKV-specific neutralization.
Figure 22B:
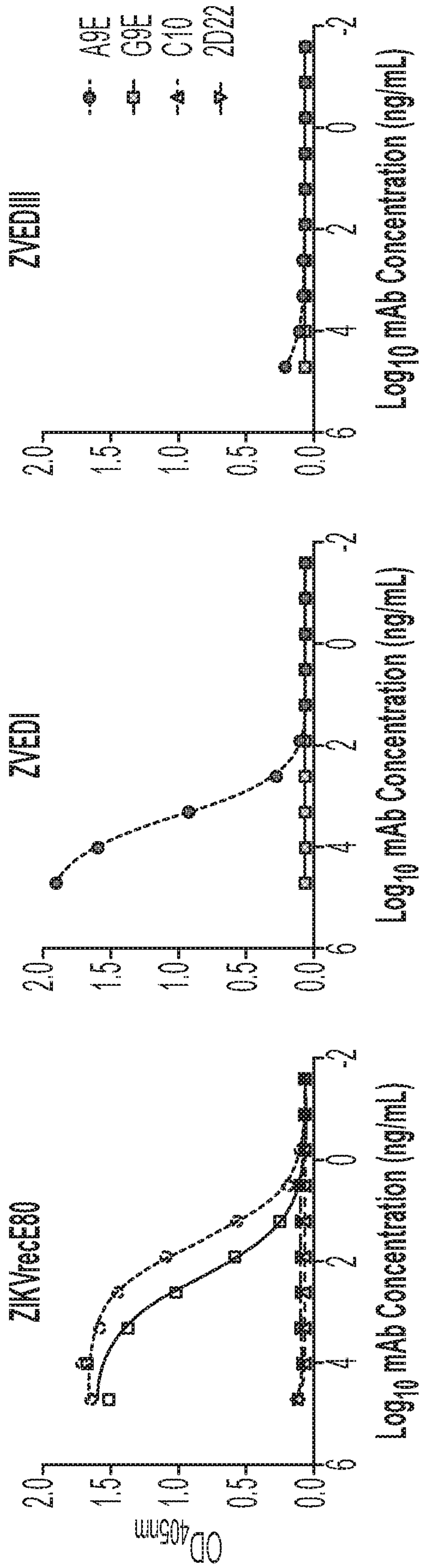
Figure 22C:
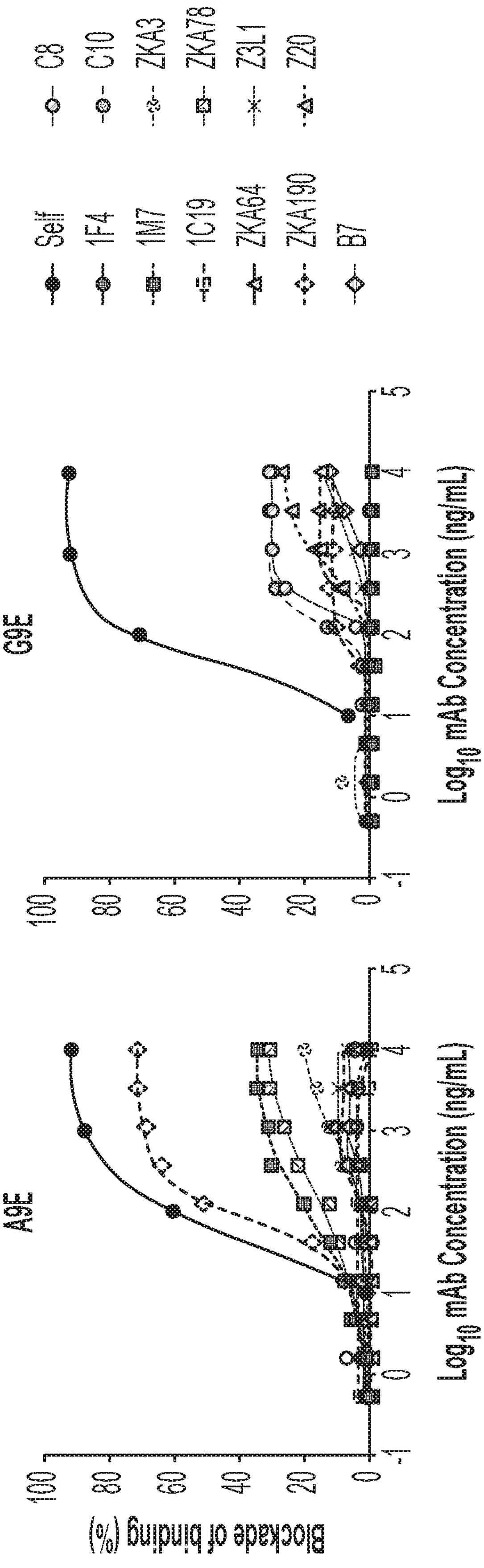

It was determined that two antibodies (A9E and G9E) were unique on the basis of CDR3 regions (FIGS. 1A, 11B, and 3), as described above. Both the A9E and G9E human mAbs bound ZIKV virions in an antigen capture ELISA, but did not bind to the four DENV serotypes (FIG. 22A), in accordance with the initial characterization of the polyclonal cultures from which these mAbs were derived. Surprisingly, both mAbs bound to recombinant ZIKV E80, and A9E bound to ZVEDI ($EC_{50}$=2500 ng/mL), albeit at higher concentrations compared to ZIKV E80 ($EC_{50}$=40 ng/mL). Neither mAb bound to ZVEDIII (FIG. 20B). Both mAbs were unable to bind DENV1-4, confirming ZIKV specificity. To identify the location of the epitope recognized by each mAb, competition assays were performed (hereafter referred to as blockade of binding (BOB)). A panel of six flavivirus cross-reactive and six ZIKV-specific mAbs were competed with A9E and G9E in BOB assays. DENV-specific mAbs were used as a control to establish 100% binding. As a positive control, unlabeled A9E or G9E mAb was competed with itself and showed a high level of auto-blockade (FIG. 22C). None of the DENV type-specific controls decreased the OD signal of A9E or G9E binding compared to control. Most flavivirus cross-reactive mAbs and ZIKV-specific mAbs failed to appreciably reduce the binding of A9E or G9E, with two notable exceptions. Both EDE1 mAbs C8 and C10 (42), which bind across domain II of E molecules paired in a homodimer, showed partial blockade of G9E. Additionally, ZV190, a human ZIKV-specific mAb known to bind to the EDI-III linker and lateral ridge of EDIII (43) strongly blocked A9E with a similar EC50 as A9E against itself. Neither of the two novel mAbs exhibited BOB activity against the other, indicating the two mAbs target distinct, non-overlapping epitopes.

Figure 2:
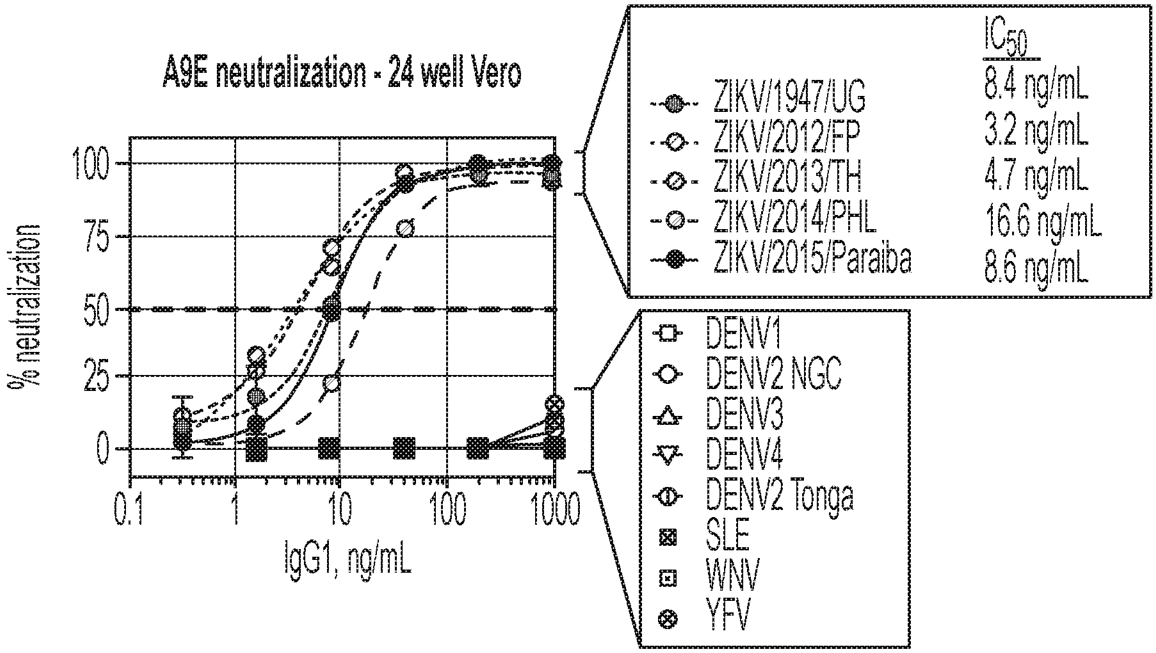
FIG. 2 shows the results of a 24-well Vero-based neutralization assay, demonstrating that recombinant A9E strongly neutralized all the ZIKV tested, but failed to bind or neutralize any of the other flaviviruses tested.
Figure 4:
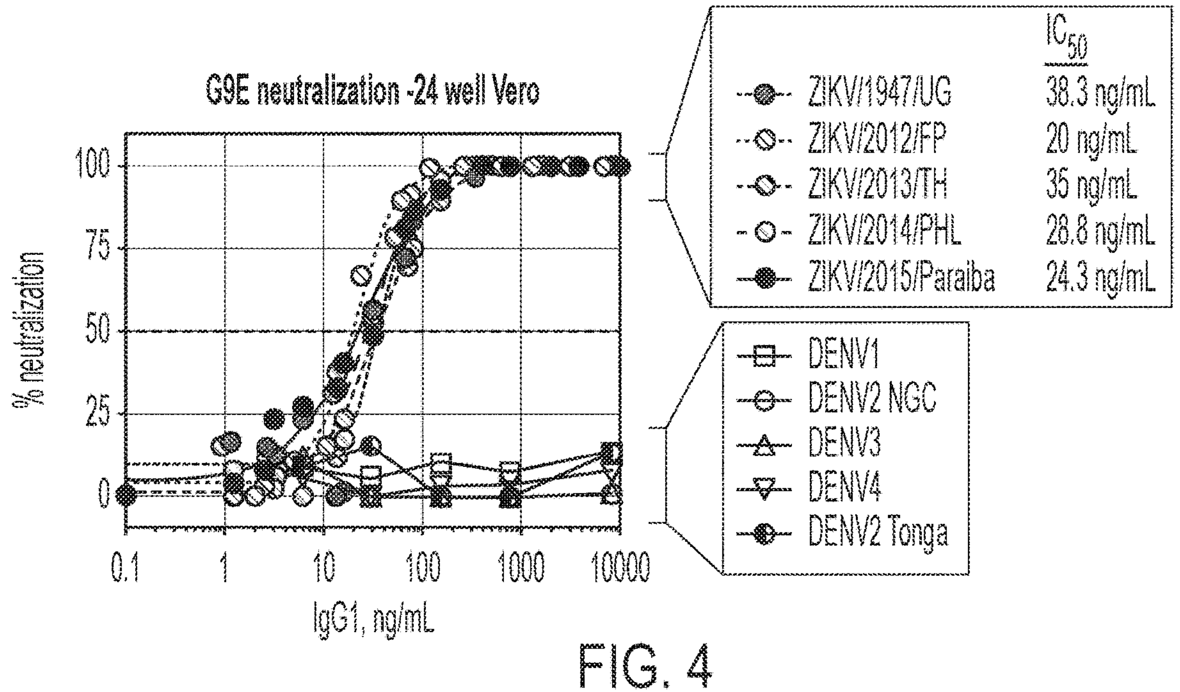
FIG. 4 shows the results of a 24-well Vero-based neutralization assay, demonstrating that recombinant G9E strongly neutralized all the ZIKV tested, but failed to neutralize any of the DENV serotypes tested.

Both antibodies were found to exhibit similar specificity for Asian and African lineages of ZIKV as opposed to any of the four DENV serotypes, St. Louis encephalitis virus, or yellow fever virus (FIGS. 2 and 4). A9E and G9E exhibited mean FRNT50 concentrations of 8.3 and 29 ng/mL across all ZIKV strains tested. The antibodies were screened further, and it was found that they are both potent (<100 ng/mL $IC_{50}$) to ultrapotent (<10 ng/mL $IC_{50}$) in vitro (assay-dependent) across both clades of ZIKV.

Figure 5A:
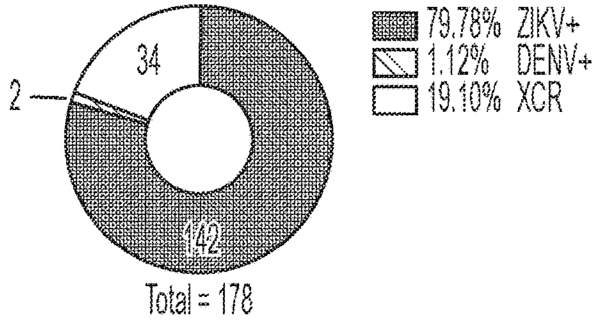
FIGS. 5A-5C show that A9E and G9E are strongly neutralizing Zika-specific monoclonal antibodies.
Figure 5B:
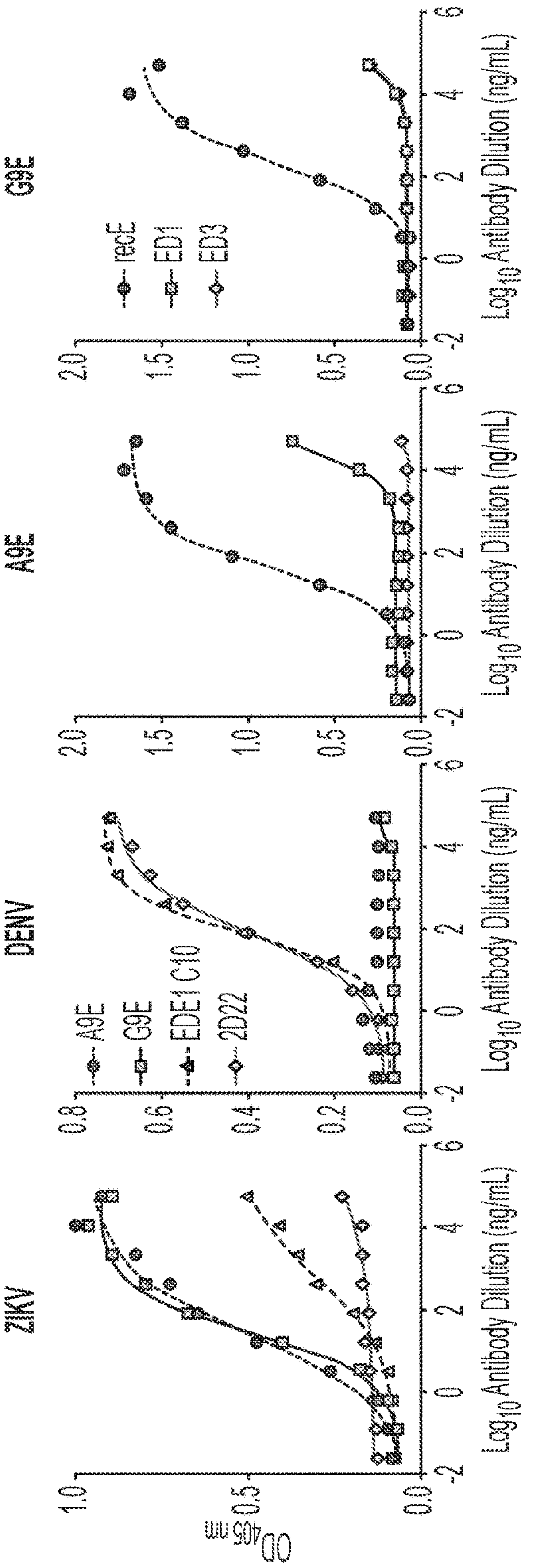
Figure 5C:
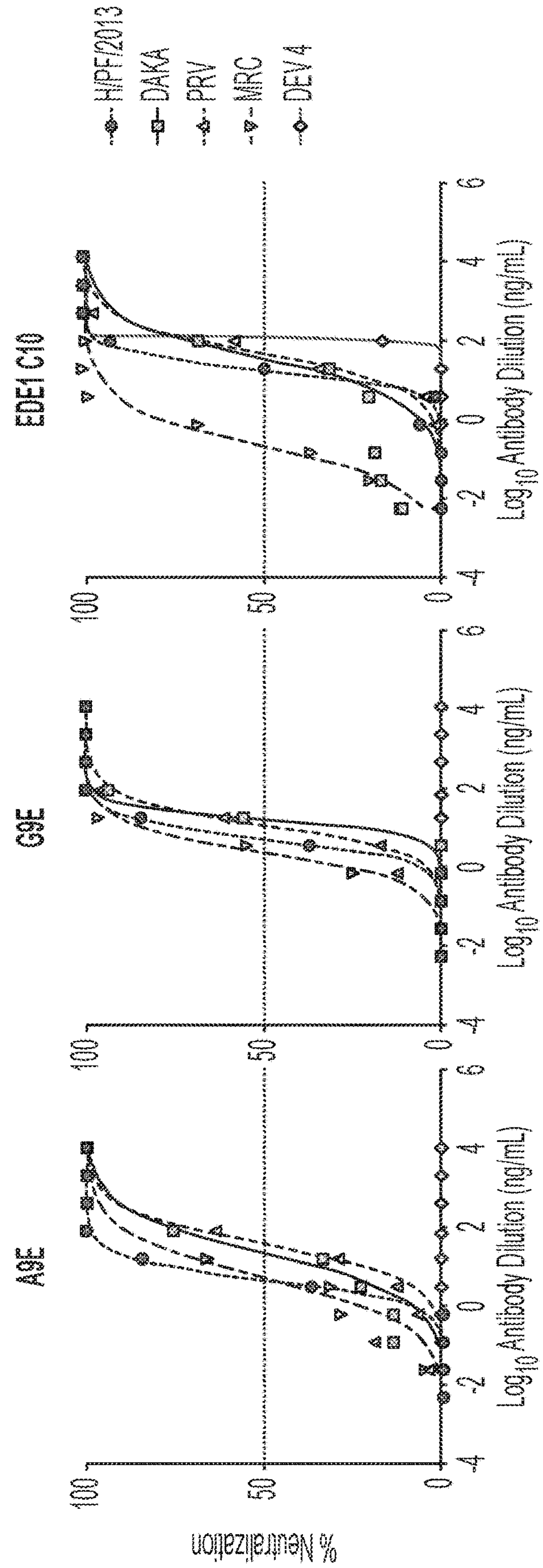

As shown in FIG. 5A, the fraction of total hits specific for DENV or ZIKV or cross-reactivity demonstrate that the ZIKV antibodies were not cross-reactive with DENV. Further, binding assays demonstrated that the two antibodies strongly neutralize ZIKV, while also being strongly ZIKV-specific (FIGS. 5B, 5C).

Example 3. In Vivo Experimentation

Figure 7:
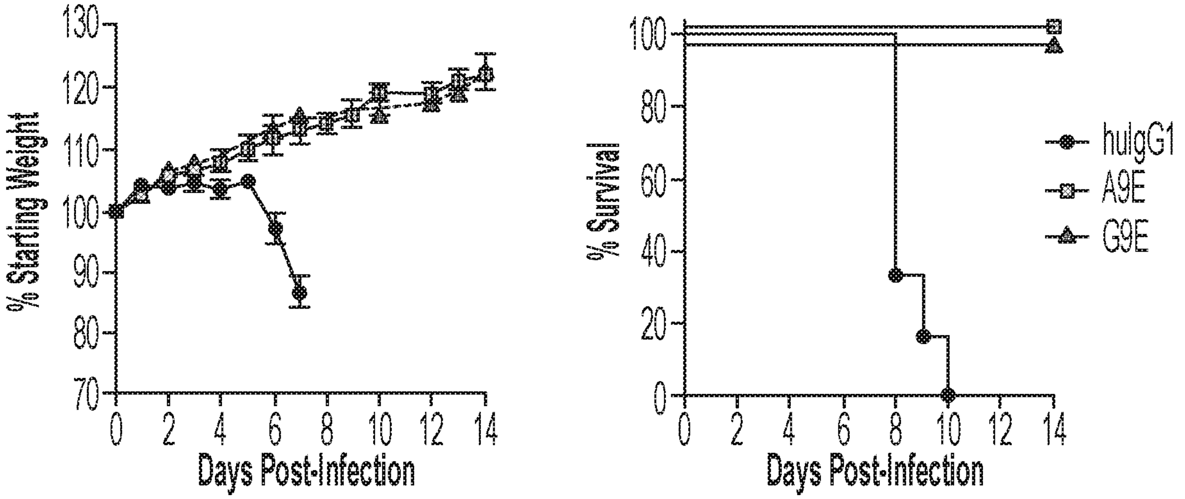
FIG. 7 shows in vivo data demonstrating that A9E (ZV1) and G9E (ZV2) protect against lethal ZIKV challenge. Four to six-week-old Ifnar$^{-/-}$ mice were treated with 200 μg of indicated A9E, G9E or polyclonal human IgG as a negative control on day −1 and challenged with 1000 FFU of ZIKV (H/PF/2013). Weight loss (left) and mortality (right) were monitored for 14 days post infection. Results represent 6 to 7 mice per group combined from two independent experiments. Weights are shown as mean±SEM and were censored upon the first death in the group.

The two candidate antibodies, A9E and G9E, were tested in vivo. Mice, Ifnar1$^{-/-}$, 5 weeks old (44) (n=6-7 per group over two experiments) were injected with 200 μg of the antibody or isotype control one day prior to receiving an footpad injection of 1000 FFU of H/PF/2013 Zika virus. The mice were monitored over 14 days. The results, shown in FIG. 7, demonstrate that both antibodies are protective against a lethal ZIKV challenge. None of the mice injected with either antibody died during the experiment, while all of the control mice, which were injected with the isotype control, lost weight and succumbed to infection by 8-10 days. Also, the weights of the mice were measured daily throughout the experiment. As shown in the right graph of FIG. 7, the mice which received antibody injections maintained and increased their weight throughout the experiment, whereas the control mice lost weight rapidly. Therefore, A9E and G9E were found to be protective against the lethal ZIKV challenge.

Example 4. Determination of Epitopes Recognized

Three methods were used to determine the epitopes recognized by the two antibodies: binding to recombinant ZIKV antigens, escape mutants, and blockade of binding (BOB) assays.

Figure 8:
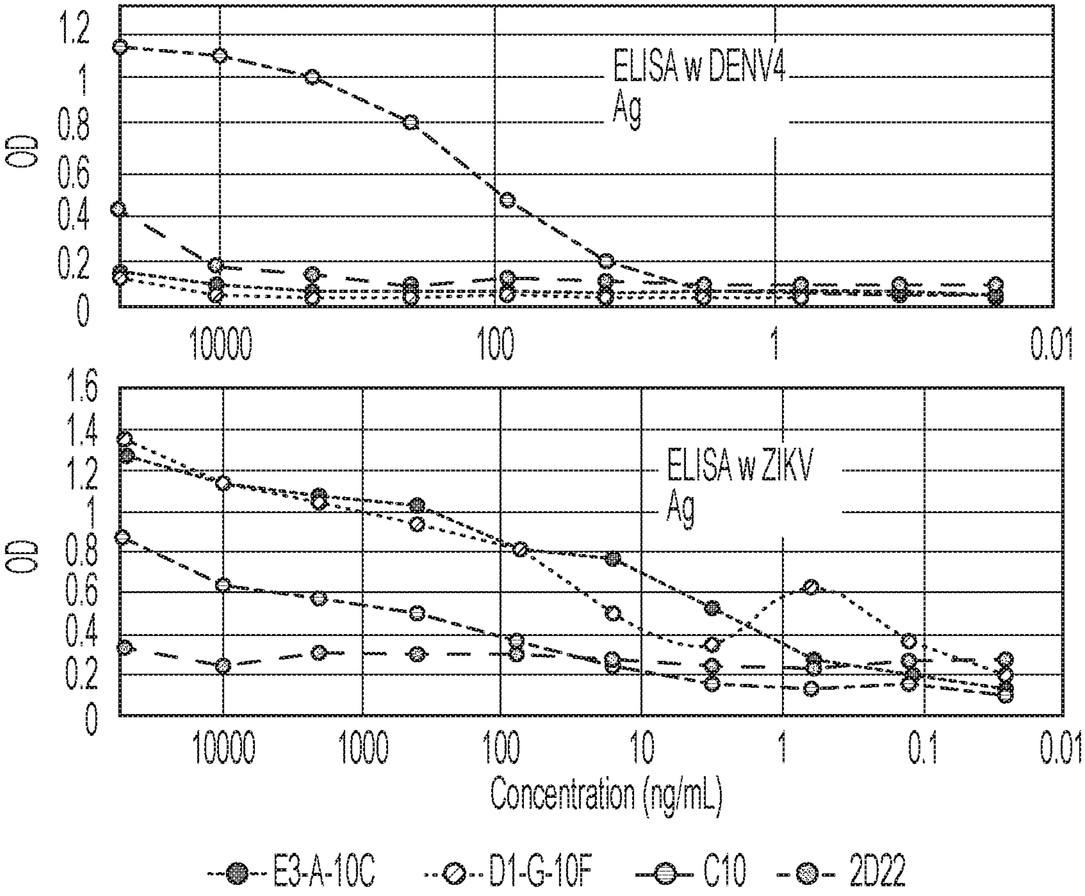
FIG. 8 shows that A9E (ZV1) and G9E (ZV2) bind ZIKV but not DENV virions. Note that C10 is a pan-flavivirus neutralizing antibody (an anti-envelope dimer epitope, EDE1) and 2D22 is a DENV2 antibody directed to a quaternary structure epitope (ED3).
Figure 9:
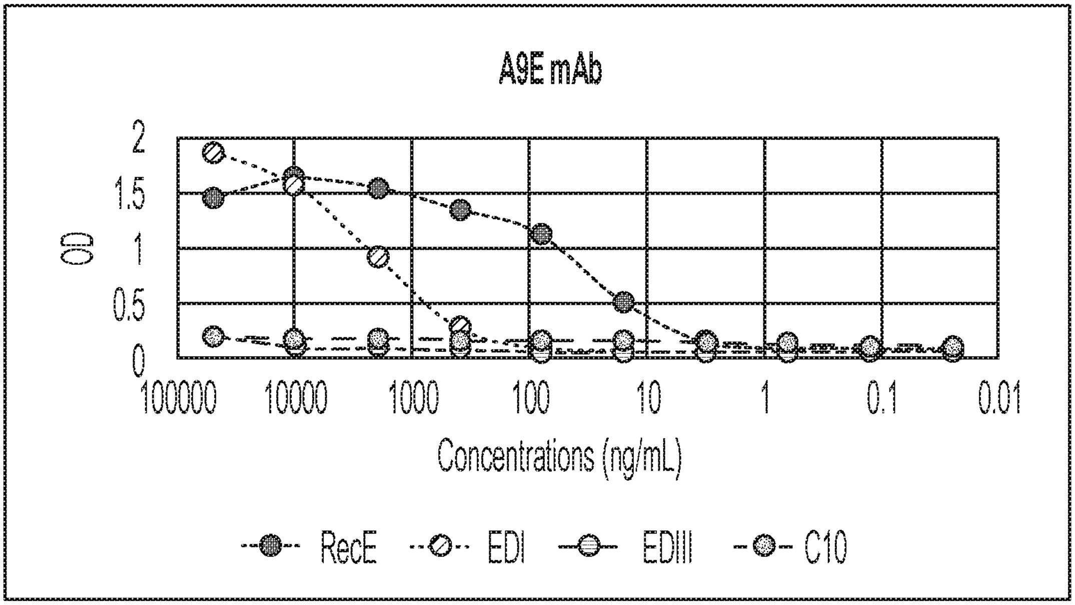
FIG. 9 shows that A9E (ZV1) and G9E (ZV2) bind recE (a recombinant monomer), and A9E binds the envelope domain 1 (ED1) of ZIKV.
Figure 9:
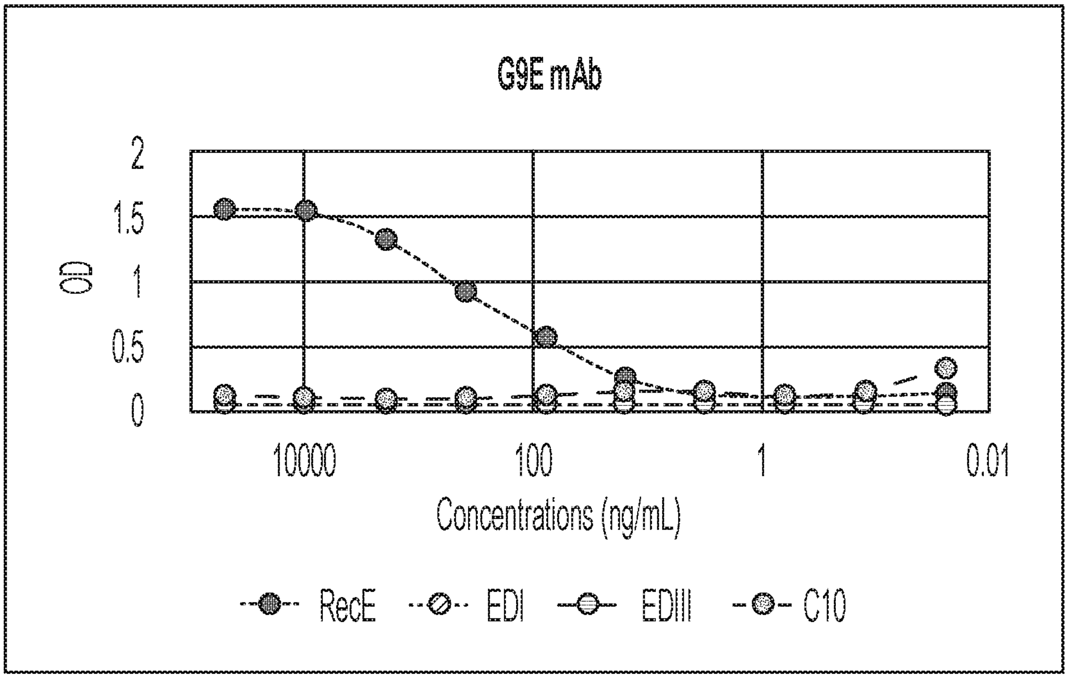

First, the binding of the antibodies to recombinant ZIKV antigens was examined. As shown in FIG. 8, both antibodies bind ZIKV but not Dengue virus (DENV) virions. Note that C10 is a pan-flavivirus neutralizing antibody (an anti-envelope dimer epitope, EDE1) and 2D22 is a DENV2 antibody directed to a quaternary structure epitope (ED3). The same binding assay was performed to examine each antibody's binding to ZIKV antigens. As shown in FIG. 9, both antibodies bind recE; however, A9E also binds ED1.

Figure 10:
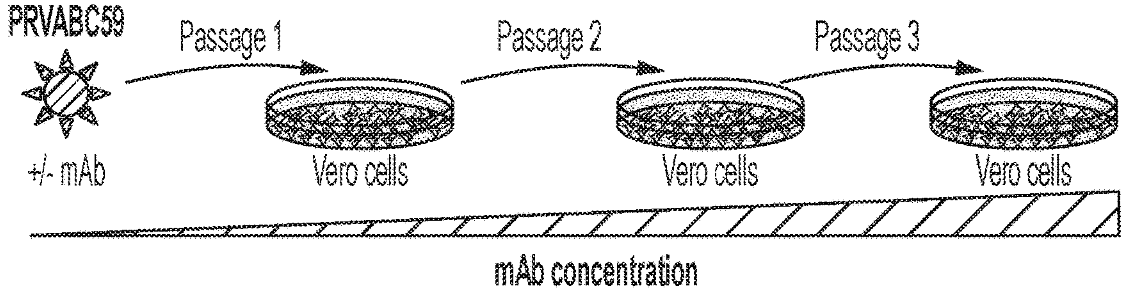
FIG. 10 is a schematic depicting the generation of escape mutants. Cells are monitored for signs of infection (a cytopathic effect) throughout the protocol. The supernatant is collected and checked for viral RNA using real-time PCR (RT-PCR).
Figure 11:
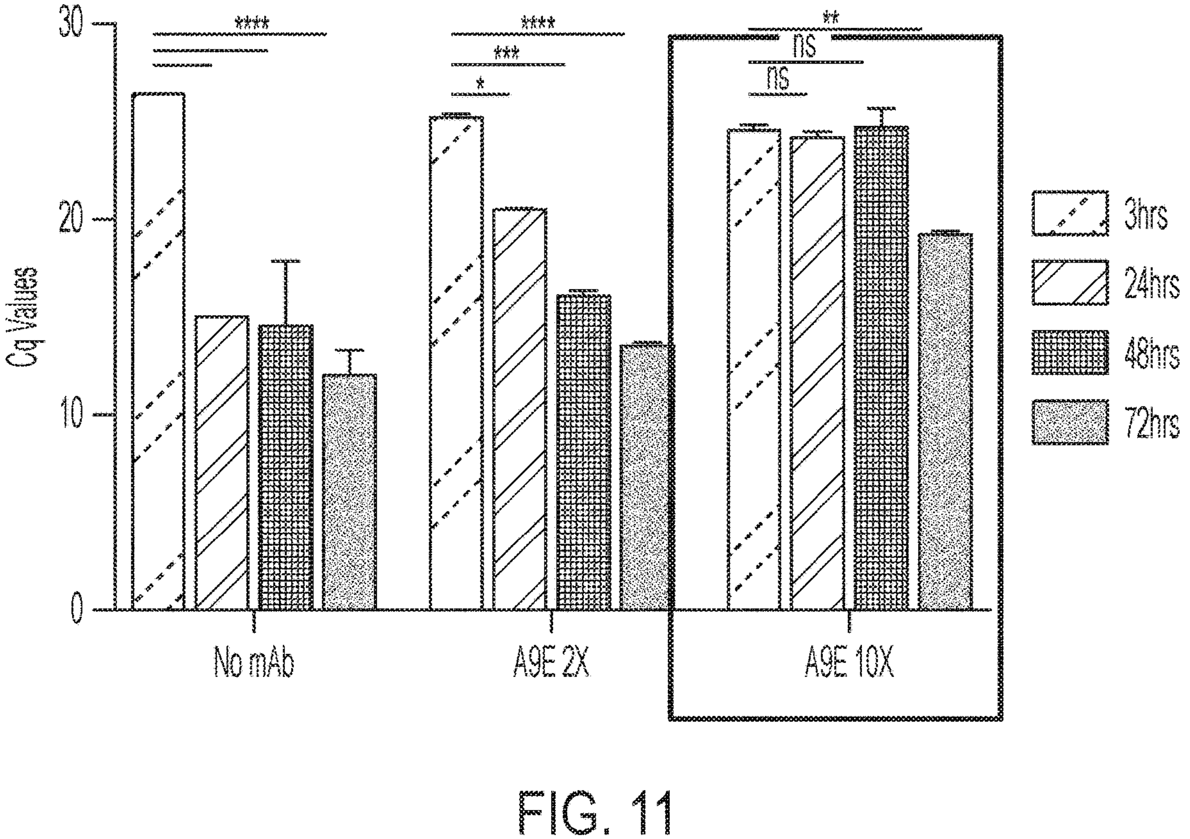
FIG. 11 is a graph showing the results of the first passage of cells as illustrated in FIG. 10, demonstrating that ZIKV grown the presence of A9E shows signs of neutralization escape.
Figure 12:
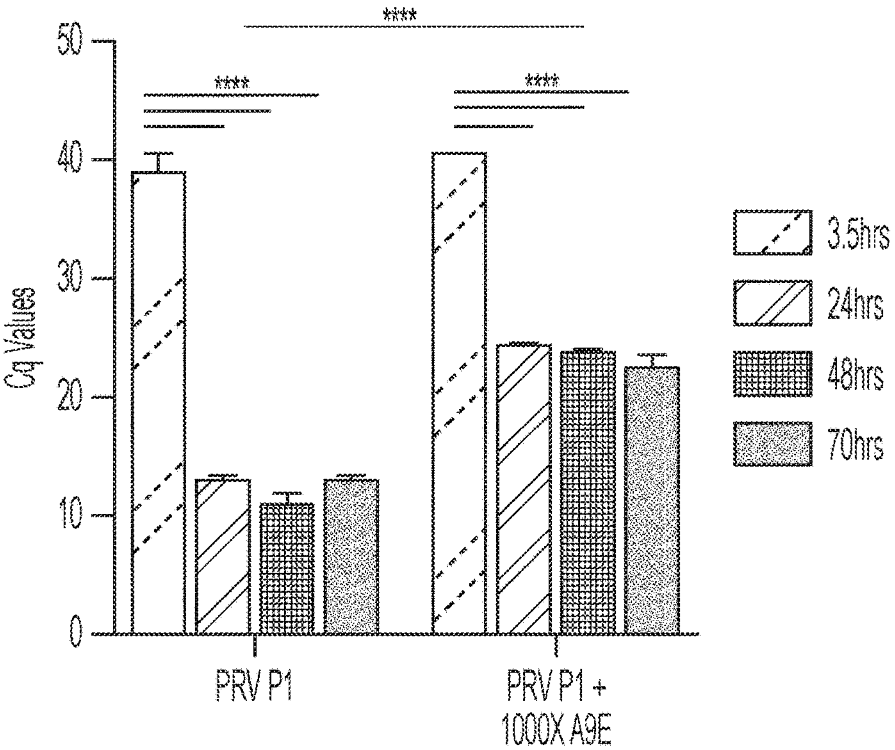
FIG. 12 is a graph showing the results of the fourth passage of cells as illustrated in FIG. 10, showing that the escape virus can grow in the presence of a high concentration of A9E.
Figure 13:
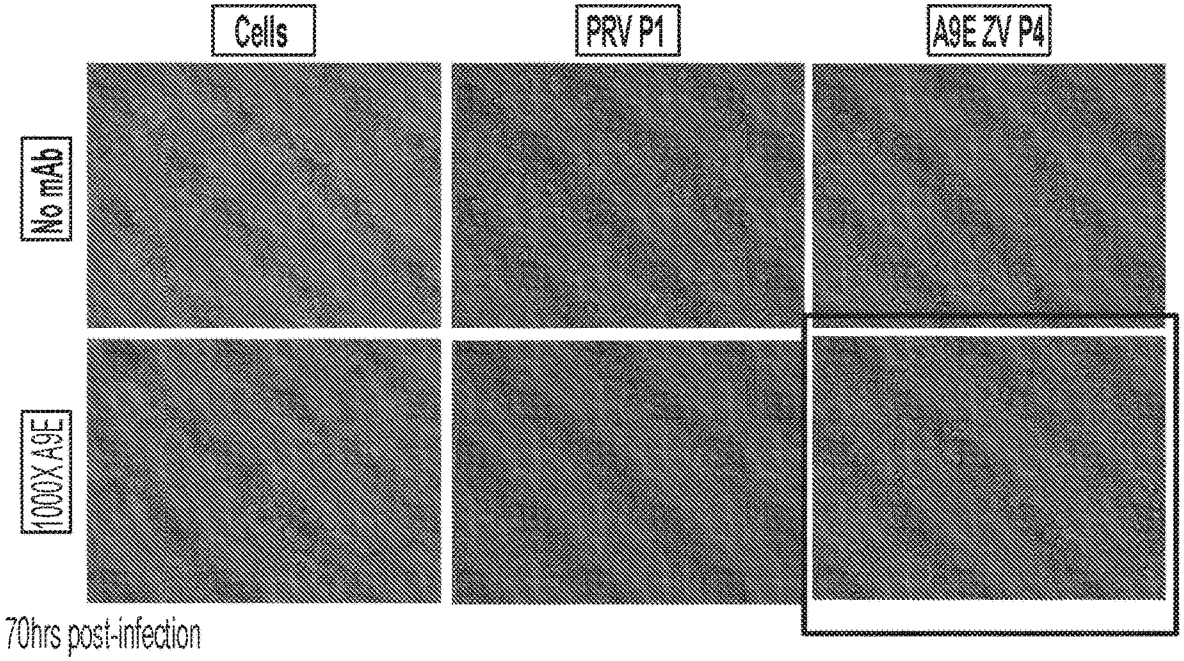
FIG. 13 shows microscopy images, demonstrating that the escape virus can grow in the presence of a high concentration of A9E. The images were taken 70 hours post-infection.
Figure 14:
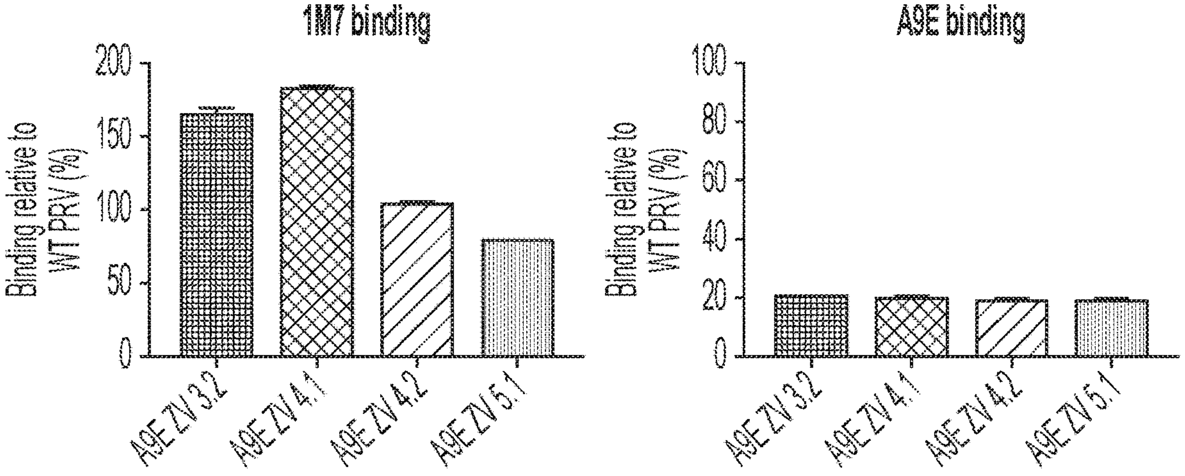
FIG. 14 is two graphs, showing that A9E does not bind to the escape virus.
Figure 23A:
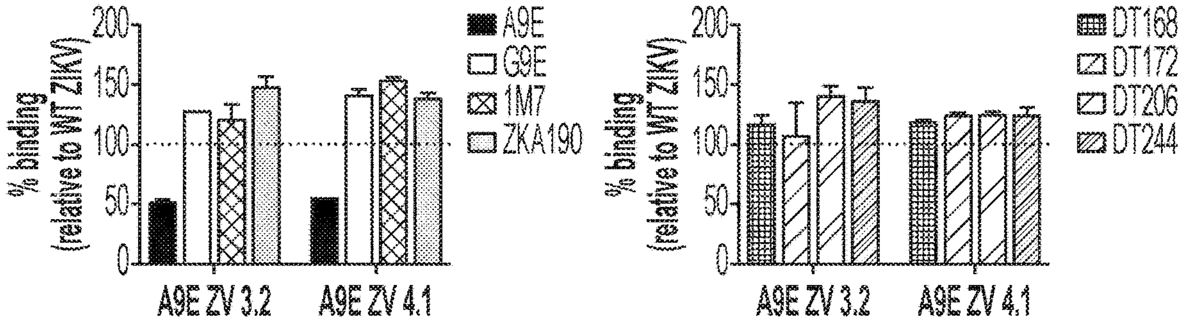
FIGS. 23A-23E show epitope mapping of ZIKV neutralizing mAbs.
Figure 23B:
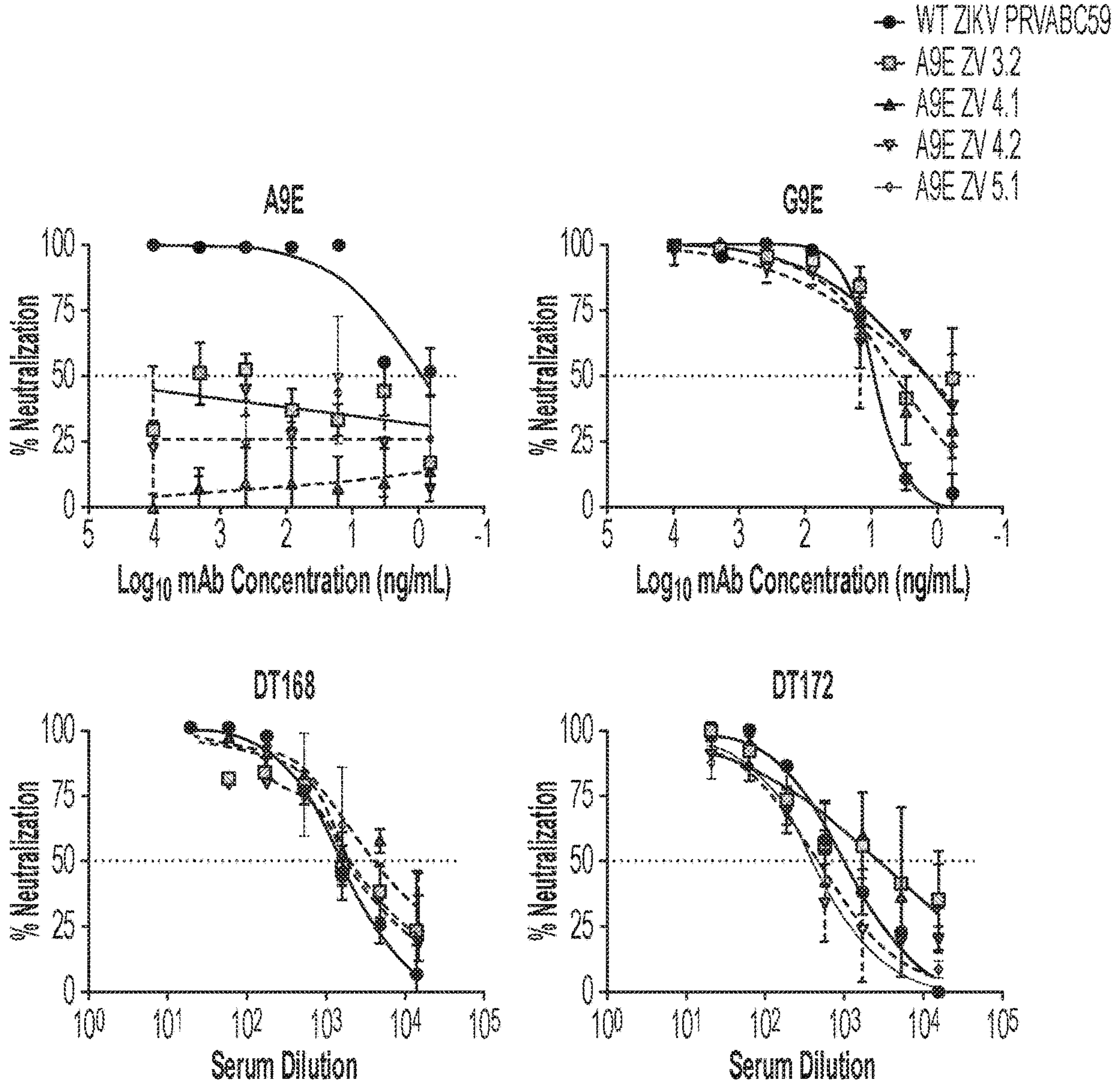
Figure 23C:
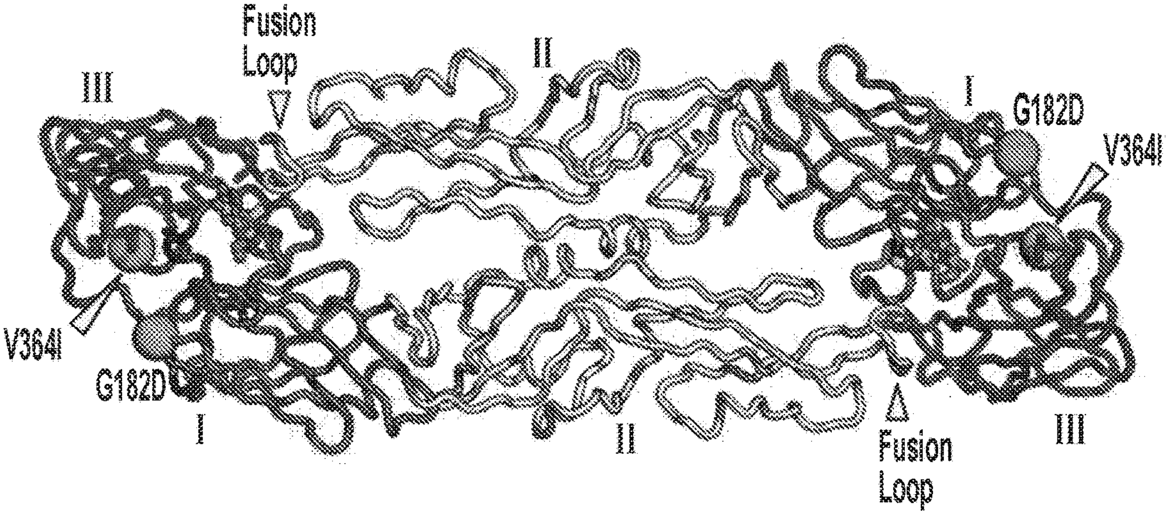

Epitopes were also examined using escape mutants. FIG. 10 schematically depicts the assay. PRVABC59 (a Zika virus strain) was propagated in Vero cells in the presence and absence of the candidate antibodies. As shown, the antibody concentration was increased with each cell passage. No escape virus that could tolerate increasing concentrations of G9E was isolated, even when beginning the process with concentration of G9E as low as 20.6 ng/ml. In contrast, for A9E, an escape virus was isolated after three rounds of passage that could be propagated in the presence of 35,800 ng/mL A9E mAb (approximately 780×FRNT50). Cells were monitored for signs of infection (cytopathic effect), and the supernatant was collected. The supernatant was screened for viral RNA using real-time PCR (RT-PCR). Viral isolates were plaque purified to generate clonal stocks. Two viral isolates were tested for binding by mAb and plasma (FIG. 23A), and four isolates were tested for neutralization escape (FIG. 23B). Isolate nomenclature is as follows: passage 4 and 5 from experiment 1=A9E ZV 4.1 and A9E ZV 5.1, and passage 3 and 4 from experiment 2=A9E ZV 3.2 and A9E ZV 4.2. As shown in FIG. 11, ZIKV grown in the presence of A9E displayed signs of neutralization escape, especially at higher concentrations of the antibody. Binding was retained by G9E, 1M7, and ZKA190 as well as by all four primary ZIKV polyclonal plasma. A9E failed to neutralize all 4 escape mutants compared to potent neutralization of the WT positive control. However, G9E and two polyclonal primary ZIKV-immune plasma neutralized all 4 mutants similarly to WT virus. FIG. 12, which shows data from passage 4, demonstrates that the escape virus can grow in the presence of a high concentration of A9E. This is further demonstrated with microscopy images in FIG. 13. Further, antigen titration experiments confirmed that A9E does not bind to the escape virus (FIG. 14). The A9E mutations were found to map to ED1 and the linker region between ED1-ED3. In particular, mutant viruses were sequenced and aligned to WT, with two mutations, one in EDIII (V364I) and the other in EDI (G128D) detected as depicted in FIG. 23C.

Figure 6A:
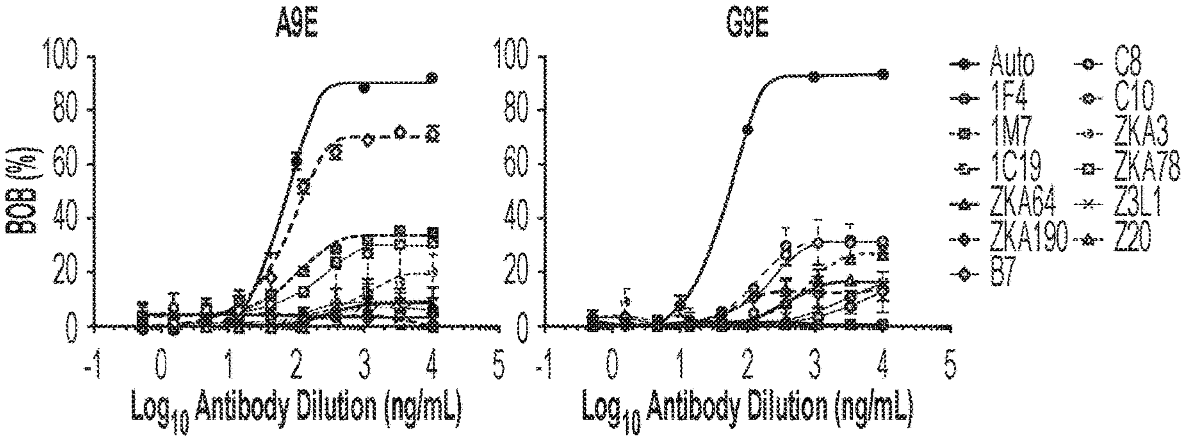
FIGS. 6A-6B show that Zika monoclonal antibodies have distinct specificities, which are conserved among Zika-immune plasma. Blockade of binding (BOB) assays were performed with Zika antigen capture ELISAs, which were pre-incubated with serial dilutions of either monoclonal antibodies (FIG. 6A) or plasma (FIG. 6B) from Zika-immune subjects at one month (FIG. 6B, top row) or 3 months (FIG. 6B, bottom row) post-infection, before adding alkaline phosphatase-conjugated A9E or G9E. BOB values indicate the percent reduction of OD as compared to a negative control.
Figure 6B:
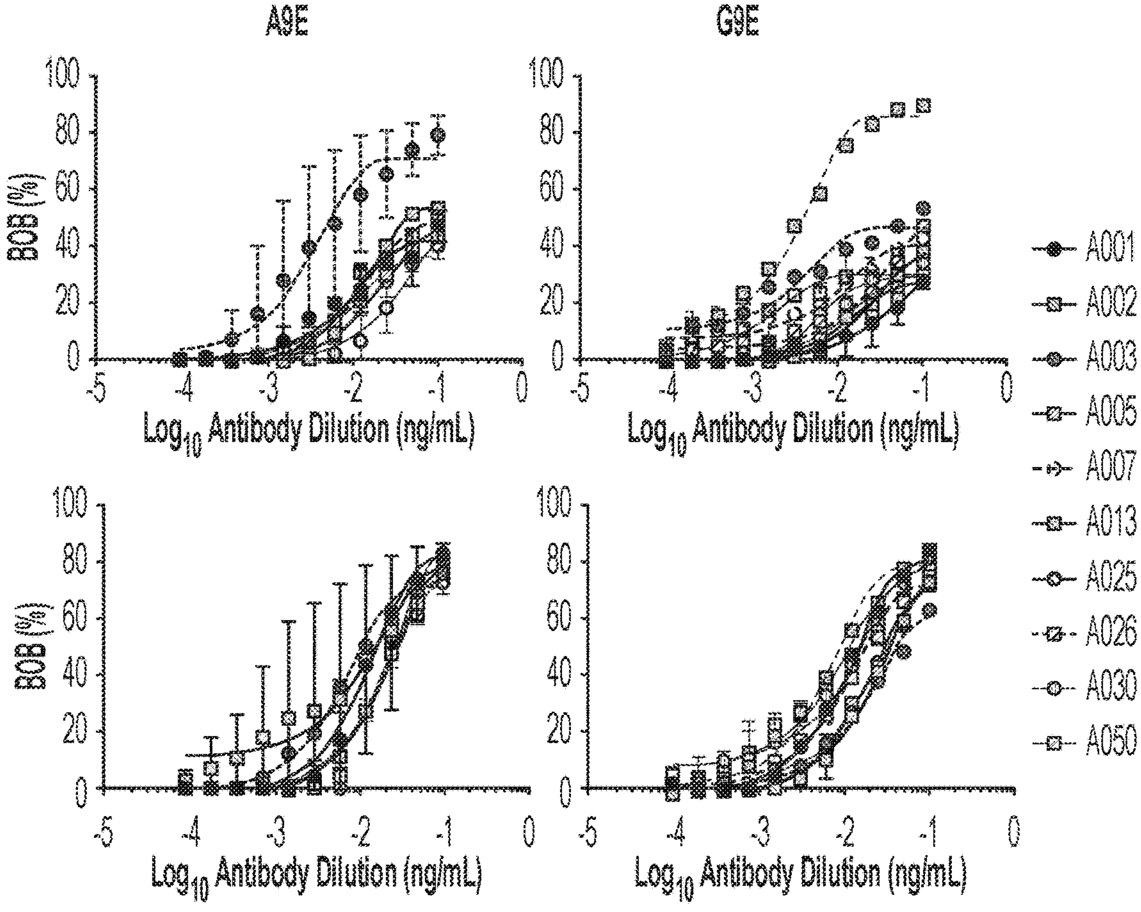
Figure 15:
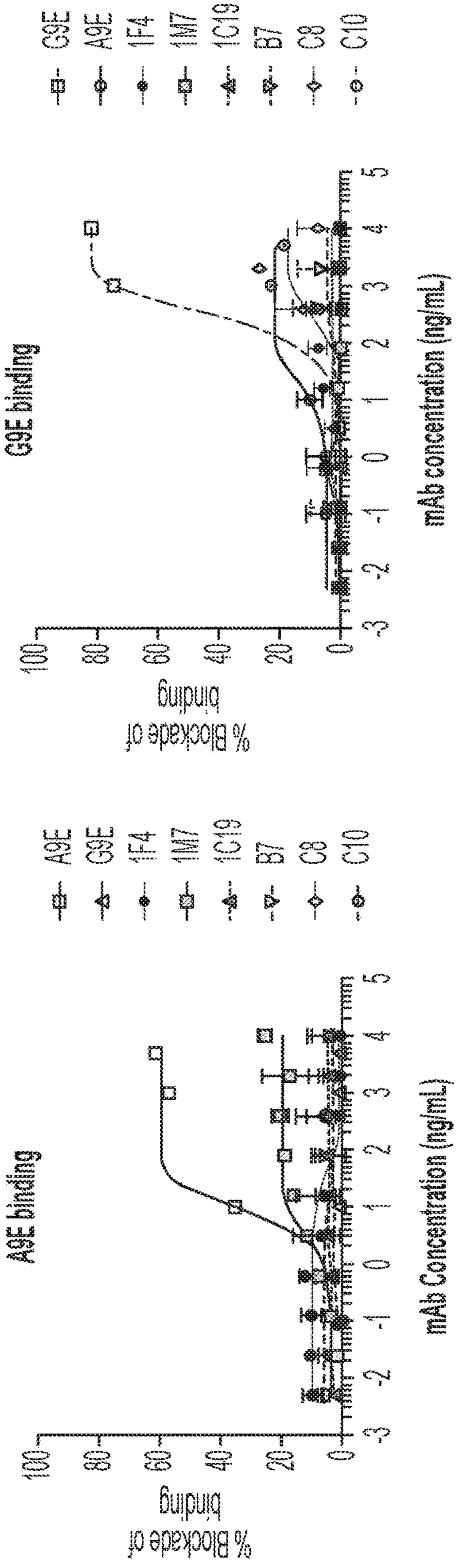
FIG. 15 shows the results of a blockade of monoclonal antibody binding (BOB) assay. A9E and G9E were found to bind to distinct epitopes.

The binding characteristics of A9E were further examined using a blockade of monoclonal antibody binding (BOB) assay. As shown in FIGS. 6A, 6B, and 15, A9E and G9E bind to distinct epitopes. The Zika antibodies have distinct specificities, which are conserved among Zika-immune plasma (FIG. 6B).

The BOB assay was also used to determine whether the epitopes of A9E and G9E were present in primary and secondary ZIKV serum. FIG. 16 shows that, in people exposed to primary ZIKV infections, the resulting antibodies bind to the epitopes defined by these antibodies. The blockade was found to be greater with respect to G9E, as compared to A9E. Similar results were seen in samples from individuals exposed to secondary ZIKV infections, although the difference in blockade between A9E and G9E was less pronounced (FIG. 17). In contrast, individuals who have had DENV infections do not have antibodies that compete with the binding of A9E and G9E to their epitopes on ZIKV (FIG. 18).

Figure 23D:
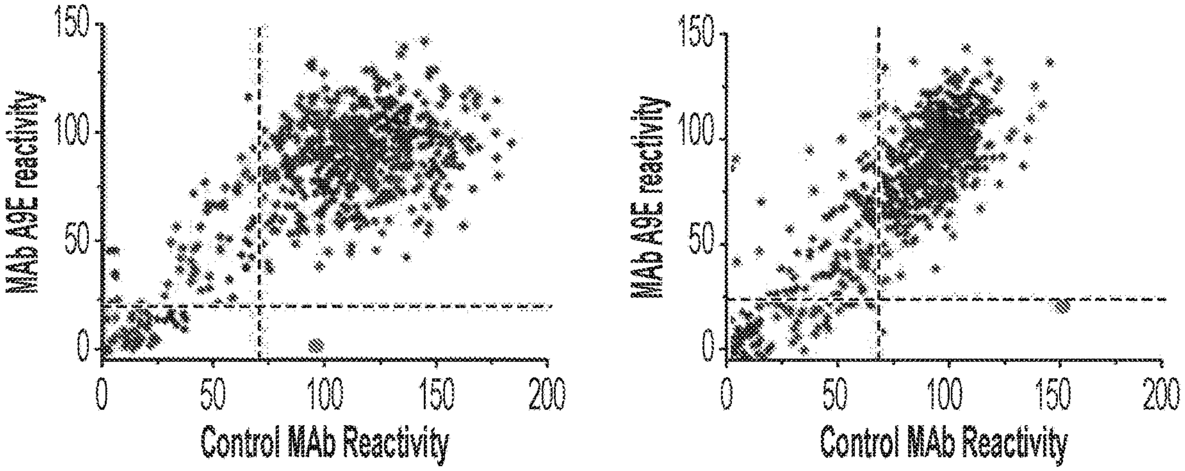
Figure 23E:
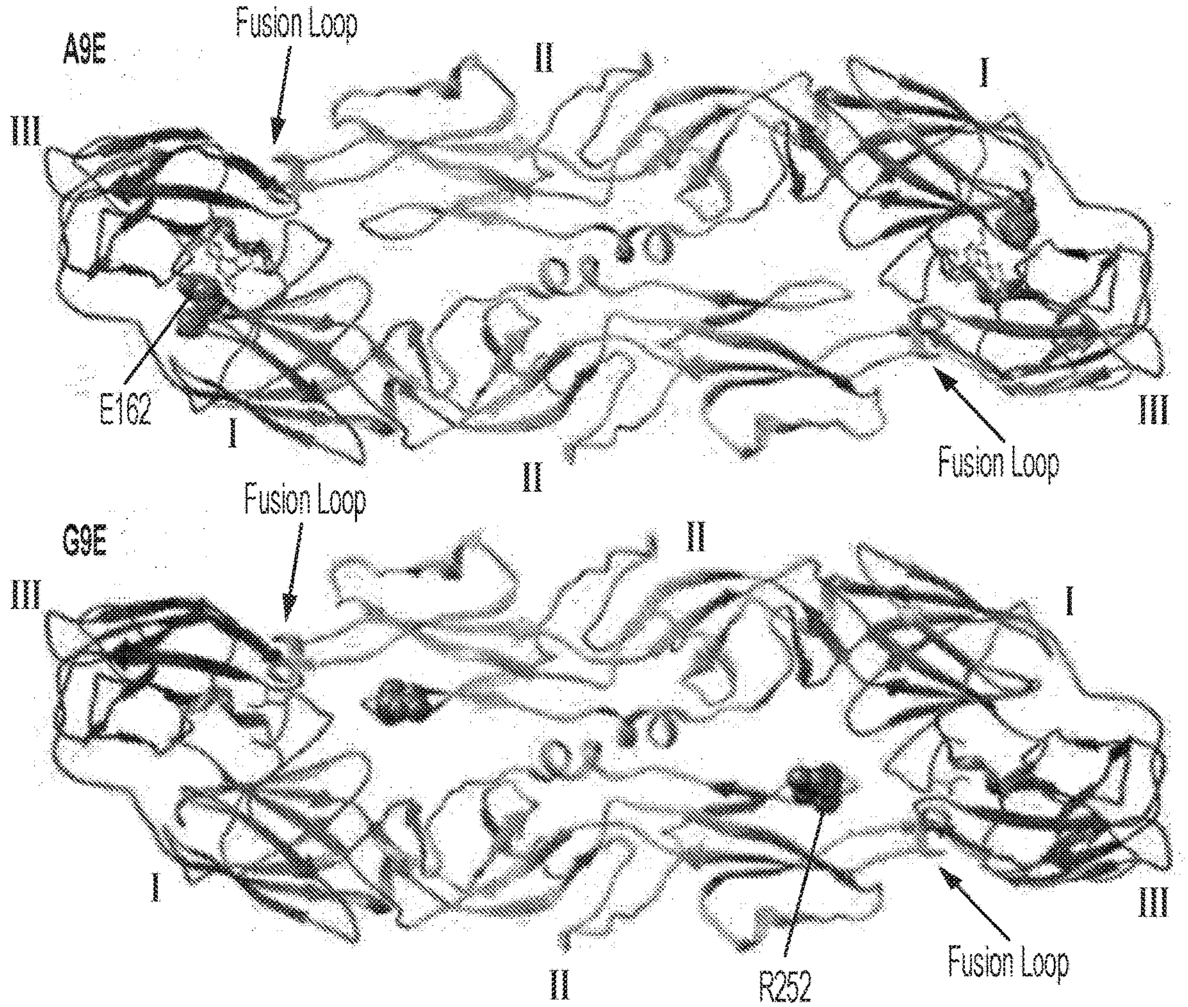

To map the epitopes engaged by neutralizing human mAbs by a complementary approach, both A9E and G9E were epitope-mapped using alanine scanning shotgun mutagenesis as previously described (FIG. 23D-23E) (45, 46). This approach compares mAb binding to a library of prM/E proteins with distinct point mutations to binding of control mAbs that normalizes for target protein expression and folding. One critical amino acid that significantly reduced binding was detected for each mAb. For A9E, loss of binding was observed with mutation of E162, which is within EDI, proximal to the glycan at N154. This result is consistent with the A9E escape mutant containing alterations in EDI and the partial binding of this mAb to ZVEDI. For G9E, mutation of residue R252 resulted in loss of G9E Fab binding.

Example 5. Representation of A9E and G9E in ZIKV-Infected Subjects

Figure 24A:
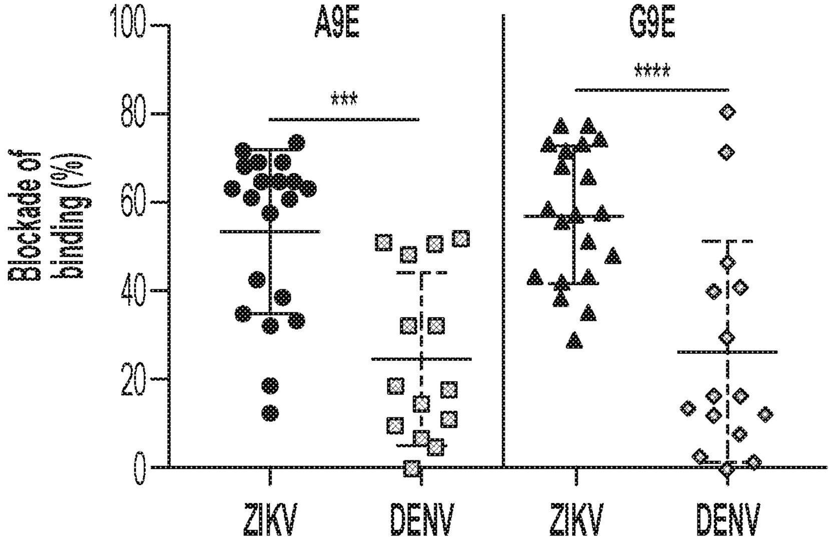
FIGS. 24A-24C show that A9E and G9E epitope binding are widely represented polyclonal plasma following natural ZIKV infection.
Figure 24B:
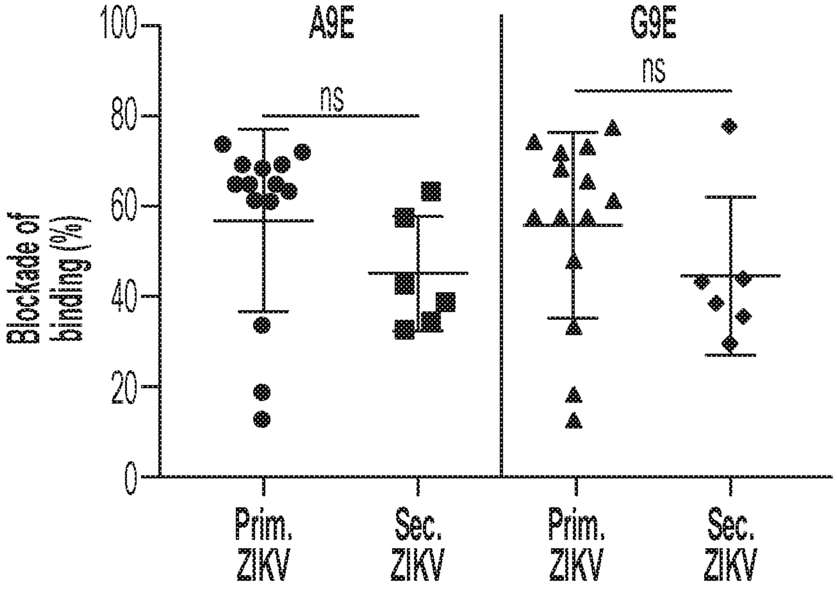
Figure 24C:
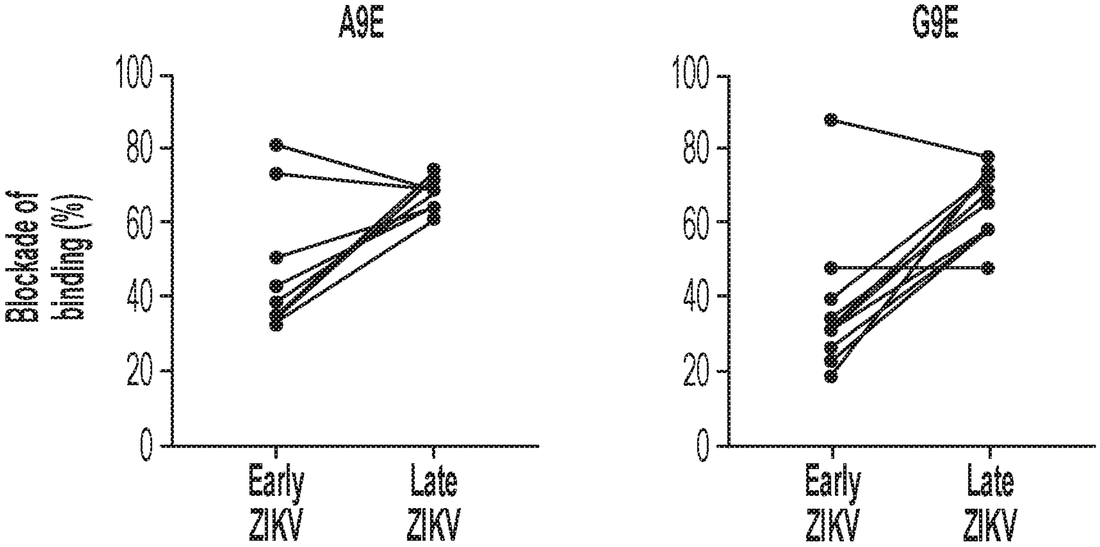

Based on escape mutations and alanine scanning mutagenesis, A9E and G9E recognize distinct epitopes contained on ZIKV E. To test whether the epitopes engaged by A9E and G9E are frequently targeted by polyclonal plasma antibody in natural ZIKV infection and whether DENV infection could elicit cross-reactive antibodies that bind similar epitopes present on ZIKV, a set of DENV- and/or ZIKV-immune plasma were competed against each mAb in BOB assays. The sources of plasma included US travelers, PCR and serology-confirmed ZIKV cases from Le6n, Nicaragua, and subjects from a Sri Lankan hospital-based cohort with PCR-confirmed DENV infection. The majority of DENV-immune plasma failed to block mAb binding to ZIKV at a level greater than 20% (FIG. 24A). The samples collected from DENV-immune plasma that showed greater than 40% blockade were collected during early convalescence when cross-reactive antibodies were higher. Plasma specimens from ZIKV-infected individuals were further analyzed by dividing them into primary vs. secondary flavivirus infection (FIG. 24B) and there was no difference in the level of blockade between the two groups. Plasma from DT168 exhibited greater than 70% blockade for each mAb; this was the highest level of activity among the 4 primary ZIKV-immune traveler plasma as expected, given that both mAbs were derived from DT168 PBMCs. When testing multiple specimens from the same donor at different times, the later specimen tended to have higher BOB activity. DT206 and DT244 exhibited negligible BOB against A9E early (even through FRNT50 titers are high), but began to show blockade (~30%) by 6 months post infection. This suggests that BOB activity of plasma may be affected by changes in the specificities represented in the antibody repertoire, not just the amount of IgG being produced. To further test this hypothesis, paired samples from ZIKV cases in Nicaragua were analyzed at 21 days and 6 months post infection and the trend for 8 out of 10 specimens was an increase in BOB at the later time (FIG. 24C). Taken together, these findings indicate that, following natural ZIKV infection, antibody responses targeting the same antigenic region of the potent ZIKV-specific neutralizing clones isolated are maintained into late convalescence.

Example 6. Discussion

This study shows that the polyclonal antibody response in ZIKV-infected individuals comprises a complex mixture of antibodies that recognize quaternary epitopes present on intact virion, and epitopes present on the recombinant ZIKV envelope protein monomer (simple epitopes). Furthermore, the data indicate that the majority of neutralizing activity in the four primary ZIKV plasma specimens is attributable to antibodies that recognize quaternary epitopes. However, in two of the four subjects, it was observed that antibodies targeting simple epitopes also contributed to plasma neutralizing activity (FIG. 20C). Similarly, other studies have identified ZIKV-serotype-specific mAbs, which target simple epitopes on recombinant envelope proteins, particularly on EDIII, and neutralize the virus at variable potency (34, 36, 49, 50). It has also been found that epitopes on EDI and EDIII are frequently targeted by ZIKV-specific antibodies (27). In DENV, it is known that EDIII-directed antibodies generally constitute a minor component of the human neutralizing antibody response (51). The same may be true of ZIKV. Taken together, these findings emphasize the contribution and protective role of quaternary epitope antibodies in ZIKV neutralization following primary infection.

To analyze humoral immunity in greater detail and elucidate the molecular determinants of neutralization, the memory B cell population from two subjects was examined, two distinct potently neutralizing mAbs were isolated from one of the subjects, their key binding determinants were mapped, and the representation of these two mAb specificities in a more general population was assessed. Approximately 1% of immortalized MBCs were ZIKV-reactive. This frequency is within the expected range for antigen-specific MBC responses to DENV (52) and ZIKV (53), suggesting adequate sampling of the memory B cell pool. The vast majority of antigen-specific MBC clones isolated from primary ZIKV cases were found to be ZIKV-specific and not cross-reactive to DENV. It has been shown that ZIKV infection in a DENV-immune host activates pre-existing, cross-reactive MBC responses (34-36), which means the repertoire selected when ZIKV is a primary vs. secondary flavivirus infection could be distinct and have consequences for virus control, clinical outcome, and transmission.

Identifying targets of the long-lived neutralizing antibody response is a fundamental requirement for vaccine development, as these may guide further antigen design as well as assessment of vaccine-induced immunity. The two potently neutralizing mAbs isolated in this study were found to bind to recombinant ZIKV envelope protein monomer. Depletion experiments (FIGS. 20A-20E) are consistent with subject DT168 having a neutralizing antibody response against ZIKV that recognizes both simple and complex structural epitopes.

A9E and G9E were found to recognize distinct epitopes based on the lack of competitive binding by each other and on different critical binding residues identified by complementary epitope mapping approaches. A9E binding was blocked by ZKA190, whose epitope spans the lateral ridge of EDIII and residues in the EDI/EDIII linker region. EDI likely contains part but not all of the A9E footprint based on ZKA190 competition and the weaker binding of EDI vs. ZIKV E80 exhibited by A9E. An escape mutant to G9E was not generated, possibly because the footprint of G9E includes at least one critical residue essential for viral fitness. G9E appears to bind residues primarily in EDII as mutagenesis revealed loss of binding with R252A, and this mAb did not bind monomeric EDI or EDIII. Moreover, BOB by EDE1 antibodies (C8 and C10) supports an epitope in EDII. Taken together, the data suggest that the epitopes of these two antibodies do not overlap.

Antigen-specific responses arise under the influence of a variety of host- and pathogen-specific features, which leads to certain responses being particular to an individual ("private") while others are more broadly represented in populations ("public"). The latter would need to be true and examined in order to track an antigen-specific response for vaccine development. In general, plasma antibodies from ZIKV-immune individuals (including those with and without prior DENV infection) competed with A9E and G9E for ZIKV virion binding. DENV-immune plasma seldom blocked binding of A9E and G9E to ZIKV, or it does so with substantially less efficiency. ZIKV-immune plasma from later times (>1 month and typically 6 months post infection) exhibited a greater degree of blocking activity. Overall, neutralization titers typically peak and decline before 6 months, which suggest that this effect is not simply due to total amount of IgG present in the plasma, but may involve ongoing shaping of specificities maintained in the antibody repertoire for months following acute infection. While these results do not prove that the exact epitope of either mAb is widely targeted in individuals with ZIKV infections, it does indicate that the region of the E protein surrounding the A9E and G9E epitopes appears to be highly immunogenic in human ZIKV infection.

Two ZIKV mAbs with potential for further development for therapeutic (43, 46) and/or diagnostic (56) purposes have been identified. The FRNT50 values of A9E (3-17 ng/mL) and G9E (20-38 ng/mL) are among the lowest reported for native human ZIKV mAbs. Multiple strains of ZIKV, representing African and Asian lineages, were effectively neutralized, consistent with the idea that ZIKV exists as a single serotype (57, 58). A9E and G9E both failed to bind or neutralize DENV, and both protected against murine lethal ZIKV challenge in vivo. The two mAbs appear to define epitopes that are consistently targets of the antibody response to natural ZIKV infection as evidenced by the BOB studies with an initial set of human plasma from ZIKV-infected individuals.

Example 7. Materials and Methods

Human Subjects and Biospecimen Collection

UNC Travelers: Plasma was collected from North Carolina residents with a history of or risk for arbovirus infection based on travel to endemic areas and self-reported symptoms and medical history. Plasma samples were tested by virus capture ELISA. DENV- or ZIKV-reactive plasma was further characterized by neutralization assays on Vero cells (see below) to verify prior flavivirus infection. Plasma that neutralized one DENV serotype or ZIKV with minimal neutralizing activity to other viruses were defined as primary flavivirus infections (meaning that the FRNT50 for a single DENV serotype or ZIKV is at least 4-fold higher than any other virus tested). In the ZIKV cases described herein, the travel history of the subject corroborated the primary ZIKV immune status. Secondary flavivirus infections were defined by the highest two or more FRNT50 values being separated by less than 4-fold activity. Existing plasma with known flavivirus neutralization profiles were used as controls in several experiments: Primary (1°) DENV neutralized a single DENV serotype and not ZIKV; Secondary (2°) DENV neutralized at least 2 DENV serotypes and not ZIKV.

Nicaraguan subjects: Patients seeking medical attention for fever, rash, and/or nonsuppurative conjunctivitis in Le6n, Nicaragua, were recruited to a prospective cohort study (ZIKA-TS), in which ZIKV cases were identified by RT-PCR testing on site and confirmed serologically at UNC. ZIKV cases were sampled by blood draw at presentation and at weeks 2, 3, 4, 8, 12, and 24 post symptom onset.

Sri Lankan subjects: During a DENV1 epidemic in Sri Lanka in 2014, suspected symptomatic DENV cases were enrolled for prospective sampling. Cases were confirmed by RT-PCR. All subjects were enrolled within 4 days of symptom onset and a convalescent blood sample was obtained (ranging from 16-29 days post onset of symptoms).

Viruses and Cells

The MR766 and Dakar 41525 strains of ZIKV were obtained from the World Reference Center for Emerging Viruses and Arboviruses (R. Tesh, University of Texas Medical Branch) (69, 70). ZIKV strains H/PF/2013 and PRVABC59 were provided by the US Centers for Disease Control and Prevention (71, 72). ZIKV/2012/PHL (Genbank: KU681082), ZIKV/2014/TH (Genbank: KU681081.3), and ZIKV/2015/Paraiba (Genbank: KX280026.1, PMID 27555311) were obtained. DENV WHO reference strains DENV1 West Pac 74, DENV2

S-16803, DENV3 CH54389 and DENV4 TVP-360 were initially obtained from the Walter Reed Army Institute of Research. DENV2 NGC, DENV2/1974/Tonga (Genbank: AY744147.1), DENV3/1978/Slemen (Genbank: AY648961.1), DENV4/1981/Dominica (Genbank: AF326573.1) were used in the neutralization experiments. To perform culture-based experiments and maintain virus stocks, C6/36 *Aedes albopictus* cells (ATCC #CRL-1660) or Vero (Cercopithecus *aethiops*) cells (ATCC #CCL-81) were used. C6/36 cells were grown at 32° C. with 5% CO2 in MEM supplemented with 10% fetal bovine plasma, L-glutamine, non-essential amino acids, and HEPES buffer. Vero cells were grown at 37° C. with 5% CO2 in DMEM supplemented with 5% fetal bovine plasma and L-glutamine. Virus stocks were titrated on Vero cells by plaque assay or focus-forming assay. All studies were conducted under biosafety level 2 containment.

Human Monoclonal Antibody Generation and Identification

From one primary ZIKV case (DT168), mAbs were generated as previously described using the 6XL method (39). Briefly, total cryopreserved peripheral blood mononuclear cells (PBMC) were thawed and memory B cells isolated by magnetic purification for CD22+B cells and flow cytometric sorting for CD19+CD27$^+$IgM$^-$ class-switched memory B cells (MBCs). MBCs were then transduced with 6XL retorvirus (encoding both Bcl-6 and Bcl-xL) and the cells were activated with CD40L-expressing L cells and interleukin IL-21, which together support proliferation and secretion of soluble antibody (73). To simplify the screening process, transduced cells were initially sorted into polyclonal cultures at 50 cells/well on 96-well plates using flow cytometry on BD FACSAria. Supernatants from polyclonal cultures were tested for the presence of IgG targeting ZIKV by capture ELISA. ZIKV-specific supernatants specimens were further screened for cross-reactivity to DENV in capture ELISA, and for ZIKV E80 binding in direct antigen coating ELISA. Selected ZIKV-specific polyclonal cultures were single-cell sorted into monoclonal cultures using flow cytometry on BD FACSAria, grown on CD40L and IL-21 and then screened as above after four weeks. ZIKV-specific monoclonal cultures were further qualitatively tested for neutralization of ZIKV by incubation of ZIKV with 30 μL of culture supernatant prior to infection of Vero cells and assessment of neutralizing activity by microneutralization assay.

From frozen cell pellets of monoclonal cultures, RNA was isolated, and nested PCR was performed for IgH and IgL genes and then sequenced using specific primers as described (40, 41). Sequences were input into IgBLAST (ncbi.nlm.nih.gov/igblast/) and compared to germline to determine variable heavy and light chain usage, V-(D)-J gene usage, somatic hypermutations, complementary determining region (CDR) 3 sequence, and IgG subtype. Since sequencing of both of the potently neutralizing mAbs revealed IgG1 isotype and Ig-X light chain usage, described methods (40, 41) were used to clone IgH into human IgG1 (Genbank FJ475055) and Igλ expression vectors (FJ517647), respectively. Heavy and light chain vectors were verified by sequencing and co-transfected into HEK-293F cells and mAbs were produced as described (40, 41).

ELISA

Binding of mAb or human plasma IgG to DENV or ZIKV was measured by capture ELISA as previously described (20). Briefly, DENV or ZIKV virions were captured by the anti-E protein mouse mAb 4G2, blocked with 3% nonfat dry milk (LabScientific, Inc), and incubated with mAb or human plasma at indicated dilutions at 37° C. for 1 hour, and binding was detected with an alkaline phosphatase-conjugated goat anti-human IgG secondary antibody (Sigma) and p-nitrophenyl phosphate substrate (Sigma). Absorbance at 405 nm (optical density, OD) was measured on Epoch or Cytation3 plate reader systems (BioTek). ELISA assays to measure recombinant antigen binding (ZIKV E80, ZVEDI, ZVEDIII) or used to confirm depletion were performed as above with the exception that 50 ng purified antigen was coated directly to the plate at 37° C. for 1 hour. ELISA data were reported as OD values that are the average of technical replicates unless otherwise indicated in figure legend. The average OD for technical replicates using naïve human plasma (NHS) at the same dilution factor as test samples serves as the negative control in ELISA assays. In depletion experiments, the OD of depleted sample is expressed as percentage of control from same plasma for some graphs as indicated. For IgG binding to ZVEDI and ZVEDIII, which are expressed as fusion proteins with an MBP tag, the OD values reported are background subtracted for each plasma individually (OD to ZIKV antigen—OD to MBP).

Blockade of Binding (BOB) Assay

Assays for blockade of binding were performed as described previously (74). Briefly, ZIKV was captured using mouse anti-E mAbs 4G2 and plates were blocked as described above for ELISA. Serial dilutions of plasma were added to plates in duplicate and incubated at 37° C. for 1 h. After plates were washed, 100 ng/well of alkaline phosphatase-conjugated G9E or A9E were added, and plates were incubated at 37° C. for 1 h. P-nitrophenyl phosphate substrate was added, and reaction color changes were quantified by spectrophotometry. Percentages of blockade of binding were calculated as follows: [100−(optical density of sample/optical density of control)×100].

Neutralization Assays

Neutralization titers were determined by 96-well microFRNT (38, 75). Serial dilutions of mAb or plasma were mixed with approximately 50-100 focus-forming units of virus in DMEM with 2% FBS. The virus-antibody mixtures were incubated for 1 hour at 37° C. and then transferred to a monolayer of Vero cells for infection for 2 hours at 37° C. OptiMEM overlay media (Gibco, 31985) supplemented with 2% FBS, 1% Anti-Anti and 5 g (1%) Carboxymethylcellulose (Sigma, C-5013) was then added, and cultures were incubated for 40 hours (ZIKV), 48 hours (DENV2 and DENV4) or 52 hours (DENV1, DENV3). Cells were fixed with 70 μL of 4% paraformaldehyde (Thermo, 28908) for 30 minutes. 100 μL of permeabilization buffer was added for 10 minutes followed by 100 μL of blocking buffer (3% normal goat plasma, Sigma G-9023 in permeabilization buffer) and left overnight at 4° C. Fifty microliters of a mixture of primary antibodies 4G2 and 2H2 (76) (ATCC, HB-114; 2H2 not used for ZIKV) were added to the plates and incubated for a 1 hour at 37° C. Cells were washed with a microplate washer (BioTek, ELx405) followed by the addition of 50 μl of 1:1900 horseradish peroxidase-conjugated goat anti-mouse secondary antibody (KPL, 074-1806) for 1 hour at 37° C. Foci were visualized with 60 μL of True Blue (KPL, 5510-0030) and counted with a user-supervised automated counting program on 2×-magnified images of micro-wells. Two naïve human plasma (NHS) controls were included on every plate to define 100% infection.

Antibody Depletions

ZIKV recombinant E protein was purified as previously described (77) and conjugated to HisPur Ni-NTA magnetic beads (Thermo Scientific) per the manufacturer's instructions. Control beads were incubated with an equal amount His-tagged human myelin basic protein (His-MBP). For depletion, plasma were diluted 1:20 and incubated with 30 ug ZIKV E80 or His-MBP control split over 2 rounds for 1 hour at 37° C. each round. Depletion efficiency was confirmed by a ZIKV E80 binding ELISA.

DT168 plasma was depleted of all ZIKV binding antibodies using ZIKV VLPs as previously described (78). ZIKV VLPs (The Native Antigen Company, Kidlington, UK) were produced by transiently expressing ZIKV prM and E proteins in suspension culture adapted HEK-293 cells. Supernatants were cleared by centrifugation and concentrated by tangential flow filtration. The VLPs were purified by discontinuous sucrose gradient, ion exchange chromatography, and size exclusion chromatography, which also provided exchange of buffers to storage buffer. Purified VLPs were stored in 10 mM sodium phosphate, 20 mM sodium citrate, 154 mM sodium chloride, pH 7.4 at −80° C. until further use.

Escape Mutant Selection and Sequence Analysis

ZIKV-PRVABC59 was incubated for 1 hour at 37° C. with various concentrations of mAb—at two-fold the FRNT50 of each mAb—for initial escape selection. The mAb concentration was increased every 3-6 passages up to a maximum concentration of 1000× the FRNT50. Vero cell monolayers in 6-well tissue culture plates were infected with ZIKV-mAb mixture at a MOI of 0.01 for 2 hours at 37° C. Vero cells were washed three times with PBS, and media with the same concentration of selecting mAb was replaced. Cultures were incubated up to 96 hours and checked daily for cytopathic effect. Virus growth in the presence of antibody was monitored by quantitative RT-PCR and by immunofluorescent detection of ZIKV antigens in cell monolayers. WT ZIKV-PRVABC59 was passaged in media alone alongside virus undergoing mAb selection. The E gene of stock, WT passaged, and escape mutants were sequenced and aligned in Vector NTI. Mutations resulting in changes in predicted amino acids were visualized in topographical models using PyMOL.

Epitope Mapping

Alanine scanning mutagenesis was carried out by Integral Molecular on an expression construct for ZIKV prM/E (strain ZikaSPH2015; UniProt accession #Q05320). Residues were mutagenized to create a library of clones, each with an individual point mutant (46). Residues were changed to alanine (with alanine residues changed to serine). The resulting ZIKV prM/E alanine-scan library covered 100% of target residues (672 of 672). Each mutation was confirmed by DNA sequencing, and clones were arrayed into 384-well plates, one mutant per well. Cells expressing each ZIKV E mutant were immunostained with the mAb to be mapped and control mAbs to normalize for protein expression levels. Mean cellular fluorescence was detected using an Intellicyt flow cytometer. If no critical mutations were identified in the initial screen, mAb was converted to Fab and rescreened. This was done for G9E. Mutations within critical clones were identified as critical to the mAb epitope if they did not support reactivity of the mAb, but did support reactivity of conformation-dependent control mAbs. This counter-screen strategy facilitated the exclusion of Env mutants that were globally or locally misfolded or that had an expression defect (45). Validated critical residues represent amino acids whose side chains make the highest energetic contributions to the mAb-epitope interaction (79, 80).

Mouse Protection Experiments

Five week old male and female Ifnar1$^{-/-}$ mice (C57BL/6 background) received 200 μg of A9E, G9E, or IgG1 isotype control by intraperitoneal injection 1 day prior to infection with 1000 FFU of ZIKV (H/PF/2013) by subcutaneous footpad inoculation (44). Weight and lethality were monitored daily for 14 days.

Statistics

FRNT50 values were determined in neutralization assays by using the sigmoidal dose response (variable slope) equation of Prism 6 (GraphPad Software, San Diego, CA, USA). Dilution curves for plasma antibody and monoclonal antibody binding were generated using the same equation. Reported FRNT50 values were required to have an $R^2>0.75$, a hill slope >0.5, and an FRNT50 falling with the range of the dilution series.

Kaplan-Meier curves were used to establish survival differences in mouse challenge experiments. An unpaired Student-s t-test was performed to compare between groups of plasma tested in BOB experiments.

REFERENCES

1. Lazear H M, Diamond M S. Zika Virus: New Clinical Syndromes and its Emergence in the Western Hemisphere. *J. Virol.* [published online ahead of print: Mar. 9, 2016]; doi:10.1128/JVI.00252-16
2. Fauci A S, Morens D M. Zika Virus in the Americas—Yet Another Arbovirus Threat. *N. Engl. J. Med.* [published online ahead of print: Jan. 13, 2016]; doi:10.1056/NEJMp1600297
3. Paules C I, Fauci A S. Yellow Fever—Once Again on the Radar Screen in the Americas. *N. Engl. J. Med.* 2017; 376(15):1397-1399.
4. Collins M H, Metz S W. Progress and Works in Progress: Update on Flavivirus Vaccine Development. *Clin. Ther.* 2017; 39(8):1519-1536.
5. Weiskopf D, Sette A. T-cell immunity to infection with dengue virus in humans. *Front. Immunol.* 2014; 5:93.
6. Collins M, de Silva A. Host response: Cross-fit T cells battle Zika virus. *Nat. Microbiol.* 2017; 2(6):17082.
7. Zent O, Hennig R, Banzhoff A, Broker M. Protection against tick-borne encephalitis with a new vaccine formulation free of protein-derived stabilizers. *J Travel Med* 2005; 12(2):85-93.
8. Hoke C H et al. Protection against Japanese Encephalitis by Inactivated Vaccines. *N. Engl. J. Med.* 1988; 319(10): 608-614.
9. Poland J D, Calisher C H, Monath T P, Downs W G, Murphy K. Persistence of neutralizing antibody 30-35 years after immunization with 17D yellow fever vaccine. *Bull. World Health Organ.* 1981; 59(6):895-900.
10. Gotuzzo E, Yactayo S, Córdova E. Efficacy and duration of immunity after yellow fever vaccination: systematic review on the need for a booster every 10 years. *Am. J. Trop. Med. Hyg.* 2013; 89(3):434-44.
11. Ng T et al. Equine vaccine for West Nile virus. *Dev Biol* 2003; 114:221-227.
12. Wahala W M P B, Silva A M de. The human antibody response to dengue virus infection. *Viruses* 2011; 3(12): 2374-95.
13. Kirkpatrick B D et al. Robust and Balanced Immune Responses to All 4 Dengue Virus Serotypes Following Administration of a Single Dose of a Live Attenuated Tetravalent Dengue Vaccine to Healthy, Flavivirus-Naive Adults. *J Infect Dis* 2015; 212(5):702-710.
14. Guy B, Lang J, Saville M, Jackson N. Vaccination Against Dengue: Challenges and Current Developments. *Annu. Rev. Med.* 2016; 67(1):387-404.

15. Modis Y, Ogata S, Clements D, Harrison S C. A ligand-binding pocket in the dengue virus envelope glycoprotein. *Proc. Natl. Acad. Sci. U.S.A.,* 2003; 100(12): 6986-91.
16. Sirohi D et al. The 3.8 Å resolution cryo-EM structure of Zika virus. *Science* 2016; 352(6284):467-70.
17. Kostyuchenko V A et al. Structure of the thermally stable Zika virus. *Nature* 2016; 533(7603):425-8.
18. Teoh E P et al. The structural basis for serotype-specific neutralization of dengue virus by a human antibody. *Sci. Transl. Med.* 2012; 4(139):139ra83.
19. Gallichotte E N et al. A new quaternary structure epitope on dengue virus serotype 2 is the target of durable type-specific neutralizing antibodies. *MBio* 2015; 6(5): e01461-15.
20. de Alwis R et al. Identification of human neutralizing antibodies that bind to complex epitopes on dengue virions. *Proc. Natl. Acad. Sci. U.S.A.* 2012; 109(19):7439-44.
21. Kaufmann B et al. Neutralization of West Nile virus by cross-linking of its surface proteins with Fab fragments of the human monoclonal antibody CR4354. *Proc. Natl. Acad. Sci. U.S.A.* 2010; 107(44):18950-5.
22. Hadjilaou A, Green A M, Coloma J, Harris E. Single-Cell Analysis of B Cell/Antibody Cross-Reactivity Using a Novel Multicolor FluoroSpot Assay. *J. Immunol.* 2015; 195(7):3490-6.
23. Mathew A et al. B-cell responses during primary and secondary dengue virus infections in humans. *J. Infect. Dis.* 2011; 204(10):1514-22.
24. Bhatt S et al. The global distribution and burden of dengue. *Nature* 2013; 496(7446):504-507.
25. Musso D, Gubler D J. Zika Virus. *Clin. Microbiol. Rev.* 2016; 29(3):487-524.
26. Speer S D, Pierson T C. VIROLOGY. Diagnostics for Zika virus on the horizon. *Science* 2016; 353(6301):750-1.
27. Premkumar L et al. Development of envelope protein antigens to serologically differentiate Zika from dengue virus infection. *J. Clin. Microbiol.* 2017; JCM.01504-17.
28. Rabe I B et al. Interim Guidance for Interpretation of Zika Virus Antibody Test Results. *MMWR. Morb. Mortal. Wkly. Rep.* 2016; 65(21):543-6.
29. Lanciotti R S et al. Genetic and serologic properties of Zika virus associated with an epidemic, *Yap State, Micronesia,* 2007. *Emerg. Infect. Dis.* 2008; 14(8):1232-9.
30. Halstead S B. Biologic Evidence Required for Zika Disease Enhancement by Dengue *Antibodies. Emerg. Infect. Dis.* 2017; 23(4). doi:10.3201/eid2304.161879
31. McCracken M K et al. Impact of prior flavivirus immunity on Zika virus infection in rhesus macaques. *PLOS Pathog.* 2017; 13(8):e1006487.
32. George J et al. Prior Exposure to Zika Virus Significantly Enhances Peak Dengue-2 Viremia in Rhesus Macaques. *Sci. Rep.* 2017; 7(1):10498.
33. Priyamvada L et al. Human antibody responses after dengue virus infection are highly cross-reactive to Zika virus doi:10.1073/pnas.1607931113
34. Robbiani D F et al. Recurrent Potent Human Neutralizing Antibodies to Zika Virus in Brazil and Mexico. *Cell* 2017; 169(4):597-609.e11.
35. Rogers T F et al. Zika virus activates de novo and cross-reactive memory B cell responses in dengue-experienced donors. *Sci. Immunol.* 2017; 2(14):eaan6809.
36. Stettler K et al. Specificity, cross-reactivity and function of antibodies elicited by Zika virus infection. *Science* [published online ahead of print: Jul. 14, 2016]; doi: 10.1126/science.aaf8505
37. Montoya M et al. Longitudinal Analysis of Antibody Cross-Neutralization Following Zika and Dengue Virus Infection in Asia and the Americas. *J. Infect. Dis.* [published online ahead of print: Apr. 2, 2018]; doi:10.1093/infdis/jiy164
38. Collins M H et al. Lack of Durable Cross-Neutralizing Antibodies Against Zika Virus from Dengue Virus Infection. *Emerg. Infect. Dis.* 2017; 23(5):773-781.
39. Kwakkenbos M J et al. Generation of stable monoclonal antibody-producing B cell receptor-positive human memory B cells by genetic programming. *Nat. Med.* 2010; 16(1):123-8.
40. Smith K et al. Rapid generation of fully human monoclonal antibodies specific to a vaccinating antigen. *Nat. Protoc.* 2009; 4(3):372-84.
41. Ho I Y et al. Refined protocol for generating monoclonal antibodies from single human and murine B cells. *J. Immunol. Methods* 2016; 438:67-70.
42. Dejnirattisai W et al. A new class of highly potent, broadly neutralizing antibodies isolated from viremic patients infected with dengue virus. *Nat. Immunol.* 2015; 16(2):170-7.
43. Wang J et al. A Human Bi-specific Antibody against Zika Virus with High Therapeutic Potential. *Cell* 2017; 171(1): 229-241.e15.
44. Lazear H M et al. A Mouse Model of Zika Virus Pathogenesis. *Cell Host Microbe* [published online ahead of print: Apr. 5, 2016]; doi:10.1016/j.chom.2016.03.010
45. Davidson E, Doranz B J. A high-throughput shotgun mutagenesis approach to mapping B-cell antibody epitopes. *Immunology* 2014; 143(1):13-20.
46. Sapparapu G et al. Neutralizing human antibodies prevent Zika virus replication and fetal disease in mice. *Nature* 2016; 540(7633):443-447.
47. Fibriansah G et al. A highly potent human antibody neutralizes dengue virus serotype 3 by binding across three surface proteins. *Nat. Commun.* 2015; 6:6341.
48. Kiermayr S, Stiasny K, Heinz F X. Impact of quaternary organization on the antigenic structure of the tick-borne encephalitis virus envelope glycoprotein E. *J. Virol.* 2009; 83(17):8482-91.
49. Wang Q et al. Molecular determinants of human neutralizing antibodies isolated from a patient infected with Zika virus. *Sci. Transl. Med.* 2016; 8(369):369ra179-369ra179.
50. Yu L et al. Delineating antibody recognition against Zika virus during natural infection. *JCI Insight* 2017; 2(12). doi:10.1172/jci.insight.93042
51. Williams K L, Wahala W M P B, Orozco S, de Silva A M, Harris E. Antibodies targeting dengue virus envelope domain III are not required for serotype-specific protection or prevention of enhancement in vivo. *Virology* 2012; 429(1):12-20.
52. Mathew A et al. B-Cell Responses During Primary and Secondary Dengue Virus Infections in Humans. *J. Infect. Dis.* 2011; 204(10):1514-1522.
53. Lai L et al. Innate, T-, and B-Cell Responses in Acute Human Zika Patients. *Clin. Infect. Dis.* [*published online ahead of print:* 2017]; (Epub ahead of publication). doi: 10.1093/cid/cix732
54. Goo L et al. The Zika virus envelope protein glycan loop regulates virion antigenicity. *Virology* 2018; 515:191-202.

55. Sessions O M et al. Analysis of Dengue Virus Genetic Diversity during Human and Mosquito Infection Reveals Genetic Constraints. *PLoS Negl. Trop. Dis.* 2015; 9(9): e0004044.
56. Balmaseda A et al. Antibody-based assay discriminates Zika virus infection from other flaviviruses. *Proc. Natl. Acad. Sci. U.S.A.* 2017; 201704984.
57. Dowd K A et al. Broadly Neutralizing Activity of Zika Virus-Immune Sera Identifies a Single Viral Serotype. *Cell Rep.* [published online ahead of print: July 2016]; doi:10.1016/j.celrep.2016.07.049
58. Aliota M T et al. Heterologous Protection against Asian Zika Virus Challenge in Rhesus Macaques. *PLoS Negl. Trop. Dis.* 2016; 10(12):e0005168.
59. Smith S A et al. Persistence of circulating memory B cell clones with potential for dengue virus disease enhancement for decades following infection. *J. Virol.* 2012; 86(5):2665-75.
60. Beltramello M et al. The human immune response to Dengue virus is dominated by highly cross-reactive antibodies endowed with neutralizing and enhancing activity. *Cell Host Microbe* 2010; 8(3):271-83.
61. Katzelnick L C et al. Antibody-dependent enhancement of severe dengue disease in humans. *Science* (80-.). 2017; 358(6365):929-932.
62. Dejnirattisai W et al. Dengue virus sero-cross-reactivity drives antibody-dependent enhancement of infection with zika virus. *Nat. Immunol.* [published online ahead of print: Jun. 23, 2016]; doi:10.1038/ni.3515
63. Castanha P M et al. Dengue virus (DENV)-specific antibodies enhance Brazilian Zika virus (ZIKV) infection. *J. Infect. Dis.* 2016; 215(5):jiw638.
64. Paul L M et al. Dengue virus antibodies enhance Zika virus infection. *Clin.* Transl. *Immunol.* 2016; 5(12):e117.
65. Bardina S V. et al. Enhancement of Zika virus pathogenesis by preexisting antiflavivirus immunity. *Science* (80-.). 2017;
66. Pantoja P et al. Zika virus pathogenesis in rhesus macaques is unaffected by pre-existing immunity to dengue virus. *Nat. Commun.* 2017; 8:15674.
67. Halai U et al. Maternal Zika Virus Disease Severity, Virus Load, Prior Dengue Antibodies and their Relationship to Birth Outcomes. *Clin. Infect. Dis.* [published online ahead of print: May 23, 2017]; doi:10.1093/cid/cix472
68. Kawiecki A B, Christofferson R C. Zika Virus-Induced Antibody Response Enhances Dengue Virus Serotype 2 Replication In Vitro. *J. Infect. Dis.* 2016; 214(9):1357-1360.
69. Dick Gwa, Kitchen S F, Haddow A J. Zika virus. I. Isolations and serological specificity. *Trans. R. Soc. Trop. Med. Hyg.* 1952; 46(5):509-20.
70. Haddow A D et al. Genetic characterization of Zika virus strains: geographic expansion of the Asian lineage. *PLoS Negl. Trop. Dis.* 2012; 6(2):el477.
71. Baronti C et al. Complete coding sequence of zika virus from a French polynesia outbreak in 2013. *Genome Announc.* 2014; 2(3). doi:10.1128/genomeA.00500-14
72. Lanciotti R S, Lambert A J, Holodniy M, Saavedra S, Signor LDCC. Phylogeny of Zika Virus in Western Hemisphere, 2015. *Emerg. Infect. Dis.* 2016; 22(5):933-5.
73. Diehl S A et al. STAT3-mediated up-regulation of BLIMP1 Is coordinated with BCL6 down-regulation to control human plasma cell differentiation. *J. Immunol.* 2008; 180(7):4805-15.
74. Nivarthi U K et al. Mapping the Human Memory B Cell and Serum Neutralizing Antibody Responses to Dengue Virus Serotype 4 Infection and Vaccination. *J. Virol.* 2017; 91(5):e02041-16.
75. Swanstrom J A et al. Dengue Virus Envelope Dimer Epitope Monoclonal Antibodies Isolated from Dengue Patients Are Protective against Zika Virus. *MBio* 2016; 7(4). doi:10.1128/mBio.01123-16
76. Henchal E A, Gentry M K, McCown J M, Brandt W E. Dengue virus-specific and flavivirus group determinants identified with monoclonal antibodies by indirect immunofluorescence. *Am. J. Trop. Med. Hyg.* 1982; 31(4):830-6.
77. Metz S W et al. In Vitro Assembly and Stabilization of Dengue and Zika Virus Envelope Protein Homo-Dimers. *Sci. Rep.* 2017; 7(1):4524.
78. Metz S W et al. Dengue virus-like particles mimic the antigenic properties of the infectious dengue virus envelope. *Virol. J.* 2018; 15(1):60.
79. Bogan A A, Thorn K S. Anatomy of hot spots in protein interfaces. *J. Mol. Biol.* 1998; 280(1):1-9.
80. Lo Conte L, Chothia C, Janin J. The atomic structure of protein-protein recognition sites. *J. Mol. Biol.* 1999; 285 (5):2177-98.

OTHER EMBODIMENTS

In the claims articles such as “a,” “an,” and “the” may mean one or more than one unless indicated to the contrary or otherwise evident from the context. Claims or descriptions that include “or” between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms “comprising” and “containing” are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

We claim:

1. A method of treating a subject with Zika virus, comprising administering an effective amount of a composition to the subject, wherein the composition comprises:

(a) an antibody or an antigen-binding antibody fragment that binds Domain I of Zika virus (ZIKV) Envelope protein (EDI), binds ZIKV strain MR766, or binds ZIKV Envelope protein III (EDIII), wherein the antibody or antigen-binding antibody fragment comprises a heavy chain variable region and a light chain variable region, and wherein:

(i) the heavy chain variable region comprises an amino acid sequence that is identical to SEQ ID NO: 1 and the light chain variable region comprises an amino acid sequence that is identical to SEQ ID NO: 2; or (ii) the heavy chain variable region comprises an amino acid sequence that is identical to SEQ ID NO: 3 and the light chain variable region comprises an amino acid sequence that is identical to SEQ ID NO: 4; and (b) a pharmaceutically acceptable carrier.

2. The method of claim 1, wherein the antigen-binding antibody fragment is an scFv.

3. The method of claim 1, wherein the antibody is a full-length antibody.

4. The method of claim 3, wherein the full-length antibody is an IgG molecule.

5. The method of claim 1, wherein the antibody or the antigen-binding antibody fragment does not neutralize Dengue viruses 1-4.

6. The method of claim 1, wherein the antibody or the antigen-binding antibody fragment is encoded by a nucleic acid.

7. The method of claim 1, wherein the antibody is a human antibody.

8. The method of claim 1, wherein the composition is administered intramuscularly, subcutaneously, or intravenously.

9. The method of claim 1, wherein the subject is a human subject.

* * * * *

SEQUENCE LISTING

```
<160> NUMBER OF SEQ ID NOS: 26

<210> SEQ ID NO 1
<211> LENGTH: 124
<212> TYPE: PRT
<213> ORGANISM: Artificial Sequence
<220> FEATURE:
<223> OTHER INFORMATION: Synthetic polypeptide

<400> SEQUENCE: 1

Glu Val Gln Leu Leu Glu Ser Gly Gly Gly Leu Val Gln Ala Gly Gly
1               5                   10                  15

Ser Leu Arg Leu Ser Cys Ala Ala Ser Gly Phe Thr Phe Asp Thr Tyr
            20                  25                  30

Ala Met Ser Trp Val Arg Gln Pro Pro Gly Lys Gly Leu Glu Trp Val
        35                  40                  45

Ser Ala Ile Ser Thr Gly Gly Gly Ser Lys Tyr Tyr Ala Asp Ser Val
    50                  55                  60

Lys Gly Arg Leu Thr Ile Ser Arg Asp Asn Ser Gln Asn Thr Leu Tyr
65                  70                  75                  80

Leu Gln Met Ser Ser Leu Arg Ala Asp Asp Thr Ala Val Tyr Tyr Cys
                85                  90                  95

Ala Arg Ser Asp Phe Trp Arg Ser Gly Arg Tyr Tyr Tyr Tyr Met Asp
            100                 105                 110

Val Trp Gly Arg Gly Thr Thr Val Thr Val Ser Ser
        115                 120


<210> SEQ ID NO 2
<211> LENGTH: 110
<212> TYPE: PRT
<213> ORGANISM: Artificial Sequence
<220> FEATURE:
<223> OTHER INFORMATION: Synthetic polypeptide

<400> SEQUENCE: 2

Gln Ser Ala Leu Thr Gln Pro Ala Ser Val Ser Ala Ser Pro Gly Gln
1               5                   10                  15

Ser Ile Thr Ile Ser Cys Thr Gly Thr His Phe Asp Ile Val Asp Tyr
            20                  25                  30

Asp Tyr Leu Ser Trp Tyr Gln Gln His Pro Gly Asn Ala Pro Lys Leu
        35                  40                  45

Leu Ile Tyr Gly Val Ser Asn Arg Pro Ser Gly Val Ser Ser Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Gly Asp Tyr Tyr Cys Ser Ser Tyr Ser Ile Ser
```

```
                85                  90                  95

Ser Thr Leu Leu Val Phe Gly Gly Gly Thr Lys Leu Ser Val
            100                 105                 110


<210> SEQ ID NO 3
<211> LENGTH: 128
<212> TYPE: PRT
<213> ORGANISM: Artificial Sequence
<220> FEATURE:
<223> OTHER INFORMATION: Synthetic polypeptide

<400> SEQUENCE: 3

Glu Val Gln Leu Val Glu Ser Gly Gly Gly Val Val Gln Pro Gly Arg
1               5                   10                  15

Ser Leu Arg Leu Ser Cys Val Ala Ser Gly Phe Ala Phe Ser Asn Tyr
            20                  25                  30

His Met His Trp Val Arg Gln Ala Pro Gly Lys Gly Leu Glu Trp Val
        35                  40                  45

Ala Ile Ile Trp Asp Asp Gly Ser Asp Gln Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Arg Leu Arg Ala Glu Asp Thr Ala Leu Tyr Tyr Cys
                85                  90                  95

Val Gly Gly Ser Ser Ala Tyr Asn Gly Asp Asn Gly Trp Arg Glu Ala
            100                 105                 110

Ala Ser Leu Asp Asp Trp Gly Gln Gly Thr Leu Val Thr Val Ser Ser
        115                 120                 125


<210> SEQ ID NO 4
<211> LENGTH: 110
<212> TYPE: PRT
<213> ORGANISM: Artificial Sequence
<220> FEATURE:
<223> OTHER INFORMATION: Synthetic polypeptide

<400> SEQUENCE: 4

Gln Ser Ala Leu Thr Gln Pro Ala Ser Val Ser Gly Ser Pro Gly Gln
1               5                   10                  15

Ser Ile Thr Ile Phe Cys Ser Gly Ser Ser Asn Asp Val Gly Gly Tyr
            20                  25                  30

Asn Tyr Val Ser Trp Tyr Gln Gln Tyr Pro Gly Lys Val Pro Lys Leu
        35                  40                  45

Leu Ile Tyr Asp Val Asn Ser Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Arg
                85                  90                  95

Arg Thr Trp Val Phe Gly Gly Gly Thr Ile Val Thr Val Leu
            100                 105                 110


<210> SEQ ID NO 5
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 5
```

Ala Arg Ser Asp Phe Trp Arg Ser Gly Arg Tyr Tyr Tyr Tyr Met Asp
1               5                   10                  15

Val

<210> SEQ ID NO 6
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 6

Ser Ser Tyr Ser Ile Ser Ser Thr Leu Leu Val
1               5                   10

<210> SEQ ID NO 7
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 7

Val Gly Gly Ser Ser Ala Tyr Asn Gly Asp Asn Gly Trp Arg Glu Ala
1               5                   10                  15

Ala Ser Leu Asp Asp
            20

<210> SEQ ID NO 8
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 8

Ser Ser Tyr Thr Ser Arg Arg Thr Trp Val
1               5                   10

<210> SEQ ID NO 9
<211> LENGTH: 372
<212> TYPE: DNA
<213> ORGANISM: Artificial Sequence
<220> FEATURE:
<223> OTHER INFORMATION: Synthetic polynucleotide

<400> SEQUENCE: 9
gaggtgcagc tgttggagtc tgggggaggc ttggttcagg cggggggtc cctgagactc     60 tcctgtgcag cctctggatt cacctttgac acctatgcca tgagttgggt ccgccagcct    120
ccagggaagg ggctggagtg ggtctccgct attagcactg gtggtggcag caaatactac    180
gcagactccg taaagggccg gctcaccatc tccagagaca attcccagaa cacgctgtat    240
ctgcagatga gcagcctgag agccgacgac acggccgtat attactgtgc gaggtccgat    300
ttttggagga gtggtcgtta ttactactac atggacgtct ggggcagagg gaccacggtc    360
accgtctcct ca                                                        372

<210> SEQ ID NO 10
<211> LENGTH: 330
<212> TYPE: DNA
<213> ORGANISM: Artificial Sequence
<220> FEATURE:
<223> OTHER INFORMATION: Synthetic polynucleotide

<400> SEQUENCE: 10

```
cagtctgccc tgactcagcc tgcctccgtg tctgcgtccc ctggacaatc gatcaccatc     60
tcctgcactg gaacccactt tgacattgtt gattatgact atctctcctg gtaccaacaa    120
cacccaggca acgcccccaa actcctgatt tatggtgtca gtaatcggcc ctcaggggtc    180
tcaagtcgct tctctggttc caagtctggc aacacggcct ccctgaccat ctctgggctc    240
caggctgagg acgagggtga ttattattgc agctcctatt caatctccag cactctccta    300
gttttcggcg gagggacgaa gctgtccgtc                                      330
```

<210> SEQ ID NO 11
<211> LENGTH: 384
<212> TYPE: DNA
<213> ORGANISM: Artificial Sequence
<220> FEATURE:
<223> OTHER INFORMATION: Synthetic polynucleotide

<400> SEQUENCE: 11

```
gaggtgcagc tggtggagtc tgggggaggc gtggtccagc ctgggaggtc ccttagactc     60
tcctgtgtag catctggatt cgccttcagt aactatcaca tgcactgggt ccgccaggct    120
ccaggcaagg ggctggagtg ggtggcaatt atctgggatg atggaagtga tcaatattat    180
gcagactccg tgaagggccg attcaccatc tccagagaca attccaagaa cacattgttt    240
ctgcaaatga acagactgag agccgaggac acggctctct attactgtgt gggaggatcc    300
tctgcctata acggtgacaa cggttggcgg gaagctgcga gcctggacga ctggggccag    360
ggaaccctgg tcaccgtctc ctca                                            384
```

<210> SEQ ID NO 12
<211> LENGTH: 330
<212> TYPE: DNA
<213> ORGANISM: Artificial Sequence
<220> FEATURE:
<223> OTHER INFORMATION: Synthetic polynucleotide

<400> SEQUENCE: 12

```
cagtctgccc tgactcagcc tgcctccgtg tctgggtctc ctggacaatc gatcaccatt     60
ttctgcagtg gaagcagcaa tgacgttgga ggttataatt atgtctcctg gtaccagcaa    120
tacccaggca aagtccccaa actcctgatt tatgatgtca atagtcggcc ctcaggggtt    180
tctaatcgct tctctggctc caagtctggc aacacggcct ccctgaccat ctctgggctc    240
caggctgagg acgaggctga ttattattgc agctcatata caagtagaag aacttgggtg    300
ttcggcggag ggaccatagt gaccgtccta                                      330
```

<210> SEQ ID NO 13
<211> LENGTH: 3423
<212> TYPE: PRT
<213> ORGANISM: Unknown
<220> FEATURE:
<223> OTHER INFORMATION: Zika virus

<400> SEQUENCE: 13

```
Met Lys Asn Pro Lys Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45
```

-continued

Ala Ile Leu Ala Phe Leu Arg Phe Thr Ala Ile Lys Pro Ser Leu Gly
50 55 60

Leu Ile Asn Arg Trp Gly Ser Val Gly Lys Lys Glu Ala Met Glu Ile
65 70 75 80

Ile Lys Lys Phe Lys Lys Asp Leu Ala Ala Met Leu Arg Ile Ile Asn
85 90 95

Ala Arg Lys Glu Lys Lys Arg Arg Gly Ala Asp Thr Ser Val Gly Ile
100 105 110

Val Gly Leu Leu Leu Thr Thr Ala Met Ala Ala Glu Val Thr Arg Arg
115 120 125

Gly Ser Ala Tyr Tyr Met Tyr Leu Asp Arg Asn Asp Ala Gly Glu Ala
130 135 140

Ile Ser Phe Pro Thr Thr Leu Gly Met Asn Lys Cys Tyr Ile Gln Ile
145 150 155 160

Met Asp Leu Gly His Met Cys Asp Ala Thr Met Ser Tyr Glu Cys Pro
165 170 175

Met Leu Asp Glu Gly Val Glu Pro Asp Asp Val Asp Cys Trp Cys Asn
180 185 190

Thr Thr Ser Thr Trp Val Val Tyr Gly Thr Cys His His Lys Lys Gly
195 200 205

Glu Ala Arg Arg Ser Arg Arg Ala Val Thr Leu Pro Ser His Ser Thr
210 215 220

Arg Lys Leu Gln Thr Arg Ser Gln Thr Trp Leu Glu Ser Arg Glu Tyr
225 230 235 240

Thr Lys His Leu Ile Arg Val Glu Asn Trp Ile Phe Arg Asn Pro Gly
245 250 255

Phe Ala Leu Ala Ala Ala Ala Ile Ala Trp Leu Leu Gly Ser Ser Thr
260 265 270

Ser Gln Lys Val Ile Tyr Leu Val Met Ile Leu Leu Ile Ala Pro Ala
275 280 285

Tyr Ser Ile Arg Cys Ile Gly Val Ser Asn Arg Asp Phe Val Glu Gly
290 295 300

Met Ser Gly Gly Thr Trp Val Asp Val Val Leu Glu His Gly Gly Cys
305 310 315 320

Val Thr Val Met Ala Gln Asp Lys Pro Thr Val Asp Ile Glu Leu Val
325 330 335

Thr Thr Thr Val Ser Asn Met Ala Glu Val Arg Ser Tyr Cys Tyr Glu
340 345 350

Ala Ser Ile Ser Asp Met Ala Ser Asp Ser Arg Cys Pro Thr Gln Gly
355 360 365

Glu Ala Tyr Leu Asp Lys Gln Ser Asp Thr Gln Tyr Val Cys Lys Arg
370 375 380

Thr Leu Val Asp Arg Gly Trp Gly Asn Gly Cys Gly Leu Phe Gly Lys
385 390 395 400

Gly Ser Leu Val Thr Cys Ala Lys Phe Ala Cys Ser Lys Lys Met Thr
405 410 415

Gly Lys Ser Ile Gln Pro Glu Asn Leu Glu Tyr Arg Ile Met Leu Ser
420 425 430

Val His Gly Ser Gln His Ser Gly Met Ile Val Asn Asp Thr Gly His
435 440 445

Glu Thr Asp Glu Asn Arg Ala Lys Val Glu Ile Thr Pro Asn Ser Pro
450 455 460

```
Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
        515                 520                 525

Lys Glu Ala Leu Val Glu Phe Lys Asp Ala His Ala Lys Arg Gln Thr
    530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
        595                 600                 605

Ala Glu Thr Leu His Gly Thr Val Thr Val Glu Val Gln Tyr Ala Gly
    610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
        675                 680                 685

His Trp His Arg Ser Gly Ser Thr Ile Gly Lys Ala Phe Glu Ala Thr
    690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
        755                 760                 765

Thr Lys Asn Gly Ser Ile Ser Leu Met Cys Leu Ala Leu Gly Gly Val
    770                 775                 780

Leu Ile Phe Leu Ser Thr Ala Val Ser Ala Asp Val Gly Cys Ser Val
785                 790                 795                 800

Asp Phe Ser Lys Lys Glu Thr Arg Cys Gly Thr Gly Val Phe Val Tyr
                805                 810                 815

Asn Asp Val Glu Ala Trp Arg Asp Arg Tyr Lys Tyr His Pro Asp Ser
            820                 825                 830

Pro Arg Arg Leu Ala Ala Ala Val Lys Gln Ala Trp Glu Asp Gly Ile
        835                 840                 845

Cys Gly Ile Ser Ser Val Ser Arg Met Glu Asn Ile Met Trp Arg Ser
    850                 855                 860

Val Glu Gly Glu Leu Asn Ala Ile Leu Glu Glu Asn Gly Val Gln Leu
865                 870                 875                 880

Thr Val Val Val Gly Ser Val Lys Asn Pro Met Trp Arg Gly Pro Gln
```

```
            885                 890                 895

Arg Leu Pro Val Pro Val Asn Glu Leu Pro His Gly Trp Lys Ala Trp
        900                 905                 910

Gly Lys Ser Tyr Phe Val Arg Ala Ala Lys Thr Asn Asn Ser Phe Val
    915                 920                 925

Val Asp Gly Asp Thr Leu Lys Glu Cys Pro Leu Lys His Arg Ala Trp
    930                 935                 940

Asn Ser Phe Leu Val Glu Asp His Gly Phe Gly Val Phe His Thr Ser
945                 950                 955                 960

Val Trp Leu Lys Val Arg Glu Asp Tyr Ser Leu Glu Cys Asp Pro Ala
            965                 970                 975

Val Ile Gly Thr Ala Val Lys Gly Lys Glu Ala Val His Ser Asp Leu
        980                 985                 990

Gly Tyr Trp Ile Glu Ser Glu Lys  Asn Asp Thr Trp Arg  Leu Lys Arg
    995                 1000                 1005

Ala His  Leu Ile Glu Met Lys  Thr Cys Glu Trp Pro  Lys Ser His
    1010                 1015                 1020

Thr Leu  Trp Thr Asp Gly Ile  Glu Glu Ser Asp Leu  Ile Ile Pro
    1025                 1030                 1035

Lys Ser  Leu Ala Gly Pro Leu  Ser His His Asn Thr  Arg Glu Gly
    1040                 1045                 1050

Tyr Arg  Thr Gln Met Lys Gly  Pro Trp His Ser Glu  Glu Leu Glu
    1055                 1060                 1065

Ile Arg  Phe Glu Glu Cys Pro  Gly Thr Lys Val His  Val Glu Glu
    1070                 1075                 1080

Thr Cys  Gly Thr Arg Gly Pro  Ser Leu Arg Ser Thr  Thr Ala Ser
    1085                 1090                 1095

Gly Arg  Val Ile Glu Glu Trp  Cys Cys Arg Glu Cys  Thr Met Pro
    1100                 1105                 1110

Pro Leu  Ser Phe Arg Ala Lys  Asp Gly Cys Trp Tyr  Gly Met Glu
    1115                 1120                 1125

Ile Arg  Pro Arg Lys Glu Pro  Glu Ser Asn Leu Val  Arg Ser Met
    1130                 1135                 1140

Val Thr  Ala Gly Ser Thr Asp  His Met Asp His Phe  Ser Leu Gly
    1145                 1150                 1155

Val Leu  Val Ile Leu Leu Met  Val Gln Glu Gly Leu  Lys Lys Arg
    1160                 1165                 1170

Met Thr  Thr Lys Ile Ile Ile  Ser Thr Ser Met Ala  Val Leu Val
    1175                 1180                 1185

Ala Met  Ile Leu Gly Gly Phe  Ser Met Ser Asp Leu  Ala Lys Leu
    1190                 1195                 1200

Ala Ile  Leu Met Gly Ala Thr  Phe Ala Glu Met Asn  Thr Gly Gly
    1205                 1210                 1215

Asp Val  Ala His Leu Ala Leu  Ile Ala Ala Phe Lys  Val Arg Pro
    1220                 1225                 1230

Ala Leu  Leu Val Ser Phe Ile  Phe Arg Ala Asn Trp  Thr Pro Arg
    1235                 1240                 1245

Glu Ser  Met Leu Leu Ala Leu  Ala Ser Cys Leu Leu  Gln Thr Ala
    1250                 1255                 1260

Ile Ser  Ala Leu Glu Gly Asp  Leu Met Val Leu Ile  Asn Gly Phe
    1265                 1270                 1275

Ala Leu  Ala Trp Leu Ala Ile  Arg Ala Met Val Val  Pro Arg Thr
    1280                 1285                 1290
```

```
Asp Asn  Ile Thr Leu Ala Ile  Leu Ala Ala Leu Thr  Pro Leu Ala
    1295                 1300                 1305

Arg Gly  Thr Leu Leu Val Ala  Trp Arg Ala Gly Leu  Ala Thr Cys
    1310                 1315                 1320

Gly Gly  Phe Met Leu Leu Ser  Leu Lys Gly Lys Gly  Ser Val Lys
    1325                 1330                 1335

Lys Asn  Leu Pro Phe Val Met  Ala Leu Gly Leu Thr  Ala Val Arg
    1340                 1345                 1350

Leu Val  Asp Pro Ile Asn Val  Val Gly Leu Leu Leu  Leu Thr Arg
    1355                 1360                 1365

Ser Gly  Lys Arg Ser Trp Pro  Pro Ser Glu Val Leu  Thr Ala Val
    1370                 1375                 1380

Gly Leu  Ile Cys Ala Leu Ala  Gly Gly Phe Ala Lys  Ala Asp Ile
    1385                 1390                 1395

Glu Met  Ala Gly Pro Met Ala  Ala Val Gly Leu Leu  Ile Val Ser
    1400                 1405                 1410

Tyr Val  Val Ser Gly Lys Ser  Val Asp Met Tyr Ile  Glu Arg Ala
    1415                 1420                 1425

Gly Asp  Ile Thr Trp Glu Lys  Asp Ala Glu Val Thr  Gly Asn Ser
    1430                 1435                 1440

Pro Arg  Leu Asp Val Ala Leu  Asp Glu Ser Gly Asp  Phe Ser Leu
    1445                 1450                 1455

Val Glu  Asp Asp Gly Pro Pro  Met Arg Glu Ile Ile  Leu Lys Val
    1460                 1465                 1470

Val Leu  Met Thr Ile Cys Gly  Met Asn Pro Ile Ala  Ile Pro Phe
    1475                 1480                 1485

Ala Ala  Gly Ala Trp Tyr Val  Tyr Val Lys Thr Gly  Lys Arg Ser
    1490                 1495                 1500

Gly Ala  Leu Trp Asp Val Pro  Ala Pro Lys Glu Val  Lys Lys Gly
    1505                 1510                 1515

Glu Thr  Thr Asp Gly Val Tyr  Arg Val Met Thr Arg  Arg Leu Leu
    1520                 1525                 1530

Gly Ser  Thr Gln Val Gly Val  Gly Val Met Gln Glu  Gly Val Phe
    1535                 1540                 1545

His Thr  Met Trp His Val Thr  Lys Gly Ser Ala Leu  Arg Ser Gly
    1550                 1555                 1560

Glu Gly  Arg Leu Asp Pro Tyr  Trp Gly Asp Val Lys  Gln Asp Leu
    1565                 1570                 1575

Val Ser  Tyr Cys Gly Pro Trp  Lys Leu Asp Ala Ala  Trp Asp Gly
    1580                 1585                 1590

His Ser  Glu Val Gln Leu Leu  Ala Val Pro Pro Gly  Glu Arg Ala
    1595                 1600                 1605

Arg Asn  Ile Gln Thr Leu Pro  Gly Ile Phe Lys Thr  Lys Asp Gly
    1610                 1615                 1620

Asp Ile  Gly Ala Val Ala Leu  Asp Tyr Pro Ala Gly  Thr Ser Gly
    1625                 1630                 1635

Ser Pro  Ile Leu Asp Lys Cys  Gly Arg Val Ile Gly  Leu Tyr Gly
    1640                 1645                 1650

Asn Gly  Val Val Ile Lys Asn  Gly Ser Tyr Val Ser  Ala Ile Thr
    1655                 1660                 1665

Gln Gly  Arg Arg Glu Glu Glu  Thr Pro Val Glu Cys  Phe Glu Pro
    1670                 1675                 1680
```

```
Ser Met  Leu Lys Lys Lys Gln  Leu Thr Val Leu Asp  Leu His Pro
    1685                 1690                 1695

Gly Ala  Gly Lys Thr Arg Arg  Val Leu Pro Glu Ile  Val Arg Glu
    1700                 1705                 1710

Ala Ile  Lys Thr Arg Leu Arg  Thr Val Ile Leu Ala  Pro Thr Arg
    1715                 1720                 1725

Val Val  Ala Ala Glu Met Glu  Glu Ala Leu Arg Gly  Leu Pro Val
    1730                 1735                 1740

Arg Tyr  Met Thr Thr Ala Val  Asn Val Thr His Ser  Gly Thr Glu
    1745                 1750                 1755

Ile Val  Asp Leu Met Cys His  Ala Thr Phe Thr Ser  Arg Leu Leu
    1760                 1765                 1770

Gln Pro  Ile Arg Val Pro Asn  Tyr Asn Leu Tyr Ile  Met Asp Glu
    1775                 1780                 1785

Ala His  Phe Thr Asp Pro Ser  Ser Ile Ala Ala Arg  Gly Tyr Ile
    1790                 1795                 1800

Ser Thr  Arg Val Glu Met Gly  Glu Ala Ala Ala Ile  Phe Met Thr
    1805                 1810                 1815

Ala Thr  Pro Pro Gly Thr Arg  Asp Ala Phe Pro Asp  Ser Asn Ser
    1820                 1825                 1830

Pro Ile  Met Asp Thr Glu Val  Glu Val Pro Glu Arg  Ala Trp Ser
    1835                 1840                 1845

Ser Gly  Phe Asp Trp Val Thr  Asp His Ser Gly Lys  Thr Val Trp
    1850                 1855                 1860

Phe Val  Pro Ser Val Arg Asn  Gly Asn Glu Ile Ala  Ala Cys Leu
    1865                 1870                 1875

Thr Lys  Ala Gly Lys Arg Val  Ile Gln Leu Ser Arg  Lys Thr Phe
    1880                 1885                 1890

Glu Thr  Glu Phe Gln Lys Thr  Lys His Gln Glu Trp  Asp Phe Val
    1895                 1900                 1905

Val Thr  Thr Asp Ile Ser Glu  Met Gly Ala Asn Phe  Lys Ala Asp
    1910                 1915                 1920

Arg Val  Ile Asp Ser Arg Arg  Cys Leu Lys Pro Val  Ile Leu Asp
    1925                 1930                 1935

Gly Glu  Arg Val Ile Leu Ala  Gly Pro Met Pro Val  Thr His Ala
    1940                 1945                 1950

Ser Ala  Ala Gln Arg Arg Gly  Arg Ile Gly Arg Asn  Pro Asn Lys
    1955                 1960                 1965

Pro Gly  Asp Glu Tyr Leu Tyr  Gly Gly Gly Cys Ala  Glu Thr Asp
    1970                 1975                 1980

Glu Asp  His Ala His Trp Leu  Glu Ala Arg Met Leu  Leu Asp Asn
    1985                 1990                 1995

Ile Tyr  Leu Gln Asp Gly Leu  Ile Ala Ser Leu Tyr  Arg Pro Glu
    2000                 2005                 2010

Ala Asp  Lys Val Ala Ala Ile  Glu Gly Glu Phe Lys  Leu Arg Thr
    2015                 2020                 2025

Glu Gln  Arg Lys Thr Phe Val  Glu Leu Met Lys Arg  Gly Asp Leu
    2030                 2035                 2040

Pro Val  Trp Leu Ala Tyr Gln  Val Ala Ser Ala Gly  Ile Thr Tyr
    2045                 2050                 2055

Thr Asp  Arg Arg Trp Cys Phe  Asp Gly Thr Thr Asn  Asn Thr Ile
    2060                 2065                 2070

Met Glu  Asp Ser Val Pro Ala  Glu Val Trp Thr Arg  His Gly Glu
```

-continued

```
    2075                2080                2085

Lys Arg  Val Leu Lys Pro Arg  Trp Met Asp Ala Arg  Val Cys Ser
    2090                2095                2100

Asp His  Ala Ala Leu Lys Ser  Phe Lys Glu Phe Ala  Ala Gly Lys
    2105                2110                2115

Arg Gly  Ala Ala Phe Gly Val  Met Glu Ala Leu Gly  Thr Leu Pro
    2120                2125                2130

Gly His  Met Thr Glu Arg Phe  Gln Glu Ala Ile Asp  Asn Leu Ala
    2135                2140                2145

Val Leu  Met Arg Ala Glu Thr  Gly Ser Arg Pro Tyr  Lys Ala Ala
    2150                2155                2160

Ala Ala  Gln Leu Pro Glu Thr  Leu Glu Thr Ile Met  Leu Leu Gly
    2165                2170                2175

Leu Leu  Gly Thr Val Ser Leu  Gly Ile Phe Phe Val  Leu Met Arg
    2180                2185                2190

Asn Lys  Gly Ile Gly Lys Met  Gly Phe Gly Met Val  Thr Leu Gly
    2195                2200                2205

Ala Ser  Ala Trp Leu Met Trp  Leu Ser Glu Ile Glu  Pro Ala Arg
    2210                2215                2220

Ile Ala  Cys Val Leu Ile Val  Val Phe Leu Leu Leu  Val Val Leu
    2225                2230                2235

Ile Pro  Glu Pro Glu Lys Gln  Arg Ser Pro Gln Asp  Asn Gln Met
    2240                2245                2250

Ala Ile  Ile Ile Met Val Ala  Val Gly Leu Leu Gly  Leu Ile Thr
    2255                2260                2265

Ala Asn  Glu Leu Gly Trp Leu  Glu Arg Thr Lys Ser  Asp Leu Ser
    2270                2275                2280

His Leu  Met Gly Arg Arg Glu  Glu Gly Ala Thr Ile  Gly Phe Ser
    2285                2290                2295

Met Asp  Ile Asp Leu Arg Pro  Ala Ser Ala Trp Ala  Ile Tyr Ala
    2300                2305                2310

Ala Leu  Thr Thr Phe Ile Thr  Pro Ala Val Gln His  Ala Val Thr
    2315                2320                2325

Thr Ser  Tyr Asn Asn Tyr Ser  Leu Met Ala Met Ala  Thr Gln Ala
    2330                2335                2340

Gly Val  Leu Phe Gly Met Gly  Lys Gly Met Pro Phe  Tyr Ala Trp
    2345                2350                2355

Asp Phe  Gly Val Pro Leu Leu  Met Ile Gly Cys Tyr  Ser Gln Leu
    2360                2365                2370

Thr Pro  Leu Thr Leu Ile Val  Ala Ile Ile Leu Leu  Val Ala His
    2375                2380                2385

Tyr Met  Tyr Leu Ile Pro Gly  Leu Gln Ala Ala Ala  Ala Arg Ala
    2390                2395                2400

Ala Gln  Lys Arg Thr Ala Ala  Gly Ile Met Lys Asn  Pro Val Val
    2405                2410                2415

Asp Gly  Ile Val Val Thr Asp  Ile Asp Thr Met Thr  Ile Asp Pro
    2420                2425                2430

Gln Val  Glu Lys Lys Met Gly  Gln Val Leu Leu Ile  Ala Val Ala
    2435                2440                2445

Val Ser  Ser Ala Ile Leu Ser  Arg Thr Ala Trp Gly  Trp Gly Glu
    2450                2455                2460

Ala Gly  Ala Leu Ile Thr Ala  Ala Thr Ser Thr Leu  Trp Glu Gly
    2465                2470                2475
```

```
Ser Pro Asn Lys Tyr Trp Asn Ser Ser Thr Ala Thr Ser Leu Cys
    2480                2485                2490

Asn Ile Phe Arg Gly Ser Tyr Leu Ala Gly Ala Ser Leu Ile Tyr
    2495                2500                2505

Thr Val Thr Arg Asn Ala Gly Leu Val Lys Arg Arg Gly Gly Gly
    2510                2515                2520

Thr Gly Glu Thr Leu Gly Glu Lys Trp Lys Ala Arg Leu Asn Gln
    2525                2530                2535

Met Ser Ala Leu Glu Phe Tyr Ser Tyr Lys Lys Ser Gly Ile Thr
    2540                2545                2550

Glu Val Cys Arg Glu Glu Ala Arg Arg Ala Leu Lys Asp Gly Val
    2555                2560                2565

Ala Thr Gly Gly His Ala Val Ser Arg Gly Ser Ala Lys Leu Arg
    2570                2575                2580

Trp Leu Val Glu Arg Gly Tyr Leu Gln Pro Tyr Gly Lys Val Ile
    2585                2590                2595

Asp Leu Gly Cys Gly Arg Gly Gly Trp Ser Tyr Tyr Ala Ala Thr
    2600                2605                2610

Ile Arg Lys Val Gln Glu Val Lys Gly Tyr Thr Lys Gly Gly Pro
    2615                2620                2625

Gly His Glu Glu Pro Met Leu Val Gln Ser Tyr Gly Trp Asn Ile
    2630                2635                2640

Val Arg Leu Lys Ser Gly Val Asp Val Phe His Met Ala Ala Glu
    2645                2650                2655

Pro Cys Asp Thr Leu Leu Cys Asp Ile Gly Glu Ser Ser Ser Ser
    2660                2665                2670

Pro Glu Val Glu Glu Ala Arg Thr Leu Arg Val Leu Ser Met Val
    2675                2680                2685

Gly Asp Trp Leu Glu Lys Arg Pro Gly Ala Phe Cys Ile Lys Val
    2690                2695                2700

Leu Cys Pro Tyr Thr Ser Thr Met Met Glu Thr Leu Glu Arg Leu
    2705                2710                2715

Gln Arg Arg Tyr Gly Gly Gly Leu Val Arg Val Pro Leu Ser Arg
    2720                2725                2730

Asn Ser Thr His Glu Met Tyr Trp Val Ser Gly Ala Lys Ser Asn
    2735                2740                2745

Thr Ile Lys Ser Val Ser Thr Thr Ser Gln Leu Leu Leu Gly Arg
    2750                2755                2760

Met Asp Gly Pro Arg Arg Pro Val Lys Tyr Glu Glu Asp Val Asn
    2765                2770                2775

Leu Gly Ser Gly Thr Arg Ala Val Val Ser Cys Ala Glu Ala Pro
    2780                2785                2790

Asn Met Lys Ile Ile Gly Asn Arg Ile Glu Arg Ile Arg Ser Glu
    2795                2800                2805

His Ala Glu Thr Trp Phe Phe Asp Glu Asn His Pro Tyr Arg Thr
    2810                2815                2820

Trp Ala Tyr His Gly Ser Tyr Glu Ala Pro Thr Gln Gly Ser Ala
    2825                2830                2835

Ser Ser Leu Ile Asn Gly Val Val Arg Leu Leu Ser Lys Pro Trp
    2840                2845                2850

Asp Val Val Thr Gly Val Thr Gly Ile Ala Met Thr Asp Thr Thr
    2855                2860                2865
```

```
Pro Tyr Gly Gln Gln Arg Val Phe Lys Glu Lys Val Asp Thr Arg
    2870                2875                2880

Val Pro Asp Pro Gln Glu Gly Thr Arg Gln Val Met Ser Met Val
    2885                2890                2895

Ser Ser Trp Leu Trp Lys Glu Leu Gly Lys His Lys Arg Pro Arg
    2900                2905                2910

Val Cys Thr Lys Glu Glu Phe Ile Asn Lys Val Arg Ser Asn Ala
    2915                2920                2925

Ala Leu Gly Ala Ile Phe Glu Glu Glu Lys Glu Trp Lys Thr Ala
    2930                2935                2940

Val Glu Ala Val Asn Asp Pro Arg Phe Trp Ala Leu Val Asp Lys
    2945                2950                2955

Glu Arg Glu His His Leu Arg Gly Glu Cys Gln Ser Cys Val Tyr
    2960                2965                2970

Asn Met Met Gly Lys Arg Glu Lys Lys Gln Gly Glu Phe Gly Lys
    2975                2980                2985

Ala Lys Gly Ser Arg Ala Ile Trp Tyr Met Trp Leu Gly Ala Arg
    2990                2995                3000

Phe Leu Glu Phe Glu Ala Leu Gly Phe Leu Asn Glu Asp His Trp
    3005                3010                3015

Met Gly Arg Glu Asn Ser Gly Gly Gly Val Glu Gly Leu Gly Leu
    3020                3025                3030

Gln Arg Leu Gly Tyr Val Leu Glu Glu Met Ser Arg Ile Pro Gly
    3035                3040                3045

Gly Arg Met Tyr Ala Asp Asp Thr Ala Gly Trp Asp Thr Arg Ile
    3050                3055                3060

Ser Arg Phe Asp Leu Glu Asn Glu Ala Leu Ile Thr Asn Gln Met
    3065                3070                3075

Glu Lys Gly His Arg Ala Leu Ala Leu Ala Ile Ile Lys Tyr Thr
    3080                3085                3090

Tyr Gln Asn Lys Val Val Lys Val Leu Arg Pro Ala Glu Lys Gly
    3095                3100                3105

Lys Thr Val Met Asp Ile Ile Ser Arg Gln Asp Gln Arg Gly Ser
    3110                3115                3120

Gly Gln Val Val Thr Tyr Ala Leu Asn Thr Phe Thr Asn Leu Val
    3125                3130                3135

Val Gln Leu Ile Arg Asn Met Glu Ala Glu Glu Val Leu Glu Met
    3140                3145                3150

Gln Asp Leu Trp Leu Leu Arg Arg Ser Glu Lys Val Thr Asn Trp
    3155                3160                3165

Leu Gln Ser Asn Gly Trp Asp Arg Leu Lys Arg Met Ala Val Ser
    3170                3175                3180

Gly Asp Asp Cys Val Val Lys Pro Ile Asp Asp Arg Phe Ala His
    3185                3190                3195

Ala Leu Arg Phe Leu Asn Asp Met Gly Lys Val Arg Lys Asp Thr
    3200                3205                3210

Gln Glu Trp Lys Pro Ser Thr Gly Trp Asp Asn Trp Glu Glu Val
    3215                3220                3225

Pro Phe Cys Ser His His Phe Asn Lys Leu His Leu Lys Asp Gly
    3230                3235                3240

Arg Ser Ile Val Val Pro Cys Arg His Gln Asp Glu Leu Ile Gly
    3245                3250                3255

Arg Ala Arg Val Ser Pro Gly Ala Gly Trp Ser Ile Arg Glu Thr
```

```
    3260                3265                3270

Ala Cys  Leu Ala Lys Ser Tyr  Ala Gln Met Trp Gln  Leu Leu Tyr
    3275                3280                3285

Phe His  Arg Arg Asp Leu Arg  Leu Met Ala Asn Ala  Ile Cys Ser
    3290                3295                3300

Ser Val  Pro Val Asp Trp Val  Pro Thr Gly Arg Thr  Thr Trp Ser
    3305                3310                3315

Ile His  Gly Lys Gly Glu Trp  Met Thr Thr Glu Asp  Met Leu Val
    3320                3325                3330

Val Trp  Asn Arg Val Trp Ile  Glu Glu Asn Asp His  Met Glu Asp
    3335                3340                3345

Lys Thr  Pro Val Thr Lys Trp  Thr Asp Ile Pro Tyr  Leu Gly Lys
    3350                3355                3360

Arg Glu  Asp Leu Trp Cys Gly  Ser Leu Ile Gly His  Arg Pro Arg
    3365                3370                3375

Thr Thr  Trp Ala Glu Asn Ile  Lys Asn Thr Val Asn  Met Val Arg
    3380                3385                3390

Arg Ile  Ile Gly Asp Glu Glu  Lys Tyr Met Asp Tyr  Leu Ser Thr
    3395                3400                3405

Gln Val  Arg Tyr Leu Gly Glu  Glu Gly Ser Thr Pro  Gly Val Leu
    3410                3415                3420


<210> SEQ ID NO 14
<211> LENGTH: 327
<212> TYPE: PRT
<213> ORGANISM: Homo sapiens

<400> SEQUENCE: 14

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205
```

```
Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 15
<211> LENGTH: 3419
<212> TYPE: PRT
<213> ORGANISM: Unknown
<220> FEATURE:
<223> OTHER INFORMATION: Zika virus

<400> SEQUENCE: 15

Met Lys Asn Pro Lys Glu Glu Ile Arg Arg Ile Arg Ile Val Asn Met
1               5                   10                  15

Leu Lys Arg Gly Val Ala Arg Val Asn Pro Leu Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Arg Lys Arg Arg Gly Ala Asp Thr Ser Ile Gly Ile
            100                 105                 110

Ile Gly Leu Leu Leu Thr Thr Ala Met Ala Ala Glu Ile Thr Arg Arg
        115                 120                 125

Gly Ser Ala Tyr Tyr Met Tyr Leu Asp Arg Ser Asp Ala Gly Lys Ala
    130                 135                 140

Ile Ser Phe Ala Thr Thr Leu Gly Val Asn Lys Cys His Val Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220

Arg Lys Leu Gln Thr Arg Ser Gln Thr Trp Leu Glu Ser Arg Glu Tyr
225                 230                 235                 240
```

```
Thr Lys His Leu Ile Lys Val Glu Asn Trp Ile Phe Arg Asn Pro Gly
                245                 250                 255

Phe Ala Leu Val Ala Val Ala Ile Ala Trp Leu Leu Gly Ser Ser Thr
            260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
    290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
        355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Thr Cys Ser Lys Lys Met Thr
                405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Gly Tyr Glu Thr Asp Glu
        435                 440                 445

Asp Arg Ala Lys Val Glu Val Thr Pro Asn Ser Pro Arg Ala Glu Ala
    450                 455                 460

Thr Leu Gly Gly Phe Gly Ser Leu Gly Leu Asp Cys Glu Pro Arg Thr
465                 470                 475                 480

Gly Leu Asp Phe Ser Asp Leu Tyr Tyr Leu Thr Met Asn Asn Lys His
                485                 490                 495

Trp Leu Val His Lys Glu Trp Phe His Asp Ile Pro Leu Pro Trp His
            500                 505                 510

Ala Gly Ala Asp Thr Gly Thr Pro His Trp Asn Asn Lys Glu Ala Leu
        515                 520                 525

Val Glu Phe Lys Asp Ala His Ala Lys Arg Gln Thr Val Val Val Leu
    530                 535                 540

Gly Ser Gln Glu Gly Ala Val His Thr Ala Leu Ala Gly Ala Leu Glu
545                 550                 555                 560

Ala Glu Met Asp Gly Ala Lys Gly Arg Leu Phe Ser Gly His Leu Lys
                565                 570                 575

Cys Arg Leu Lys Met Asp Lys Leu Arg Leu Lys Gly Val Ser Tyr Ser
            580                 585                 590

Leu Cys Thr Ala Ala Phe Thr Phe Thr Lys Val Pro Ala Glu Thr Leu
        595                 600                 605

His Gly Thr Val Thr Val Glu Val Gln Tyr Ala Gly Thr Asp Gly Pro
    610                 615                 620

Cys Lys Ile Pro Val Gln Met Ala Val Asp Met Gln Thr Leu Thr Pro
625                 630                 635                 640

Val Gly Arg Leu Ile Thr Ala Asn Pro Val Ile Thr Glu Ser Thr Glu
                645                 650                 655

Asn Ser Lys Met Met Leu Glu Leu Asp Pro Pro Phe Gly Asp Ser Tyr
```

```
            660                 665                 670

Ile Val Ile Gly Val Gly Asp Lys Lys Ile Thr His His Trp His Arg
        675                 680                 685

Ser Gly Ser Thr Ile Gly Lys Ala Phe Glu Ala Thr Val Arg Gly Ala
    690                 695                 700

Lys Arg Met Ala Val Leu Gly Asp Thr Ala Trp Asp Phe Gly Ser Val
705                 710                 715                 720

Gly Gly Val Phe Asn Ser Leu Gly Lys Gly Ile His Gln Ile Phe Gly
                725                 730                 735

Ala Ala Phe Lys Ser Leu Phe Gly Gly Met Ser Trp Phe Ser Gln Ile
            740                 745                 750

Leu Ile Gly Thr Leu Leu Val Trp Leu Gly Leu Asn Thr Lys Asn Gly
        755                 760                 765

Ser Ile Ser Leu Thr Cys Leu Ala Leu Gly Gly Val Met Ile Phe Leu
    770                 775                 780

Ser Thr Ala Val Ser Ala Asp Val Gly Cys Ser Val Asp Phe Ser Lys
785                 790                 795                 800

Lys Glu Thr Arg Cys Gly Thr Gly Val Phe Ile Tyr Asn Asp Val Glu
                805                 810                 815

Ala Trp Arg Asp Arg Tyr Lys Tyr His Pro Asp Ser Pro Arg Arg Leu
            820                 825                 830

Ala Ala Ala Val Lys Gln Ala Trp Glu Glu Gly Ile Cys Gly Ile Ser
        835                 840                 845

Ser Val Ser Arg Met Glu Asn Ile Met Trp Lys Ser Val Glu Gly Glu
    850                 855                 860

Leu Asn Ala Ile Leu Glu Glu Asn Gly Val Gln Leu Thr Val Val Val
865                 870                 875                 880

Gly Ser Val Lys Asn Pro Met Trp Arg Gly Pro Gln Arg Leu Pro Val
                885                 890                 895

Pro Val Asn Glu Leu Pro His Gly Trp Lys Ala Trp Gly Lys Ser Tyr
            900                 905                 910

Phe Val Arg Ala Ala Lys Thr Asn Asn Ser Phe Val Val Asp Gly Asp
        915                 920                 925

Thr Leu Lys Glu Cys Pro Leu Glu His Arg Ala Trp Asn Ser Phe Leu
    930                 935                 940

Val Glu Asp His Gly Phe Gly Val Phe His Thr Ser Val Trp Leu Lys
945                 950                 955                 960

Val Arg Glu Asp Tyr Ser Leu Glu Cys Asp Pro Ala Val Ile Gly Thr
                965                 970                 975

Ala Val Lys Gly Arg Glu Ala Ala His Ser Asp Leu Gly Tyr Trp Ile
            980                 985                 990

Glu Ser Glu Lys Asn Asp Thr Trp  Arg Leu Lys Arg Ala  His Leu Ile
        995                 1000                1005

Glu Met  Lys Thr Cys Glu Trp  Pro Lys Ser His Thr  Leu Trp Thr
    1010                1015                1020

Asp Gly  Val Glu Glu Ser Asp  Leu Ile Ile Pro Lys  Ser Leu Ala
    1025                1030                1035

Gly Pro  Leu Ser His His Asn  Thr Arg Glu Gly Tyr  Arg Thr Gln
    1040                1045                1050

Val Lys  Gly Pro Trp His Ser  Glu Glu Leu Glu Ile  Arg Phe Glu
    1055                1060                1065

Glu Cys  Pro Gly Thr Lys Val  Tyr Val Glu Glu Thr  Cys Gly Thr
    1070                1075                1080
```

```
Arg Gly  Pro Ser Leu Arg Ser  Thr Thr Ala Ser Gly  Arg Val Ile
    1085                 1090                 1095

Glu Glu  Trp Cys Cys Arg Glu  Cys Thr Met Pro Pro  Leu Ser Phe
    1100                 1105                 1110

Arg Ala  Lys Asp Gly Cys Trp  Tyr Gly Met Glu Ile  Arg Pro Arg
    1115                 1120                 1125

Lys Glu  Pro Glu Ser Asn Leu  Val Arg Ser Met Val  Thr Ala Gly
    1130                 1135                 1140

Ser Thr  Asp His Met Asp His  Phe Ser Leu Gly Val  Leu Val Ile
    1145                 1150                 1155

Leu Leu  Met Val Gln Glu Gly  Leu Lys Lys Arg Met  Thr Thr Lys
    1160                 1165                 1170

Ile Ile  Met Ser Thr Ser Met  Ala Val Leu Val Val  Met Ile Leu
    1175                 1180                 1185

Gly Gly  Phe Ser Met Ser Asp  Leu Ala Lys Leu Val  Ile Leu Met
    1190                 1195                 1200

Gly Ala  Thr Phe Ala Glu Met  Asn Thr Gly Gly Asp  Val Ala His
    1205                 1210                 1215

Leu Ala  Leu Val Ala Ala Phe  Lys Val Arg Pro Ala  Leu Leu Val
    1220                 1225                 1230

Ser Phe  Ile Phe Arg Ala Asn  Trp Thr Pro Arg Glu  Ser Met Leu
    1235                 1240                 1245

Leu Ala  Leu Ala Ser Cys Leu  Leu Gln Thr Ala Ile  Ser Ala Leu
    1250                 1255                 1260

Glu Gly  Asp Leu Met Val Leu  Ile Asn Gly Phe Ala  Leu Ala Trp
    1265                 1270                 1275

Leu Ala  Ile Arg Ala Met Ala  Val Pro Arg Thr Asp  Asn Ile Ala
    1280                 1285                 1290

Leu Pro  Ile Leu Ala Ala Leu  Thr Pro Leu Ala Arg  Gly Thr Leu
    1295                 1300                 1305

Leu Val  Ala Trp Arg Ala Gly  Leu Ala Thr Cys Gly  Gly Ile Met
    1310                 1315                 1320

Leu Leu  Ser Leu Lys Gly Lys  Gly Ser Val Lys Lys  Asn Leu Pro
    1325                 1330                 1335

Phe Val  Met Ala Leu Gly Leu  Thr Ala Val Arg Val  Val Asp Pro
    1340                 1345                 1350

Ile Asn  Val Val Gly Leu Leu  Leu Leu Thr Arg Ser  Gly Lys Arg
    1355                 1360                 1365

Ser Trp  Pro Pro Ser Glu Val  Leu Thr Ala Val Gly  Leu Ile Cys
    1370                 1375                 1380

Ala Leu  Ala Gly Gly Phe Ala  Lys Ala Asp Ile Glu  Met Ala Gly
    1385                 1390                 1395

Pro Met  Ala Ala Val Gly Leu  Leu Ile Val Ser Tyr  Val Val Ser
    1400                 1405                 1410

Gly Lys  Ser Val Asp Met Tyr  Ile Glu Arg Ala Gly  Asp Ile Thr
    1415                 1420                 1425

Trp Glu  Lys Asp Ala Glu Val  Thr Gly Asn Ser Pro  Arg Leu Asp
    1430                 1435                 1440

Val Ala  Leu Asp Glu Ser Gly  Asp Phe Ser Leu Val  Glu Glu Asp
    1445                 1450                 1455

Gly Pro  Pro Met Arg Glu Ile  Ile Leu Lys Val Val  Leu Met Ala
    1460                 1465                 1470
```

Ile Cys Gly Met Asn Pro Ile Ala Ile Pro Phe Ala Ala Gly Ala
1475 1480 1485

Trp Tyr Val Tyr Val Lys Thr Gly Lys Arg Ser Gly Ala Leu Trp
1490 1495 1500

Asp Val Pro Ala Pro Lys Glu Val Lys Lys Gly Glu Thr Thr Asp
1505 1510 1515

Gly Val Tyr Arg Val Met Thr Arg Arg Leu Leu Gly Ser Thr Gln
1520 1525 1530

Val Gly Val Gly Val Met Gln Glu Gly Val Phe His Thr Met Trp
1535 1540 1545

His Val Thr Lys Gly Ala Ala Leu Arg Ser Gly Glu Gly Arg Leu
1550 1555 1560

Asp Pro Tyr Trp Gly Asp Val Lys Gln Asp Leu Val Ser Tyr Cys
1565 1570 1575

Gly Pro Trp Lys Leu Asp Ala Ala Trp Asp Gly Leu Ser Glu Val
1580 1585 1590

Gln Leu Leu Ala Val Pro Pro Gly Glu Arg Ala Arg Asn Ile Gln
1595 1600 1605

Thr Leu Pro Gly Ile Phe Lys Thr Lys Asp Gly Asp Ile Gly Ala
1610 1615 1620

Val Ala Leu Asp Tyr Pro Ala Gly Thr Ser Gly Ser Pro Ile Leu
1625 1630 1635

Asp Lys Cys Gly Arg Val Ile Gly Leu Tyr Gly Asn Gly Val Val
1640 1645 1650

Ile Lys Asn Gly Ser Tyr Val Ser Ala Ile Thr Gln Gly Lys Arg
1655 1660 1665

Glu Glu Glu Thr Pro Val Glu Cys Phe Glu Pro Ser Met Leu Lys
1670 1675 1680

Lys Lys Gln Leu Thr Val Leu Asp Leu His Pro Gly Ala Gly Lys
1685 1690 1695

Thr Arg Arg Val Leu Pro Glu Ile Val Arg Glu Ala Ile Lys Lys
1700 1705 1710

Arg Leu Arg Thr Val Ile Leu Ala Pro Thr Arg Val Val Ala Ala
1715 1720 1725

Glu Met Glu Glu Ala Leu Arg Gly Leu Pro Val Arg Tyr Met Thr
1730 1735 1740

Thr Ala Val Asn Val Thr His Ser Gly Thr Glu Ile Val Asp Leu
1745 1750 1755

Met Cys His Ala Thr Phe Thr Ser Arg Leu Leu Gln Pro Ile Arg
1760 1765 1770

Val Pro Asn Tyr Asn Leu Asn Ile Met Asp Glu Ala His Phe Thr
1775 1780 1785

Asp Pro Ser Ser Ile Ala Ala Arg Gly Tyr Ile Ser Thr Arg Val
1790 1795 1800

Glu Met Gly Glu Ala Ala Ala Ile Phe Met Thr Ala Thr Pro Pro
1805 1810 1815

Gly Thr Arg Asp Ala Phe Pro Asp Ser Asn Ser Pro Ile Met Asp
1820 1825 1830

Thr Glu Val Glu Val Pro Glu Arg Ala Trp Ser Ser Gly Phe Asp
1835 1840 1845

Trp Val Thr Asp His Ser Gly Lys Thr Val Trp Phe Val Pro Ser
1850 1855 1860

Val Arg Asn Gly Asn Glu Ile Ala Ala Cys Leu Thr Lys Ala Gly

```
    1865                1870                1875

Lys Arg Val Ile Gln Leu Ser Arg Lys Thr Phe Glu Thr Glu Phe
    1880                1885                1890

Gln Lys Thr Lys Asn Gln Glu Trp Asp Phe Val Ile Thr Thr Asp
    1895                1900                1905

Ile Ser Glu Met Gly Ala Asn Phe Lys Ala Asp Arg Val Ile Asp
    1910                1915                1920

Ser Arg Arg Cys Leu Lys Pro Val Ile Leu Asp Gly Glu Arg Val
    1925                1930                1935

Ile Leu Ala Gly Pro Met Pro Val Thr His Ala Ser Ala Ala Gln
    1940                1945                1950

Arg Arg Gly Arg Ile Gly Arg Asn Pro Asn Lys Pro Gly Asp Glu
    1955                1960                1965

Tyr Met Tyr Gly Gly Gly Cys Ala Glu Thr Asp Glu Gly His Ala
    1970                1975                1980

His Trp Leu Glu Ala Arg Met Leu Leu Asp Asn Ile Tyr Leu Gln
    1985                1990                1995

Asp Gly Leu Ile Ala Ser Leu Tyr Arg Pro Glu Ala Asp Lys Val
    2000                2005                2010

Ala Ala Ile Glu Gly Glu Phe Lys Leu Arg Thr Glu Gln Arg Lys
    2015                2020                2025

Thr Phe Val Glu Leu Met Lys Arg Gly Asp Leu Pro Val Trp Leu
    2030                2035                2040

Ala Tyr Gln Val Ala Ser Ala Gly Ile Thr Tyr Thr Asp Arg Arg
    2045                2050                2055

Trp Cys Phe Asp Gly Thr Thr Asn Asn Thr Ile Met Glu Asp Ser
    2060                2065                2070

Val Pro Ala Glu Val Trp Thr Lys Tyr Gly Glu Lys Arg Val Leu
    2075                2080                2085

Lys Pro Arg Trp Met Asp Ala Arg Val Cys Ser Asp His Ala Ala
    2090                2095                2100

Leu Lys Ser Phe Lys Glu Phe Ala Ala Gly Lys Arg Gly Ala Ala
    2105                2110                2115

Leu Gly Val Met Glu Ala Leu Gly Thr Leu Pro Gly His Met Thr
    2120                2125                2130

Glu Arg Phe Gln Glu Ala Ile Asp Asn Leu Ala Val Leu Met Arg
    2135                2140                2145

Ala Glu Thr Gly Ser Arg Pro Tyr Lys Ala Ala Ala Ala Gln Leu
    2150                2155                2160

Pro Glu Thr Leu Glu Thr Ile Met Leu Leu Gly Leu Leu Gly Thr
    2165                2170                2175

Val Ser Leu Gly Ile Phe Phe Val Leu Met Arg Asn Lys Gly Ile
    2180                2185                2190

Gly Lys Met Gly Phe Gly Met Val Thr Leu Gly Ala Ser Ala Trp
    2195                2200                2205

Leu Met Trp Leu Ser Glu Ile Glu Pro Ala Arg Ile Ala Cys Val
    2210                2215                2220

Leu Ile Val Val Phe Leu Leu Leu Val Val Leu Ile Pro Glu Pro
    2225                2230                2235

Glu Lys Gln Arg Ser Pro Gln Asp Asn Gln Met Ala Ile Ile Ile
    2240                2245                2250

Met Val Ala Val Gly Leu Leu Gly Leu Ile Thr Ala Asn Glu Leu
    2255                2260                2265
```

Gly Trp Leu Glu Arg Thr Lys Asn Asp Ile Ala His Leu Met Gly
2270 2275 2280

Arg Arg Glu Glu Gly Ala Thr Met Gly Phe Ser Met Asp Ile Asp
2285 2290 2295

Leu Arg Pro Ala Ser Ala Trp Ala Ile Tyr Ala Ala Leu Thr Thr
2300 2305 2310

Leu Ile Thr Pro Ala Val Gln His Ala Val Thr Thr Ser Tyr Asn
2315 2320 2325

Asn Tyr Ser Leu Met Ala Met Ala Thr Gln Ala Gly Val Leu Phe
2330 2335 2340

Gly Met Gly Lys Gly Met Pro Phe Met His Gly Asp Leu Gly Val
2345 2350 2355

Pro Leu Leu Met Met Gly Cys Tyr Ser Gln Leu Thr Pro Leu Thr
2360 2365 2370

Leu Ile Val Ala Ile Ile Leu Leu Val Ala His Tyr Met Tyr Leu
2375 2380 2385

Ile Pro Gly Leu Gln Ala Ala Ala Ala Arg Ala Ala Gln Lys Arg
2390 2395 2400

Thr Ala Ala Gly Ile Met Lys Asn Pro Val Val Asp Gly Ile Val
2405 2410 2415

Val Thr Asp Ile Asp Thr Met Thr Ile Asp Pro Gln Val Glu Lys
2420 2425 2430

Lys Met Gly Gln Val Leu Leu Ile Ala Val Ala Ile Ser Ser Ala
2435 2440 2445

Val Leu Leu Arg Thr Ala Trp Gly Trp Gly Glu Ala Gly Ala Leu
2450 2455 2460

Ile Thr Ala Ala Thr Ser Thr Leu Trp Glu Gly Ser Pro Asn Lys
2465 2470 2475

Tyr Trp Asn Ser Ser Thr Ala Thr Ser Leu Cys Asn Ile Phe Arg
2480 2485 2490

Gly Ser Tyr Leu Ala Gly Ala Ser Leu Ile Tyr Thr Val Thr Arg
2495 2500 2505

Asn Ala Gly Leu Val Lys Arg Arg Gly Gly Gly Thr Gly Glu Thr
2510 2515 2520

Leu Gly Glu Lys Trp Lys Ala Arg Leu Asn Gln Met Ser Ala Leu
2525 2530 2535

Glu Phe Tyr Ser Tyr Lys Lys Ser Gly Ile Thr Glu Val Cys Arg
2540 2545 2550

Glu Glu Ala Arg Arg Ala Leu Lys Asp Gly Val Ala Thr Gly Gly
2555 2560 2565

His Ala Val Ser Arg Gly Ser Ala Lys Ile Arg Trp Leu Glu Glu
2570 2575 2580

Arg Gly Tyr Leu Gln Pro Tyr Gly Lys Val Val Asp Leu Gly Cys
2585 2590 2595

Gly Arg Gly Gly Trp Ser Tyr Tyr Ala Ala Thr Ile Arg Lys Val
2600 2605 2610

Gln Glu Val Arg Gly Tyr Thr Lys Gly Gly Pro Gly His Glu Glu
2615 2620 2625

Pro Met Leu Val Gln Ser Tyr Gly Trp Asn Ile Val Arg Leu Lys
2630 2635 2640

Ser Gly Val Asp Val Phe His Met Ala Ala Glu Pro Cys Asp Thr
2645 2650 2655

-continued

```
Leu Leu Cys Asp Ile Gly Glu Ser Ser Ser Ser Pro Glu Val Glu
    2660                2665                2670

Glu Thr Arg Thr Leu Arg Val Leu Ser Met Val Gly Asp Trp Leu
    2675                2680                2685

Glu Lys Arg Pro Gly Ala Phe Cys Ile Lys Val Leu Cys Pro Tyr
    2690                2695                2700

Thr Ser Thr Met Met Glu Thr Met Glu Arg Leu Gln Arg Arg His
    2705                2710                2715

Gly Gly Gly Leu Val Arg Val Pro Leu Cys Arg Asn Ser Thr His
    2720                2725                2730

Glu Met Tyr Trp Val Ser Gly Ala Lys Ser Asn Ile Ile Lys Ser
    2735                2740                2745

Val Ser Thr Thr Ser Gln Leu Leu Leu Gly Arg Met Asp Gly Pro
    2750                2755                2760

Arg Arg Pro Val Lys Tyr Glu Glu Asp Val Asn Leu Gly Ser Gly
    2765                2770                2775

Thr Arg Ala Val Ala Ser Cys Ala Glu Ala Pro Asn Met Lys Ile
    2780                2785                2790

Ile Gly Arg Arg Ile Glu Arg Ile Arg Asn Glu His Ala Glu Thr
    2795                2800                2805

Trp Phe Leu Asp Glu Asn His Pro Tyr Arg Thr Trp Ala Tyr His
    2810                2815                2820

Gly Ser Tyr Glu Ala Pro Thr Gln Gly Ser Ala Ser Ser Leu Val
    2825                2830                2835

Asn Gly Val Val Arg Leu Leu Ser Lys Pro Trp Asp Val Val Thr
    2840                2845                2850

Gly Val Thr Gly Ile Ala Met Thr Asp Thr Thr Pro Tyr Gly Gln
    2855                2860                2865

Gln Arg Val Phe Lys Glu Lys Val Asp Thr Arg Val Pro Asp Pro
    2870                2875                2880

Gln Glu Gly Thr Arg Gln Val Met Asn Ile Val Ser Ser Trp Leu
    2885                2890                2895

Trp Lys Glu Leu Gly Lys Arg Lys Arg Pro Arg Val Cys Thr Lys
    2900                2905                2910

Glu Glu Phe Ile Asn Lys Val Arg Ser Asn Ala Ala Leu Gly Ala
    2915                2920                2925

Ile Phe Glu Glu Glu Lys Glu Trp Lys Thr Ala Val Glu Ala Val
    2930                2935                2940

Asn Asp Pro Arg Phe Trp Ala Leu Val Asp Arg Glu Arg Glu His
    2945                2950                2955

His Leu Arg Gly Glu Cys His Ser Cys Val Tyr Asn Met Met Gly
    2960                2965                2970

Lys Arg Glu Lys Lys Gln Gly Glu Phe Gly Lys Ala Lys Gly Ser
    2975                2980                2985

Arg Ala Ile Trp Tyr Met Trp Leu Gly Ala Arg Phe Leu Glu Phe
    2990                2995                3000

Glu Ala Leu Gly Phe Leu Asn Glu Asp His Trp Met Gly Arg Glu
    3005                3010                3015

Asn Ser Gly Gly Gly Val Glu Gly Leu Gly Leu Gln Arg Leu Gly
    3020                3025                3030

Tyr Ile Leu Glu Glu Met Asn Arg Ala Pro Gly Gly Lys Met Tyr
    3035                3040                3045

Ala Asp Asp Thr Ala Gly Trp Asp Thr Arg Ile Ser Lys Phe Asp
```

```
    3050                3055                3060

Leu Glu  Asn Glu Ala Leu Ile  Thr Asn Gln Met Glu  Glu Gly His
    3065                3070                3075

Arg Thr  Leu Ala Leu Ala Val  Ile Lys Tyr Thr Tyr  Gln Asn Lys
    3080                3085                3090

Val Val  Lys Val Leu Arg Pro  Ala Glu Gly Gly Lys  Thr Val Met
    3095                3100                3105

Asp Ile  Ile Ser Arg Gln Asp  Gln Arg Gly Ser Gly  Gln Val Val
    3110                3115                3120

Thr Tyr  Ala Leu Asn Thr Phe  Thr Asn Leu Val Val  Gln Leu Ile
    3125                3130                3135

Arg Asn  Met Glu Ala Glu Glu  Val Leu Glu Met Gln  Asp Leu Trp
    3140                3145                3150

Leu Leu  Arg Lys Pro Glu Lys  Val Thr Arg Trp Leu  Gln Ser Asn
    3155                3160                3165

Gly Trp  Asp Arg Leu Lys Arg  Met Ala Val Ser Gly  Asp Asp Cys
    3170                3175                3180

Val Val  Lys Pro Ile Asp Asp  Arg Phe Ala His Ala  Leu Arg Phe
    3185                3190                3195

Leu Asn  Asp Met Gly Lys Val  Arg Lys Asp Thr Gln  Glu Trp Lys
    3200                3205                3210

Pro Ser  Thr Gly Trp Ser Asn  Trp Glu Glu Val Pro  Phe Cys Ser
    3215                3220                3225

His His  Phe Asn Lys Leu Tyr  Leu Lys Asp Gly Arg  Ser Ile Val
    3230                3235                3240

Val Pro  Cys Arg His Gln Asp  Glu Leu Ile Gly Arg  Ala Arg Val
    3245                3250                3255

Ser Pro  Gly Ala Gly Trp Ser  Ile Arg Glu Thr Ala  Cys Leu Ala
    3260                3265                3270

Lys Ser  Tyr Ala Gln Met Trp  Gln Leu Leu Tyr Phe  His Arg Arg
    3275                3280                3285

Asp Leu  Arg Leu Met Ala Asn  Ala Ile Cys Ser Ala  Val Pro Val
    3290                3295                3300

Asp Trp  Val Pro Thr Gly Arg  Thr Thr Trp Ser Ile  His Gly Lys
    3305                3310                3315

Gly Glu  Trp Met Thr Thr Glu  Asp Met Leu Met Val  Trp Asn Arg
    3320                3325                3330

Val Trp  Ile Glu Glu Asn Asp  His Met Glu Asp Lys  Thr Pro Val
    3335                3340                3345

Thr Lys  Trp Thr Asp Ile Pro  Tyr Leu Gly Lys Arg  Glu Asp Leu
    3350                3355                3360

Trp Cys  Gly Ser Leu Ile Gly  His Arg Pro Arg Thr  Thr Trp Ala
    3365                3370                3375

Glu Asn  Ile Lys Asp Thr Val  Asn Met Val Arg Arg  Ile Ile Gly
    3380                3385                3390

Asp Glu  Glu Lys Tyr Met Asp  Tyr Leu Ser Thr Gln  Val Arg Tyr
    3395                3400                3405

Leu Gly  Glu Glu Gly Ser Thr  Pro Gly Val Leu
    3410                3415
```

<210> SEQ ID NO 16
<211> LENGTH: 504
<212> TYPE: PRT
<213> ORGANISM: Unknown

<220> FEATURE:
<223> OTHER INFORMATION: Zika virus

<400> SEQUENCE: 16

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400
```

```
His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 17
<211> LENGTH: 51
<212> TYPE: PRT
<213> ORGANISM: Unknown
<220> FEATURE:
<223> OTHER INFORMATION: ZIKV ED1

<400> SEQUENCE: 17

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser
    50


<210> SEQ ID NO 18
<211> LENGTH: 61
<212> TYPE: PRT
<213> ORGANISM: Unknown
<220> FEATURE:
<223> OTHER INFORMATION: ZIKV ED1

<400> SEQUENCE: 18

Pro Glu Asn Leu Glu Tyr Arg Ile Met Leu Ser Val His Gly Ser Gln
1               5                   10                  15

His Ser Gly Met Ile Val Asn Asp Thr Gly His Glu Thr Asp Glu Asn
            20                  25                  30

Arg Ala Lys Val Glu Ile Thr Pro Asn Ser Pro Arg Ala Glu Ala Thr
        35                  40                  45

Leu Gly Gly Phe Gly Ser Leu Gly Leu Asp Cys Glu Pro
    50                  55                  60


<210> SEQ ID NO 19
<211> LENGTH: 16
<212> TYPE: PRT
<213> ORGANISM: Unknown
<220> FEATURE:
<223> OTHER INFORMATION: ZIKV ED1

<400> SEQUENCE: 19

Ala Lys Gly Arg Leu Ser Ser Gly His Leu Lys Cys Arg Leu Lys Met
1               5                   10                  15
```

<210> SEQ ID NO 20
<211> LENGTH: 80
<212> TYPE: PRT
<213> ORGANISM: Unknown
<220> FEATURE:
<223> OTHER INFORMATION: ZIKV ED2

<400> SEQUENCE: 20

```
Asn Met Ala Glu Val Arg Ser Tyr Cys Tyr Glu Ala Ser Ile Ser Asp
1               5                   10                  15

Met Ala Ser Asp Ser Arg Cys Pro Thr Gln Gly Glu Ala Tyr Leu Asp
            20                  25                  30

Lys Gln Ser Asp Thr Gln Tyr Val Cys Lys Arg Thr Leu Val Asp Arg
        35                  40                  45

Gly Trp Gly Asn Gly Cys Gly Leu Phe Gly Lys Gly Ser Leu Val Thr
    50                  55                  60

Cys Ala Lys Phe Ala Cys Ser Lys Lys Met Thr Gly Lys Ser Ile Gln
65                  70                  75                  80
```

<210> SEQ ID NO 21
<211> LENGTH: 87
<212> TYPE: PRT
<213> ORGANISM: Unknown
<220> FEATURE:
<223> OTHER INFORMATION: ZIKV ED2

<400> SEQUENCE: 21

```
Arg Thr Gly Leu Asp Phe Ser Asp Leu Tyr Tyr Leu Thr Met Asn Asn
1               5                   10                  15

Lys His Trp Leu Val His Lys Glu Trp Phe His Asp Ile Pro Leu Pro
            20                  25                  30

Trp His Ala Gly Ala Asp Thr Gly Thr Pro His Trp Asn Asn Lys Glu
        35                  40                  45

Ala Leu Val Glu Phe Lys Asp Ala His Ala Lys Arg Gln Thr Val Val
    50                  55                  60

Val Leu Gly Ser Gln Glu Gly Ala Val His Thr Ala Leu Ala Gly Ala
65                  70                  75                  80

Leu Glu Ala Glu Met Asp Gly
                85
```

<210> SEQ ID NO 22
<211> LENGTH: 108
<212> TYPE: PRT
<213> ORGANISM: Unknown
<220> FEATURE:
<223> OTHER INFORMATION: ZIKV ED3

<400> SEQUENCE: 22

```
Asp Lys Leu Arg Leu Lys Gly Val Ser Tyr Ser Leu Cys Thr Ala Ala
1               5                   10                  15

Phe Thr Phe Thr Lys Ile Pro Ala Glu Thr Leu His Gly Thr Val Thr
            20                  25                  30

Val Glu Val Gln Tyr Ala Gly Thr Asp Gly Pro Cys Lys Val Pro Ala
        35                  40                  45

Gln Met Ala Val Asp Met Gln Thr Leu Thr Pro Val Gly Arg Leu Ile
    50                  55                  60

Thr Ala Asn Pro Val Ile Thr Glu Ser Thr Glu Asn Ser Lys Met Met
65                  70                  75                  80

Leu Glu Leu Asp Pro Pro Phe Gly Asp Ser Tyr Ile Val Ile Gly Val
```

```
                85                  90                  95

Gly Glu Lys Lys Ile Thr His His Trp His Arg Ser
            100                 105


<210> SEQ ID NO 23
<211> LENGTH: 113
<212> TYPE: PRT
<213> ORGANISM: Artificial Sequence
<220> FEATURE:
<223> OTHER INFORMATION: Synthetic polypeptide

<400> SEQUENCE: 23

Glu Val Gln Leu Leu Glu Ser Gly Gly Gly Leu Val Gln Ala Gly Gly
1               5                   10                  15

Ser Leu Arg Leu Ser Cys Ala Ala Ser Gly Phe Thr Phe Asp Thr Tyr
            20                  25                  30

Ala Met Ser Trp Val Arg Gln Pro Pro Gly Lys Gly Leu Glu Trp Val
        35                  40                  45

Ser Ala Ile Ser Thr Gly Gly Gly Ser Lys Tyr Tyr Ala Asp Ser Val
    50                  55                  60

Lys Gly Arg Leu Thr Ile Ser Arg Asp Asn Ser Gln Asn Thr Leu Tyr
65                  70                  75                  80

Leu Gln Met Ser Ser Leu Arg Ala Asp Asp Thr Ala Val Tyr Tyr Cys
                85                  90                  95

Ala Arg Ser Asp Phe Trp Arg Ser Gly Arg Tyr Tyr Tyr Tyr Met Asp
            100                 105                 110

Val


<210> SEQ ID NO 24
<211> LENGTH: 101
<212> TYPE: PRT
<213> ORGANISM: Artificial Sequence
<220> FEATURE:
<223> OTHER INFORMATION: Synthetic polypeptide

<400> SEQUENCE: 24

Gln Ser Ala Leu Thr Gln Pro Ala Ser Val Ser Ala Ser Pro Gly Gln
1               5                   10                  15

Ser Ile Thr Ile Ser Cys Thr Gly Thr His Phe Asp Ile Val Asp Tyr
            20                  25                  30

Asp Tyr Leu Ser Trp Tyr Gln Gln His Pro Gly Asn Ala Pro Lys Leu
        35                  40                  45

Leu Ile Tyr Gly Val Ser Asn Arg Pro Ser Gly Val Ser Ser Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Gly Asp Tyr Tyr Cys Ser Ser Tyr Ser Ile Ser
                85                  90                  95

Ser Thr Leu Leu Val
            100


<210> SEQ ID NO 25
<211> LENGTH: 115
<212> TYPE: PRT
<213> ORGANISM: Artificial Sequence
<220> FEATURE:
<223> OTHER INFORMATION: Synthetic polypeptide

<400> SEQUENCE: 25
```

-continued

```
Val Gln Leu Val Glu Ser Gly Gly Gly Val Val Gln Pro Gly Arg Ser
1               5                   10                  15

Leu Arg Leu Ser Cys Val Ala Ser Gly Phe Ala Phe Ser Asn Tyr His
            20                  25                  30

His His Trp Val Arg Gln Ala Pro Gly Lys Gly Leu Glu Trp Val Ala
        35                  40                  45

Ile Ile Trp Asp Asp Gly Ser Asp Gln Tyr Tyr Asp Ser Tyr Lys Gln
    50                  55                  60

Arg Phe Thr Ile Ser Arg Asp Asn Ser Lys Asn Thr Leu Phe Leu Gln
65                  70                  75                  80

Met Asn Arg Leu Arg Ala Glu Asp Thr Ala Leu Tyr Tyr Cys Val Gly
                85                  90                  95

Gly Ser Ser Ala Tyr Asn Gly Asp Asn Gly Trp Arg Glu Ala Ala Ser
            100                 105                 110

Leu Asp Asp
        115


<210> SEQ ID NO 26
<211> LENGTH: 100
<212> TYPE: PRT
<213> ORGANISM: Artificial Sequence
<220> FEATURE:
<223> OTHER INFORMATION: Synthetic polypeptide

<400> SEQUENCE: 26

Gln Ser Ala Leu Thr Gln Pro Ala Ser Val Ser Gly Ser Pro Gly Gln
1               5                   10                  15

Ser Ile Thr Ile Phe Cys Ser Gly Ser Ser Asn Asp Val Gly Gly Tyr
            20                  25                  30

Asn Tyr Val Ser Trp Tyr Gln Gln Tyr Pro Gly Lys Val Pro Lys Leu
        35                  40                  45

Leu Ile Tyr Asp Val Asn Ser Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Arg
                85                  90                  95

Arg Thr Trp Val
            100
```